US006232445B1

(12) United States Patent
Rhode et al.

(10) Patent No.: US 6,232,445 B1
(45) Date of Patent: May 15, 2001

(54) SOLUBLE MHC COMPLEXES AND METHODS OF USE THEREOF

(75) Inventors: Peter R. Rhode; Jorge Acevedo; Martin Burkhardt, all of Miami; Jin-an Jiao; Hing C. Wong, both of Fort Lauderdale, all of FL (US)

(73) Assignee: Sunol Molecular Corporation, Miramar, FL (US)

( * ) Notice: Subject to any disclaimer, the term of this patent is extended or adjusted under 35 U.S.C. 154(b) by 0 days.

(21) Appl. No.: 08/960,190

(22) Filed: Oct. 29, 1997

(51) Int. Cl.$^7$ .................... C12P 21/08; C12N 15/09; A61K 39/00; A61K 39/385
(52) U.S. Cl. .................. 530/387.3; 530/350; 530/395; 435/69.3; 424/185.1; 424/193.1; 424/192.1; 424/133.1
(58) Field of Search .................................... 530/350, 395, 530/403, 387.3; 435/69.3; 424/185.1, 193.1, 192.1, 133.1

(56) References Cited

U.S. PATENT DOCUMENTS

| 5,130,297 | 7/1992 | Sharma et al. . |
| 5,194,425 | 3/1993 | Sharma et al. . |
| 5,260,422 | * 11/1993 | Clark et al. . |
| 5,284,935 | 2/1994 | Clark et al. . |
| 5,399,567 | 3/1995 | Platt et al. . |
| 5,627,048 | * 5/1997 | Afanasieo et al. . |
| 5,656,641 | 8/1997 | Platt et al. . |
| 5,801,185 | 9/1998 | Platt et al. . |
| 5,820,866 | * 10/1998 | Kappler et al. . |
| 5,869,270 | * 2/1999 | Rhode et al. . |
| 5,976,551 | * 11/1999 | Mottez et al. . |

FOREIGN PATENT DOCUMENTS

| WO 89/12458 | 12/1989 | (WO) . |
| WO 92/18150 | 10/1992 | (WO) . |
| WO 93/10220 | 3/1993 | (WO) . |
| WO 93/09810 | 5/1993 | (WO) . |
| WO 94/18998 | 9/1994 | (WO) . |
| WO 94/25054 | 11/1994 | (WO) . |
| WO 95/23814 | 9/1995 | (WO) . |
| WO 96/04314 | 2/1996 | (WO) . |
| WO 96/05228 | 2/1996 | (WO) . |
| WO 97/28191 | 8/1997 | (WO) . |

OTHER PUBLICATIONS

H. Konozo et al., *Nature*, 369:151–154 (1994).
J. Altman, et al., *Proc. Natl. Acad. Sci, USA*, 90:10330–10334 (1993).
L. Stern, et al., *Nature*, 368:215–221 (1994).
S. Sharma, et al., *Proc. Natl. Acad. Sci. USA*, 88:11465–11469 (1991).
J. Guery, et al., *Critical Reviews in Immunology*, 13(3/4):195–206 (1993).
M. Nicolle, et al., *J. Clin. Invest.*, 93:1361–1369 (1994).
D. Harlan, et al., *Proc. Natl. Acad. Sci. USA*, 91:3137–3141 (1994).
E. Evahold, et al., *Immunology Today*, 14(12):602–609 (1993).
R. Chicz, et al., *Immunology Today*, 15(4):155–160 (1994).
R. Tisch, et al., *Proc. Natl. Acad. Sci. USA*, 91:437–438 (1994).
*Science*, 259:1691–1692 (1993).
J. Ulmer, et al., *Science*, 259:1745–1749 (1993).
H. Ploegh, et al., *Nature*, 364:16–17 (1993).
J. Brown, et al., *Nature*, 364:33–39 (1993).
D. O'Sullivan, et al., *Journal of Immunology*, 147:2663–2669 (1991).
J. Hammer, et al., *J. Exp. Med.*, 176:1007–1013 (1992).
L. Stern, et al., *Cell*, 68:465–477 (1992).
K. Webber, et al., *Molecular Immunology*, 32:249–258 (1995).
Y. Reiter, et al., *The Journal of Biological Chemistry*, 269:18327–18331 (1994).
K. O'Neil, et al., *Science*, 249:774–778. (1990).
K. O'Neil, et al., *Science*, 249:774–778, (1990).
Godeau, et al., *Journal of Biological Chemistry*: "Purification and Ligand Binding of a Soluble Class 1 Major Histocompatibility Complex Module Consisting of the First Three Domains of H–2K$^d$ Fused" 267: 24223 (1992).
J. C. Gorga, Ph.D., "Structural Analysis of Class II Major Histocompatibility Complex Proteins", *Critical Review in Immunology*, 11(5): pp. 305–335 (1992).
D. H. Margulies, et al., "Engineering Soluble Major Histocompatibility Molecules: Why and How", *Immunol. Res.*, 6: pp. 101–116 (1987).
B. Nag, et al., "Stimulation of T cells by Antigenic Peptide Complexed With Isolated Chains of Major Histocompatibility Complex Class II Molecules", *Proc. Natl. Acad. Sci. USA*, 90: pp. 1604–1608 (1993).

* cited by examiner

Primary Examiner—David Saunders
Assistant Examiner—Amy DeCloux
(74) Attorney, Agent, or Firm—Peter F. Corless; Robert L. Buchanan

(57) ABSTRACT

The present invention relates to novel complexes of major histocompatibility complex (MHC) molecules and uses of such complexes. In one aspect, the invention relates to single chain MHC class II complexes that include a class II β2 chain modification, e.g., deletion of essentially the entire class II β2 chain. In another aspect, the invention features single chain MHC class II which comprise an immunoglobin constant chain or fragment. Further provided are polyspecific MHC complexes comprising at least one single chain MHC class II molecule. MHC complexes of the invention are useful for a variety of applications including: 1) in vitro screens for identification and isolation of peptides that modulate activity of selected T cells, including peptides that are T cell receptor antagonists and partial agonists, and 2) methods for suppressing or inducing an immune response in a mammal.

20 Claims, 26 Drawing Sheets

CCACC ATG GCT CTG CAG ATC CCC AGC CTC CTC TCA GCT GCT GTG GTG CTG ATG GTG CTG AGC AGC CCA AGG
      M   A   L   Q   I   P   S   L   L   S   A   A   V   V   L   M   V   L   S   S   P   R
KOZAK  |————————————————————— IA$^d$ β CHAIN SIGNAL PEPTIDE —————————————————————|
CONSENSUS

ACC TTA AGT ATC TCT CAG GCT GTT CAC GCT GCT CAC GCT GAA ATC AAC GAA GCT GGT CGT
 T   L   S   I   S   Q   A   V   H   A   A   H   A   E   I   N   E   A   G   R
        |————————————————— OVA 323-339 PEPTIDE ————————————————|

GCT AGC GGA GGG GGC GGA AGC GGC GGA GGG GGA AAC TCC GAA AGG // AGC CCC ATC ACT GTG GAG TGG
 A   S   G   G   G   G   S   G   G   G   G   N   S   E   R  //  S   P   I   T   V   E   W
                                            |aa1            IA$^d$ β1-β2 DOMAINS        aa189|
|—————————————— PEPTIDE LINKER ——————————————|

ACT AGT GGT GGT GGC GGT TCT GGT GGC GGC GGG AGC GGC GGT GGC GGG TCT GGC GGT GGC GGG TCC TCG AGT
 T   S   G   G   G   G   S   G   G   G   G   S   G   G   G   G   S   G   G   G   G   S   S   S
|———————————————————————————— SINGLE CHAIN LINKER ————————————————————————————|

GAA GAC GAC ATT // CCA GGG CCT TTA TGA
 E   D   D   I  //  P   G   P   L   •
|aa1                              STOP
|———— IA$^d$ α CHAIN

FIG. 1

FIG. 4A sc-1A$^d$/PEPTIDE FUSION
| SP | PEP | L1 | IA$^d$ β1-β2 | L2 | IA$^d$ α1-α2 | sc-1A$^d$/PEPTIDE-TAG FUSION
| SP | PEP | L1 | IA$^d$ β1-β2 | L2 | IA$^d$ α1-α2 | EE | sc-1A$^d$TM/PEPTIDE FUSION
| SP | PEP | L1 | IA$^d$ β1-β2 | L2 | IA$^d$ α1-α2 | IA$^d$ αTM-Cy | sc-1A$^d$/PEPTIDE-C$_L$ FUSION
| SP | PEP | L1 | IA$^d$ β1-β2 | L2 | IA$^d$ α1-α2 | IgG C$_L$ |

FIG. 4B sc-DR2-β2/PEPTIDE-TAG FUSION
| SP | PEP | L1 | DRB1*1501 β1-β2 | L2 | DRAα1-α2 | EE | sc-DR2-β2/PEPTIDE FUSION
| SP | PEP | L1 | DRB1*1501 β1 | L2 | DRAα1-α2 | EE | sc-DR2 MOD β2/PEPTIDE FUSION
| SP | PEP | L1 | DRB1*1501 MOD β2 | L2 | DRAα1-α2 | EE | sc-DR2/PEPTIDE-C$_L$ FUSION
| SP | PEP | L1 | DRB1*1501 β1-β2 | L2 | DRAα1-α2 | IgG C$_L$ |

|  | SEQ No. |
|---|---|
| CCACCATG | 1 |
| OPR132<br>5'-CCCCCCAAGCTTCCCGGGCCACCATGGCTCTGCAGATCCCCAGC-3' | 2 |
| OPR133<br>5'-CCCCCCACTTAAGGTCCTTGGGCTGCTCAGCACC-3' | 3 |
| OPR102<br>5'-GGGGGGGCCATGGCCGGAAACTCCGAAAGGCATTTCG-3' | 4 |
| OPR104<br>5'-GCGGCGACTAGTCCACTCCACAGTGATGGGGC-3' | 5 |
| OPR100<br>5'-GGGGGGGCCATGGCCGAAGACGACATTGAGGCCGAC-3' | 6 |
| OPR101<br>5'-GCGCGACTAGTCCAGTGTTTCAGAACCGGCTC-3'. | 7 |
| IADF100<br>5'-GGGGGGGATATCTCTCAGGCTGTTCACGCTG-3' | 8 |
| IADB100<br>5'-GGGGGGGTTCGAAAAGTGTACTTACGGGGGGCTGGAATCTCAGGTTC-3' | 9 |
| OPR145<br>5'-GGGGGGCTCGAGTATCAAAGAAGAACATGTGATCATC-3' | 10 |
| DR1A-B<br>5'-GCGGCGGGATCCGTTCTCTGTAGTCTCTGGGAGAGG-3' | 11 |
| OPR203000<br>5'-GATCCGAGGAAGAAGAGTACATGCCCATGGAACCCGGGTGAG-3' | 12 |
| OPR203001<br>5'-AATTCTCACCCGGGTTCCATCGGCATGTACTCTTCTTCCTCG-3' | 13 |
| DR2B-F<br>5'-CCCCCCGCTAGCGGAGGGGGCGGAAGCGGCGGAGGGGGGACA<br>CCCGACCACGTTTCCTGTGGCAGCCTAAGAGG-3' | 14 |
| DR2B-B2<br>5'-CCCCCCGAATTCCCCACTAGTCCATTCCACTGTGAGAGGGCTTGTC<br>AC-3' | 15 |
| MB201806<br>5'-GGGGGGGCCATGGCCTACGACGAGAACCCCGTGGTG-3' | 16 |
| MB175959<br>5'-GGGGGGGACTAGTTCGCCGCTGCACTGTGAAGC-3' | 17 |
| MB201807<br>5'-GGGGGGTATGCATACGACGAGAACCCCGTGGTG-3' | 18 |
| MB201808<br>5'-GGGGGGGACTAGTTCCACTTCGAGGAACTGTTTCC-3' | 19 |
| MB201809<br>5'-CCTCCTGGTCTCCTCTGTGAGTGG-3' | 20 |
| MB201810<br>5'-CCACTCACAGAGGAGACCAGGAGG-3' | 21 |
| OPR 215<br>5'-CCC CCC ACC GGT TAC GAC AAC CCC GTG GTG-3' | 22 |
| OPR 216<br>CCC CCC ATC GAT AAG TGT ACT TAC GTG GGA GAG GGC TTG GAG CAT-3' | 23 |

FIG. 10A

| | | |
|---|---|---|
| OVA 323-399<br>ISQAVHAAHAEINEAGR | | 26 |
| Gd-246-261<br>APYSTLLPPELSETP | | 27 |
| MBP (83-102) Y83<br>YDENPVVHFFKNIVTPRTPP | | 28 |
| 14 amino acid linker<br>TSGGGGSGGGGSSS | | 29 |
| EE TAG<br>EEEEYMPMEPG | | 30 |
| 24 amino acid linker<br>TSGGGGSGGGGSGGGGSGGGGSSS | | 31 |
| MBP (S4-102)<br>DENPVVHFFKNIVTPRTPP | | 32 |

FIG. 10B

SOLUBLE MHC COMPLEXES AND METHODS OF USE THEREOF

BACKGROUND OF THE INVENTION

1. Field of the Invention

The present invention relates to novel complexes of major histocompatibility complex (MHC) molecules and methods of expressing and use of such complexes. For example, in one aspect, the invention relates to MHC class II molecules that include a modified class II β2 chain. In another aspect, the invention relates to MHC class I and class II complexes that include a covalently linked immunoglobin constant region. In still other aspects, the invention relates to polyspecific MHC complexes, as well as methods of expressing and purifying MHC complexes. The MHC complexes of the invention are useful for a variety of applications including screening peptides for the capacity to modulate T-cell activity in vitro and in vivo.

2. Background

Antigen-specific T-cell responses are invoked by antigenic peptides. The peptides generally bind to the binding groove of MHCs as part of an immune system mechanism for identifying and responding to foreign antigens. The bound antigenic peptides interact with T-cell receptors and modulate an immune response. The antigenic peptides are bound by non-covalent means to particular "binding pockets" comprised of polymorphic amino acid residues.

Naturally-occurring MHC class II molecules are heterodimeric glycoproteins consisting of α and β chains. The α1 and β1 domains of these molecules fold together to form a peptide binding grove. Antigenic peptides bind the MHC molecule through interaction between anchor amino acids on the peptide and the α1 and β1 domains. Crystallographic analysis of human class II HLA-DR1 complex bound to an influenza virus peptide indicates that the N- and C-terminal ends of the bound peptide extend out of the binding groove such that the C-terminus of the peptide is proximal to the N-terminus of the β chain. See e.g., J. Brown et al., *Nature*, 364:33 (1993); L. Stern et al., *Nature*, 368:215 (1994)). MHC class I and class II molecules have different domain organizations. See e.g., A. Rudensky et al., *Nature*, 353:622 (1991). See also U.S. Pat. Nos. 5,284,935; 5,260,422; 5,194,425; 5,130,297; WO 92/18150; WO 93/10220; and WO96/04314 for discussions of MHC molecules.

Particularly, J. Brown, et al. supra have reported that the MHC class II β2 chain performs a critical role in the proper folding of MHC class II complexes.

The α and β chain transmembrane domains play an important role in the assembly and/or intracellular transport of MHC molecules. For example, amino acid changes in the TM domains can result in defective MHC molecules. The MHC α and β chain transmembrane and cytoplasmic domains have been disclosed. See P. Cosson et al., *Science*, 258:659 (1992); W. Wade et al., *Immunology*, 32:433 (1995); H. Kozono et al., *Nature*, 369:151 (1994) and J. Brown et al., supra.

MHC molecules complexed with antigenic peptides can induce selective immunosuppression by several different mechanisms. See e.g., J. Guery et al., *Critical Reviews in Immunology*, 13(3/4):195 (1993)).

More specifically, it has been reported that peptide-MHC complexes on the surface of antigen presenting cells (APCs) will only induce clonal expansion of a T-cell line specific for the MHC bound peptide if the antigen presenting cells also deliver co-stimulatory signals. One proposed approach takes advantage of this requirement for T-cell activation and reports inhibition of T-cell development by interaction with the antigenic peptide bound to the MHC molecule in the absence of co-stimulatory signals. See M. Nicolle et al., *J. Clin. Invest.*, 93:1361–1369 (1994); and S. Sharma et al., *Proc. Natl. Acad. Sci. USA*, 88:11465–11469 (1991).

Another proposed approach includes inhibiting T-cell development with MHC molecules that contain a bound peptide. The bound peptide can be an antagonist or partial agonist to a T-cell receptor (TCR). See B. Evavold et al., *Immunology Today*, 14(12):602–609 (1993).

Modifications of TCR-bound antigenic peptides have been attempted to examine residues responsible for specific T-cell responses. Determination of such "activating" amino acids of the antigenic peptides could provide insight into those amino acid sequences which can potentially play roles as TCR agonists or antagonists. See Evavold, B. et al., supra.

It also has been speculated that new vaccines might be developed based on determination of the nature of various antigenic peptides bound to MHC molecules. See R. Chicz et al., *Immunology Today*, 15(4):155–160 (1994).

Previous studies have shown that MHC class II heterodimeric molecules can bind exogenous peptide. However, the MHC class II chains often dissociate. In a dispersed state, the MHC class II chains may not be suitable for binding presenting peptide. See Stern, L. J. and D. C. Wiley, *Cell* 68: 465 (1992); Scheirle, A. B. et al., *J. Immunol.* 149: 1994 (1992); Kozano H. et al., *Nature* 369:151 (1994).

There have been several attempts to obtain fully soluble and functional MHC complexes. For example, in one approach, MHC complexes have been isolated from cells using biochemical techniques that include exposure to harsh agents such as proteolytic enzymes, salts, and/or detergents. These agents must often be removed by dialysis or binding reactions. See e.g., J. M Turner et al. *J. Biol. Chem.* 252: 7555 (1977); T. A. Springer et al. *PNAS* (USA) 73: 2481 (1976).

However, these methods are often not optimal for isolating fully soluble and functional MHC complexes in significant quantities.

Highly useful MHC class I and class II complexes capable of modulating the activity of T-cells and methods of making the complexes have been disclosed in a published PCT Application No. WO 96/04314, filed Jul. 31, 1995. The MHC complexes disclosed generally bind a specific peptide ligand.

SUMMARY OF THE INVENTION

The present invention relates to novel MHC class I and class II complexes that are fully soluble and functional, e.g., empty single chain MHC class II complexes, loaded single-chain MHC class II complexes, single chain MHC class II peptide fusion complexes, polyspecific single chain MHC class II complexes (empty, loaded, or including fused peptide) and uses of such complexes.

Generally stated, we have found that soluble expression of the MHC complexes can be facilitated by fusing an immunoglobin light chain constant region to the MHC complexes. We have also found that soluble expression of the MHC complex can be facilitated by modifying a class II β-chain of the MHC class II complex including deletion of the entire class II β-chain.

We previously disclosed highly useful single-chain ("sc-") MHC class I and class II complexes in the published PCT Application No. WO 96/04314 and in a published PCT application No. WO 97/28191, filed Jan. 31, 1996, the disclosures of which are each fully incorporated herein by reference. The disclosed sc-MHC class I and class II complexes include sc-MHC molecules with recombinantly fused presenting peptides (sc-MHC peptide fusion molecules), empty sc-MHC molecules (no recombinantly fused presenting peptides), and loaded sc-MHC complexes (include non-covalently attached presenting peptides).

We have discovered that it is possible to facilitate soluble expression of the previously disclosed sc-MHC class I and class II molecules by fusing an immunoglobin light chain constant region (i.e. Ig-$C_L$) and/or modifying the β2 chain in a class II sc-MHC molecule. The Ig-$C_L$ fusion includes adding a Ig-$C_L$ chain or suitable fragment thereof to the sc-MHC class I or class II complex. The class II β2 chain modification includes deleting, substituting or adding amino acids to the class II β2 chain, including deletion of the entire class II B2 chain. The Ig-$C_L$ fusions and class II β2 chain modifications enhance soluble expression of the sc-MHC molecules and do not significantly impact the specific binding activity of the sc-MHC molecules.

The invention further provides novel polyspecific MHC complexes. The complexes generally include one or more sc-MHC class I or class II molecules, one or more ligand binding molecules, one or more joining molecules and one or more optional effector molecules. As used herein, the term "ligand binding molecules" includes immunoglobins, immunoglobin-derived single-chain molecules and receptor ligands. The sc-MHC and ligand binding molecule portions of the complex are selected to specifically bind desired target structures and to provide potentially multiple binding specificities in one MHC complex. Soluble expression of fully functional polyspecific MHC complexes can be facilitated in a variety of cell types, if desired, by the Ig-$C_L$ fusions and/or class II β2 chain modifications discussed in detail below.

The term "MHC complexes of the invention" or related term is used herein to denote the sc-MHC class I and class II molecules disclosed herein and in the published PCT Application Nos. WO 96/04314 and WO 97/28191, which sc-MHC molecules include a modified class II β2 chain and/or a fused Ig-$C_L$ chain or suitable Ig-$C_L$ chain fragment as provided herein. The term is also meant to embrace the polyspecific MHC complexes provided, either with or without the modified class II β2 chain and/or the fused Ig-$C_L$ chain or Ig-$C_L$ chain fragment.

The MHC complexes of the invention have numerous uses in vitro and in vivo.

For example, the MHC complexes of the invention can be used to detect and analyze a variety of ligands such as peptides. Particularly, the MHC class II complexes can also be used as provided for diagnostic purposes such as for the detection of T-cells with pathogenic properties. The MHC complexes can additionally be employed in functional, cellular and molecular assays, and in structural analysis, including X-ray crystallography, nuclear magnetic resonance imaging, computational techniques such as computer graphic display. Significantly, the single-chain format and enhanced soluble expression of the MHC complexes is expected to simplify several aspects of data collection and analysis. The MHC complexes can also be used in screens to identify and isolate TCR and/or MHC agonists and antagonists, particularly small molecules that inhibit interaction between naturally-occurring TCRs and MHC complexes. Additionally, a variety of known techniques can be used to screen for small molecules that potentially block interaction between an MHC complex of the invention and a TCR or MHC complex-specific antibody.

The MHC complexes of the invention have significant uses in vivo. For example, the complexes can be employed to compete with pathogenic antigen presenting cells (APCs) such as those implicated in an immune-related disorder or disease; or to immunize mammals, e.g., humans, against MHC structures such as extracellular regions that occur on the surface of APCs and which perform or help other molecules perform pathogenic or otherwise harmful functions. Particularly, the MHC class II complexes of the invention can be used to raise antibodies according to known immunological methods such as those described below. The antibodies produced by the methods that can be used in therapeutic strategies designed to modulate immune responses in vivo, e.g., by inhibiting or reducing numbers of specific APCs that recognize a desired antigen. Particularly, monoclonal antibodies can be selected that specifically bind MHC epitopes so that a restricted APC subset or population implicated in an immune disorder or disease or other pathology can be targeted and preferably eliminated. As will be described more fully below, the APCs or antibodies binding same can be unmodified, or if desired, can be covalently linked to drugs, toxins, radionuclides or other agents such as enzymes.

Additionally, the MHC complexes of the invention can be used to screen immune cells such as T-cells expressing a desired target structure in vitro. It has been useful in several settings to obtain and expand selected T-cells expressing target structures such as cell receptors glycoproteins, lipoproteins, lipids, glycolipids and carbohydrates. Significantly, a single polyspecific MHC complex of the invention can be used to select-cells expressing multiple target structures.

As used herein, the term "presenting peptide" refers to a peptide that is capable of modulating the activity of a T-cell receptor, either to induce T-cell proliferation, to inhibit or inactivate T-cell development such as determined by the assays disclosed below, including the assay that includes sequential steps of culturing T-cells to proliferate same, and contacting the T-cells with an MHC complex of the invention (with fused or non-covalently bound peptide(s)) and then evaluating whether the complex inhibits further development of the T-cells.

The term "empty", as used herein, refers to an MHC complex of the invention which lacks a covalently or non-covalently bound presenting peptide. Exemplary empty MHC complexes include empty class II MHC complexes comprised of a single polypeptide chain, rather than a complex of polypeptides. Another illustrative empty MHC complex is an empty polyspecific class II MHC complex comprising one or more sc-MHC class II molecules comprising fused polypeptide. The empty MHC complexes include a peptide binding groove or cleft capable of specifically binding a peptide.

The term "loaded", as used herein, refers to an empty MHC complex of the invention which includes a presenting peptide non-covalently bound to the peptide binding groove or cleft of the MHC complex. The non-covalent binding is suitably via stable hydrogen bonding between the presenting peptide and the peptide binding groove or cleft of the empty MHC complex. The non-covalent binding can be performed in vitro or in vivo. An example of a loaded MHC complex is a loaded sc-MHC class II complex comprised of a single polypeptide chain, rather than a complex of polypeptides.

The MHC complexes of the invention provide significant advantages. For example, as noted above, the modified class II β2 chain and/or Ig-$C_L$ chains provided facilitate soluble expression of the complexes. Accordingly, production and use of the MHC complexes is positively impacted. In addition, with respect to the MHC complexes comprising a desired presenting peptide (loaded, or covalently linked), prior practice required the purification of loaded MHC molecules from antigen presenting cells. Such loaded peptides were generally tightly bound and could not be efficiently exchanged with a peptide of interest. In contrast, the MHC complexes can contain single antigenic peptides that can be readily isolated from expressing cells in significant quantities. Analysis of interactions with T-cell receptors will be facilitated by use of such MHC complexes. Additionally, a wide variety of the peptides can be presented for interaction with T-cells by virtue of the fact that only a small number (ca. 4 to 6) of amino acids in the peptide are important for binding to a particular MHC molecule. That is, a library of different peptides can be linked to the MHC molecule for presentation of T-cells.

The MHC complexes of the invention provide further advantages. For example, the polyspecific MHC complexes are capable of specifically binding more than one target structure thereby providing means to detect cells expressing multiple target structures with a single complex. Because the polyspecific MHC complexes can include multiple binding sites, binding strengths can be enhanced. Moreover, the modest size of many polyspecific MHC complexes (e.g., those less than about 50–70 kDa), makes them potentially more useful than whole antibodies for a variety of applications such as imaging cells and delivering desired small molecules to the cells such as drugs, toxins or radionuclides.

The polyspecific MHC complexes of the invention have additional uses and advantages. For example, in accordance with the invention, it is possible to combine single chain portions of polyspecific MHC complexes in vitro under controlled conditions of temperature, concentration, buffer conditions etc. Particularly, the single chains of multi-chain polyspecific MHC complexes can be combined to produce novel homo- or heterodimeric polyspecific MHC complexes. The complexes produced can be purified, if desired, by one or a combination of standard techniques such as those specifically provided below. Alternatively, the single-chains of the polyspecific MHC complexes can be combined in situ, i.e., in cultured cells, and purified from those cells as described below.

The MHC complexes of the invention provide still further advantages. For example, empty class I or class II MHC complexes can be used in screens to identify peptides recognized by a naturally-occurring TCR. Additional advantages of the MHC complexes include use in methods for suppressing an immune response (e.g. treatment of individuals with immune disorders such as autoimmune disorders or allergies) and methods for inducing a desired immune response, e.g., where a mammal is or is likely to become immunocompromised, e.g., where the immune system is suppressed by viral infection (e.g., as in AIDS) or chemotherapy (e.g., as in radiation therapy to treat cancer), and diagnostic methods such as HLA typing and in vivo diagnostic imaging. Direct administration of a DNA construct coding for a MHC peptide fusion complex is also contemplated.

Empty MHC molecules of the invention provide particular advantages. For example, empty sc-MHC or polyspecific class II molecules can be readily combined with various suitable presenting peptides to form loaded MHC molecules. The ability to conveniently load empty MHC molecules of the invention enables the screening of many presenting peptides to evaluate the ability of each presenting peptide to modulate T-cell receptor activity.

A polyspecific MHC complex of the invention generally includes one or more sc-MHC class I or class II molecules (the same or different) up to about two to five of such molecules. In accord with the present invention, the sc-MHC molecules can include a modified β2 class II chain and/or a fused Ig-$C_L$ chain or suitable Ig-$C_L$ chain fragment to facilitate soluble expression of the complex. Exemplary polyspecific MHC complexes include class II complexes comprising one sc-MHC class II molecule sometimes comprising a modified β2 class II chain. Additionally, chimeric polyspecific MHC complexes comprising one or more sc-MHC molecules of known classes ($IA^d$, DR1, DR2, DP, IE, QP, etc.) are also within the scope of the present invention.

The structure of preferred sc-MHC molecules (class I and II) have been fully disclosed in the published PCT application Nos. WO 96/04314 and WO 97/28191.

Briefly stated, the previously disclosed sc-MHC class I and class II molecules can be empty, loaded or can include a fused or loaded presenting peptide as desired. For example, a sc-MHC class II molecule can have a presenting peptide covalently linked to the MHC α or β chain. Typically, the presenting peptide is linked to the N-terminus of the α or β chain via a peptide linker. The sc-MHC molecule will generally be truncated (particularly, not including all of a transmembrane portion), or if desired, it may in some instances be "full-length" and include a transmembrane portion, or portions thereof, and a cytoplasmic domain, or portions thereof. The sc-MHC molecule may also include what is sometimes referred to in the field as a "hinge" portion adjacent to the transmembrane domain. See Kabat, G. A. et al. infra.

In cases where it is desired to obtain fully soluble MHC complexes, the sc-MHC class II molecule will generally not include all of the transmembrane portion although suitable fragments thereof (e.g. 1 to 5 amino acids) can be included provided that the single chain molecule is fully functional and soluble. Preferred sc-MHC class II molecules will include the β2 class II modifications and/or the Ig-$C_L$ chain or Ig-$C_L$ chain fragment fusions provided below. In instances where it is desired to increase solubility and to assist purification of an MHC complex, or add to a cleavage site, a suitable protein tag such as those disclosed below can be added to the MHC complex.

As disclosed in the PCT application Nos. WO 96/04314 and WO 97/28191, sc-MHC molecules including a fused presenting peptide generally also include a flexible linker sequence interposed between the MHC chain and the presenting peptide. The linker sequence desirably allows effective positioning of the presenting peptide with respect to the MHC binding groove so that the presenting peptide can modulate the activity of a T-cell receptor, either to induce T-cell proliferation or to inhibit or inactivate T-cell development. The T-cell activities can be determined by a variety of in vitro and in vivo assays including those disclosed below. Exemplary assays are those in vitro assays that include sequential steps of culturing T-cells to proliferate, and contacting the T-cells with the MHC peptide fusion complex and then evaluating whether the MHC complex inhibits further development of the T-cells.

As further disclosed in the PCT application Nos. WO 96/04314 and WO 97/28191, with respect to sc-MHC molecules including a peptide fusion, the MHC α and β chain sub-units are linked as a single chain fusion protein and the presenting peptide is typically linked to the β chain of the fusion protein. Such a linked single-chain complex can provide a number of advantages. In particular, in reducing the complex to a single molecule, yields and stability of the molecules are typically enhanced. That can be especially important for soluble molecules which may not be produced efficiently in active form. As will be discussed more fully below, yield of the sc-MHC molecules is further enhanced by the class II β2 chain modifications and/or Ig-$C_L$ chain or Ig-$C_L$ chain fragment fusions disclosed below.

As will be disclosed in more detail below, the MHC complexes of the present invention include sc-MHC molecules that can comprise a variety of class I (H-2 or HLA) or class II (IA, IE, DR, DQ, or DP) MHC molecules. Exemplary MHC chains include those associated with an immune response such as in an allergy or autoimmune response. Other examples have been disclosed in the published PCT Application Nos. WO 96/04314 and WO 97/28191.

As noted, we have surprisingly found that the MHC class II complexes of the invention exhibit enhanced soluble expression and are capable of specific binding when the class II β2 chain is modified and particularly deleted. The class II β2 chain can be, e.g., a IA, IE, DR, DQ or DP chain of known DNA sequence.

In one illustrative embodiment of the present invention, an MHC complex of the invention includes a sc-MHC class II molecule in which at least one amino acid of the β2 class II chain has been deleted. The deleted amino acids can be contiguous or non-contiguous essentially up to the full-length β2 class II chain.

In another illustrative embodiment, the MHC complex includes one or more amino acid additions or substitutions in the class II β2 chain. Particularly contemplated are those amino acid substitutions in the class II β2 chain which minimize or eliminate cross-linking between Cys residues. The substitutions can be contiguous or non-contiguous up to essentially the full-length class II β2 chain.

As discussed above, we have also found that fusion of an Ig-$C_L$ chain to a sc-MHC complex facilitates soluble expression of that complex. Thus in one illustrative embodiment, an MHC complex of the invention includes a sc-MHC molecule fused to an Ig-$C_L$ chain. The Ig-$C_L$ chain can be fused to the single-chain MHC β or α chain directly or indirectly through a suitable peptide linker sequence.

The Ig-$C_L$ chain can obtained from a κ- or λ-type immunoglobin light chain constant region of known DNA sequence. The κ-type Ig-$C_L$ chain is often referenced herein as "Cκ chain", whereas the λ-type Ig-$C_L$ chain is often be referred to as "Cλ chain".

Further provided are MHC complexes of the invention that include a suitable Ig-$C_L$ fragment fused to a desired sc-MHC molecule. The fragment can include one or more amino acid deletions of a desired full-length Cκ or Cλ chain. The one or more deleted amino acids can be contiguous or non-contiguous essentially up to the full-length Cκ or Cλ chain.

The invention further provides MHC complexes of the invention comprising a fused Ig-$C_L$ chain in which at least one amino acid has been substituted. The substitutions can be contiguous or non-contiguous up to essentially the full-length Cκ or Cλ chain. The Ig-$C_L$ chain may also include one or more amino acid additions as desired.

As mentioned above, an MHC complex of the invention fused to a Ig-$C_L$ chain or suitable Ig-$C_L$ chain fragment can also include a modified class II β2 chain, as desired, to enhance soluble expression.

The present invention thus provides a variety of class II MHC complexes that can include class II β2 chain modifications and/or fusions of the Ig-$C_L$ chain (or suitable fragment) that facilitate soluble expression of the MHC complex and maintain specific binding activity of the complex.

The present invention also features polyspecific MHC complexes. The polyspecific complexes generally includes one more sc-MHC class I or class II molecules, one or more ligand binding molecules and one or more optional effector molecules. The complex further includes one or more covalently or non-covalently linked joining molecules. The order of each component is not important so long as each component provides function for which it was intended.

More particularly, in one embodiment, a polyspecific MHC complex includes multiple chains linked by the joining molecules. For example, one chain can comprise an sc-MHC class II molecule fused to a first joining molecule and an optional effector molecule. The first joining molecule can be either covalently or non-covalently linked to a second joining molecule which further is linked to the ligand binding molecule and an optional effector molecule. The first and second joining molecules are linked together by covalent or non-covalent bonds (e.g. hydrogen bonds).

In another embodiment of the invention, a polyspecific MHC complex consists of a single chain. For example, the chain can comprise a sc-MHC class II molecule covalently linked to a ligand binding molecule and an optional effector molecule. Thus, the term "polyspecific" refers to single and multi-chain molecules consisting of a single MHC complex comprising potentially multiple binding specificities.

The term "joining molecule" as used herein in reference to a polyspecific MHC complex of the invention refers to a protein or polypeptide that is capable of specifically binding and forming a specific binding pair, either covalently (e.g., by disulfide bonding) or non-covalently by hydrogen bonding with another protein or polypeptide. Typically, a molecule which is specifically bound by the joining molecule is sometimes referred to herein as a second joining molecule, which second joining molecule is the same as, or is different from, the (first) joining molecule. Exemplary joining molecules include immunoglobin constant chains (H or L) or suitable fragments thereof, as well as coiled-coil and helix-turn-helix motifs such as those described more fully below. Particularly, an Ig-$C_L$ chain or suitable Ig-$C_L$ chain fragment is one type of joining molecule.

The term "effector molecule" as used herein in reference to a polyspecific MHC molecule of the invention refers to a molecule comprising an epitope capable of specifically binding an antibody (polyclonal, monoclonal or chimeric). Typically, the antibody will be a monoclonal antibody. The term is also meant to include a cell toxin, receptor ligand, drug, radionuclide, or a protein "tag" such as the well-known myc, 6xHIS or EE tags. Exemplary tags have been disclosed in the published PCT Application Nos. WO 96/04314 and WO 97/28191. As will be more apparent from the disclosure that follows, in some cases a joining molecule can be an effector molecule (e.g., an Ig-$C_L$ chain or fragment) as provided herein.

A subunit of a polyspecific complex can be linked to another subunit, sometimes through a suitable peptide linker, as desired. By the term "subunit" is meant that unitary portion of the polyspecific MHC complex that consists of, e.g., a sc-MHC molecule, ligand binding molecule, or effector molecule. The subunits are generally linked to each other in a sequential order that is selected in accord with intended use. A suitable peptide linker can be employed to space the subunits as desired to provide increased flexibility between the subunits. Exemplary peptide linker sequences and assays to test functionality of the peptide linker sequences are disclosed below.

The invention also pertains to a nucleic acid segment (RNA, mRNA, cDNA or genomic DNA) comprising a sequence encoding an MHC complex of the invention. Methods for obtaining DNA segments encoding a variety of sc-MHC class I and class II complexes have been disclosed in the published PCT Application Nos. WO 96/04314 and WO 97/28191.

Briefly stated, nucleic acid encoding an sc-MHC class I or class II molecule of interest can be obtained from a variety of sources including polymerase chain reaction (PCR) amplification of publicly available MHC chain sequences. In accordance with the present invention, the nucleic acid segment may include a β2 class II chain modification and/or a fused Ig-$C_L$ chain or suitable Ig-$C_L$ chain fragment that facilitates expression of fully soluble and functional complex. In most instances, the nucleic acid segment is inserted into a DNA vector (i.e., DNA expression vector) capable of expressing the MHC complex in a desired cell, typically a eukaryotic or prokaryotic cell. The nucleic acid segment can include or be fused to operably linked control elements such as a promoter, leader and/or optional enhancer sequences, to augment expression of the MHC complex in the cell. Alternatively, the nucleic acid segment can be optimized for use in a cell-free translation system if desired in accordance with known methods.

As will become more apparent from the discussion that follows, in some cases, a nucleic acid segment or DNA vector carrying same will encode only a portion of an MHC complex of the invention. For example, some of the polyspecific MHC complexes provided are multi-chain molecules which can be expressed from one or more than one DNA vector. An expressed single-chain encoded by a DNA vector can be combined with another expressed single-chain in vitro or in situ (i.e. in cells) to form a complex. For example, the polyspecific MHC complex can be made by introduction of multiple nucleic acid segments or DNA vectors carrying same into suitable cells and expressing the complex. The polyspecific MHC complex is then assembled in the cell via translation, processing and assembly pathways. Alternatively, the single-chains of the complex can be separately harvested and combined in vitro under controlled conditions e.g., by a dialysis reaction.

In general, a nucleic acid segment in accord with the invention is made to minimize occurrence of naturally-occurring MHC control elements. By the term "control elements" is meant those known nucleic acid sequences which influence transcription, translation, and/or processing of a desired protein. In most instances, protein expression will be driven by pre-determined transcriptional control elements operably linked to the nucleic acid segment including a promoter, optional enhancer element and leader sequence. In accord with one aspect of the invention, the Ig-$C_L$ chain or suitable Ig-$C_L$ chain fragment is linked to the nucleic acid segment and will sometimes include intron and exon sequence from the Ig-$C_L$ chain, e.g., where the MHC complex is expressed in a cell type that can perform RNA splicing. In cases where it is desired to express the MHC complex in a prokaryotic cell, the introns can be removed. As will be discussed more fully below, a variety of Ig-$C_L$ chains or suitable fragments thereof can be fused to the MHC complexes to facilitate soluble expression.

The present invention also provides methods of obtaining substantial quantities of fully soluble and functional MHC complexes. Generally stated, the methods include expressing the MHC complexes in suitable cells, culturing the cells, and purifying the complexes therefrom (if desired) to obtain substantially pure MHC complexes. As noted earlier, in the case of some polyspecific complexes, it will be desirable to combine MHC single-chains in vitro or in situ to facilitate production of desired complexes. The methods can be used to express and purify a desired MHC complex on a large-scale (i.e. in at least milligram quantities) from a variety of implementations including roller bottles, spinner flasks, tissue culture plates, bioreactor, or a fermentor. Significantly, the isolation and purification methods of the invention are positively impacted by the class II β2 chain modifications and/or Ig-$C_L$ chain or Ig-$C_L$ chain fragment fusions provided.

The present methods for isolating and purifying the MHC complexes of the invention are highly useful. For example, for an MHC complex exhibiting a desired binding activity or potentially multiple binding activities (e.g., suppression of immunoreactive T-cells in vitro or in vivo or specific binding to desired immune cells), it is highly useful to have methods for expressing and purifying the MHC complexes. It is particularly useful to have methods that can produce at least milligram amounts of the desired MHC complexes, e.g., so that the MHC complex can be made as one component of a kit suitable for medical, research, home or commercial use. Further, it is useful to have large-scale quantities of the MHC complexes available to simplify structural analysis, as well as for further purification and/or testing if desired.

The purification methods of the present invention generally include chromatographic approaches that can be tailored to purify a desired MHC complex from cell components which naturally accompany it. Typically, the approaches involve specific binding of a subunit of the MHC complex. Significantly, several strategies can be employed to purify the polyspecific MHC complexes disclosed herein including chromatographic approaches designed to select one or more of the sc-MHC molecules, ligand binding molecules, joining molecules, effector molecules and fused Ig-$C_L$ chain or Ig-$C_L$ chain fragment.

The invention also features in vitro screens to detect peptides recognized by naturally-occurring MHC complexes, including peptides that can induce T-cell development as well as peptides that can antagonize naturally-occurring MHC complexes such as MHC antagonists or partial agonists.

The present invention also provides methods for suppressing an immune response in a mammal, particularly a human, that comprises administering to the mammal an effective amount of an MHC complex of the invention, e.g., a sc-MHC class II peptide fusion complex, loaded sc-MHC class II complex polyspecific class II peptide fusion, loaded polyspecific class II peptide fusions, complex, etc. The methods of the present invention include treatment of a mammal that suffers from or is susceptible to an autoimmune disorder such as multiple sclerosis, insulin-dependent diabetes mellitus or rheumatoid arthritis or, alternatively, a mammal who is susceptible to undesired immune response(s) such as a subject with chronic allergies or a patient undergoing transplant surgery such as organ or skin transplant surgery.

An immune response may be suppressed in accordance with the invention by one or a combination of alternative strategies. Specifically, anergy or apoptosis of T-cells may be induced by the administration of an effective amount of one or more of the MHC complexes of the invention in the absence or near absence of co-stimulatory signal(s). Typically, the MHC complex does not contain an intact transmembrane domain of a full-length MHC molecule, or portions thereof.

Also provided are methods for suppressing an immune response in a mammal which includes administering an effective amount of a DNA segment (or vector carrying same) that encodes an MHC complex of the invention. As mentioned earlier, in cases where it is desired to use a DNA segment encoding a polyspecific MHC complex of the invention including multiple chains, it will often be useful to administer an effective amount of two or more DNA sequences encoding each of the chains. Typically, co-expression and assembly of the encoded proteins in vivo or in vitro forms the polyspecific MHC complex. It also may be desirable in some situations to administer one or more DNA sequences encoding an MHC complex along with a gene encoding a suitable T-cell stimulatory factor such as, e.g., CD80 or CD86. As used herein, the term "T-cell co-stimulatory factor" refers to a peptide that is capable of providing a co-stimulatory signal to thereby activate T-cell proliferation in the presence of one or more MHC fusion complexes. Such activation of T-cell proliferation can be determined by the assays disclosed herein.

Further provided are diagnostic methods including HLA typing and in vivo diagnostic imaging using the MHC complexes of the invention including MHC complexes that have been modified to include a radionuclide (e.g., $^{125}$I, $^{32}$P or $^{99}$Tc) or other detectable tag.

The invention also includes methods for the detection and purification of immune cells such as T-cells by use of the MHC complexes disclosed herein. Cells such as T-cells which specifically bind the MHC complex can then be substantially separated from cells which do not according to known methods (e.g., flow cytometry, immunopanning) sufficient to prepare a substantially pure population of T-cells. Such T-cells are useful in several clinical and research settings such as, e.g., immune system reconstitution of immunocompromised patients, and in vitro screens for detecting presenting peptides associated with undesired immune reactions.

BRIEF DESCRIPTION OF THE DRAWINGS

FIGS. 4A and 4B are drawings of sc-MHC class II fusion peptide fusions comprising (4A) IA$^d$ and (4B) DR-2 chains. Abbreviations used are as follows: SP, signal peptide sequence; PEP, fused antigenic peptide sequence; L1, 10 amino acid linker; L2, amino acid linker; EE, antibody tag;

IgG-C$_L$, immunoglobin light chain constant region, αTM C$_y$, cytoplasmic transmembrane domain. Corresponding empty molecules would be represented by the same drawings except that the sequence "PEP" would be omitted. Loaded molecules would have "PEP" sequence non-covalently associated with the sc-MHC class II binding groove.

Figure 5A:
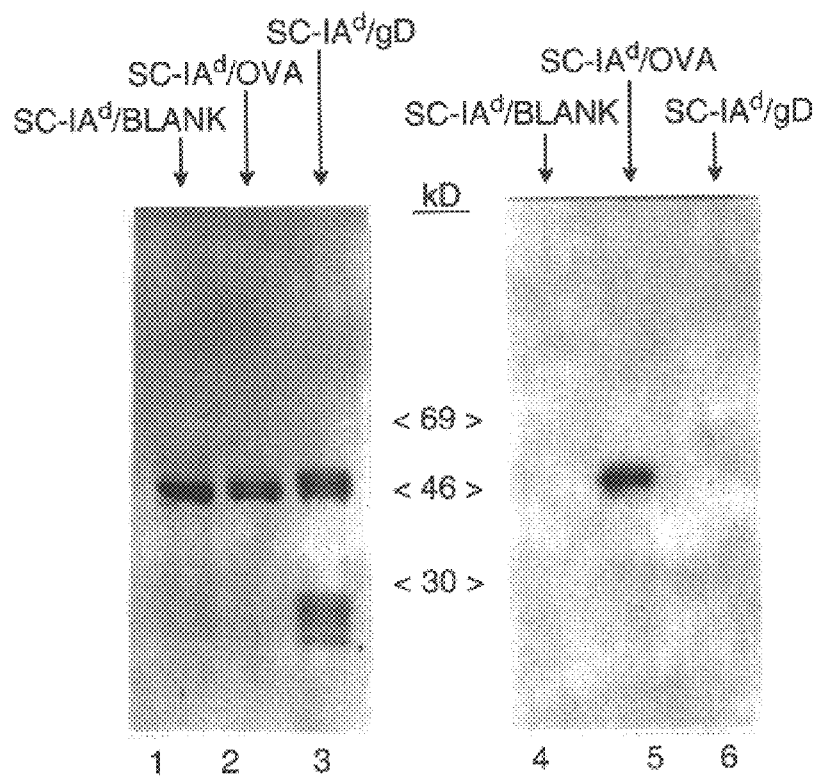
Figure 5B:
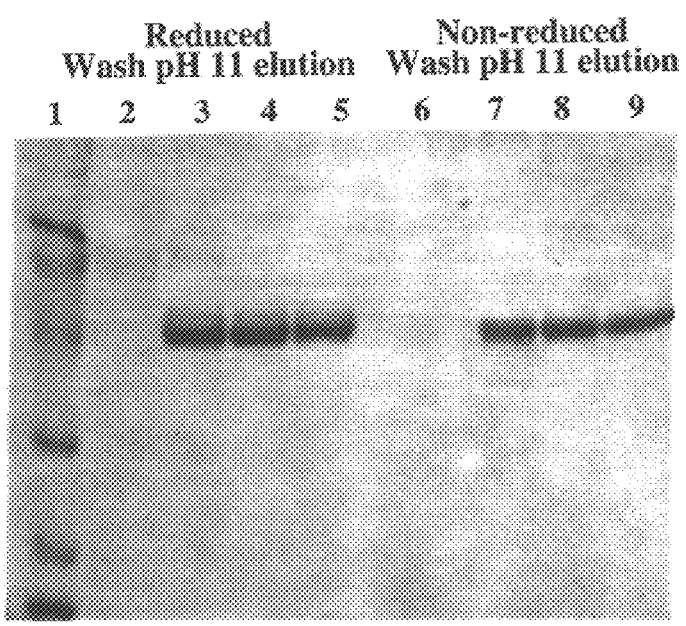

FIGS. 5A and 5B are polyacrylamide gels or immunoblots showing the expression of soluble single-chain MHC class II/peptide protein. FIG. 5A shows the sc-IA$^d$ samples (lanes 1–3) analyzed by 12% SDS-PAGE and stained with Coomassie Blue. Migration of molecular weight standards are indicated. The sc-class II proteins (lanes 4–6) were also transferred to nylon membrane ad probed with mouse antisera specific to the OVA 323–339 peptide. FIG. 5B shows anti-DR affinity purification profile of the scDR2Δβ2 samples analyzed by 10% SDS-PAGE. The affinity purified protein is shown in lanes 3–5 (reducing conditions) and lanes 7–9 (non-reducing condition).

Figure 6A:
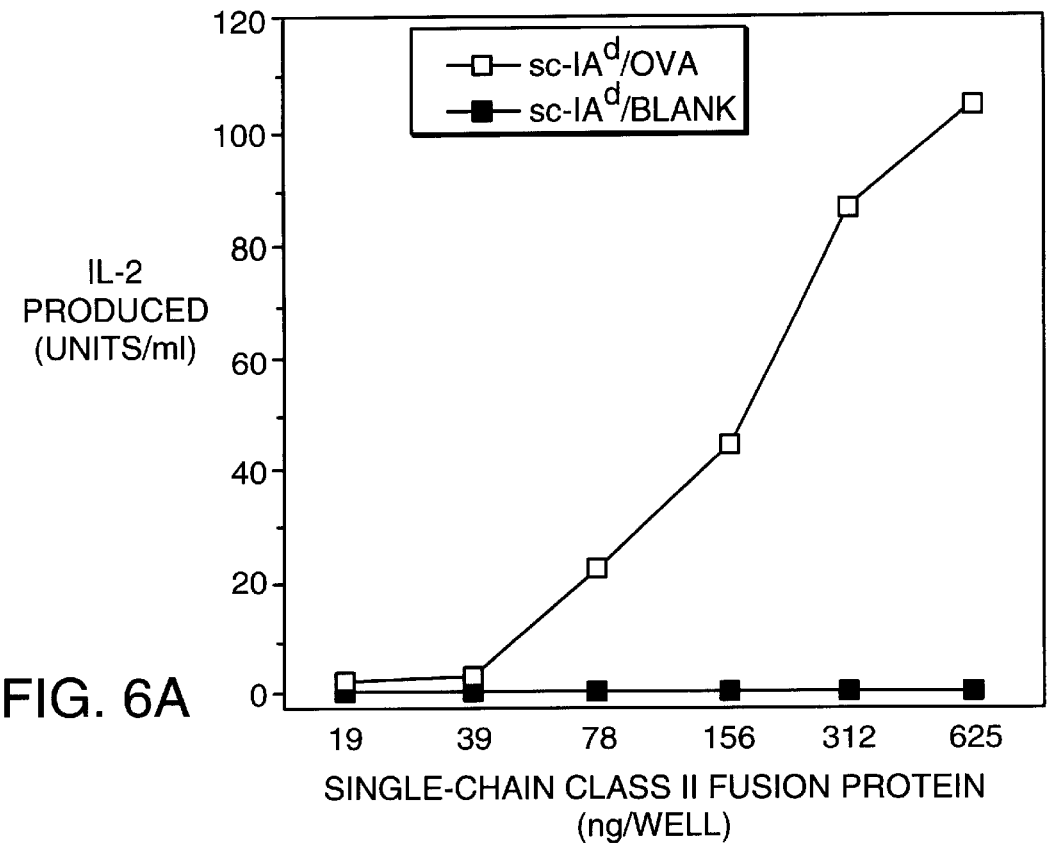
Figure 6C:
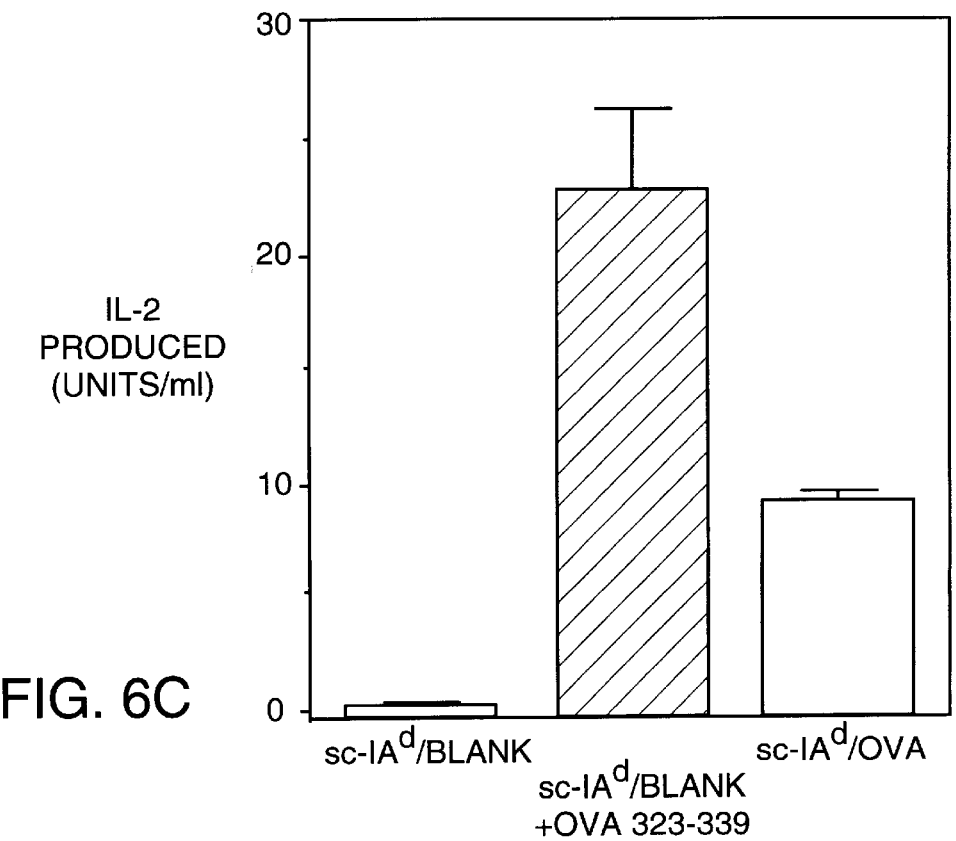
Figures 2, 6B:
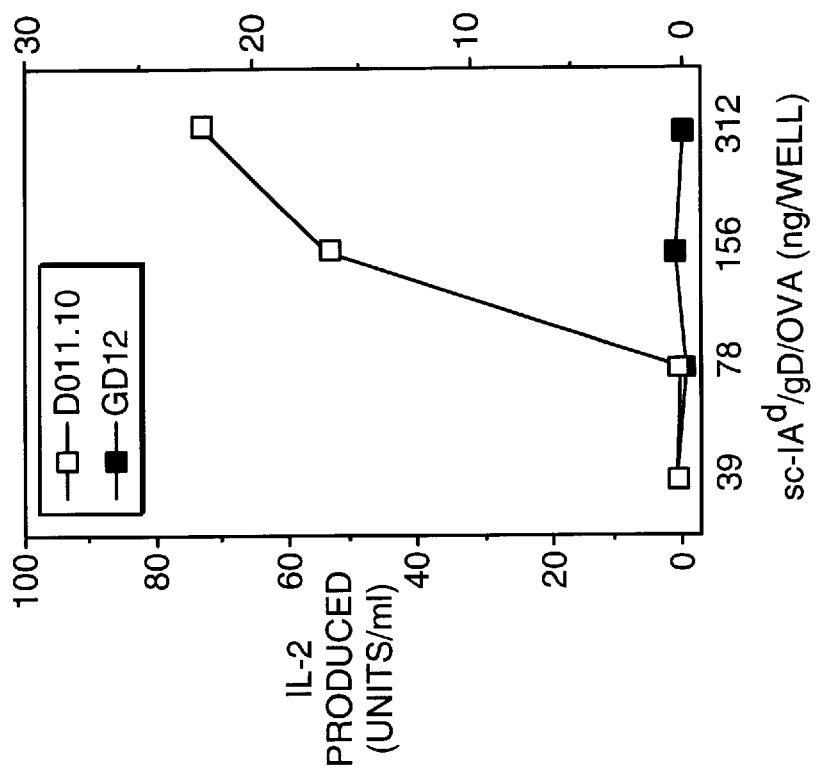

FIGS. 6A–C are graphs illustrating that single-chain class II/peptide proteins specifically activate T-cell responses. FIG. 6A shows DO11.10 T-cell hybridomas specific for OVA 323–339 bound to IA$^d$ were stimulated to produce Il-2. FIG. 6B shows two different T-cell hybridomas, GD12 (specific to gD 246–261 and IA$^d$) or DO11.10, were stimulated to secrete IL-2 in a presenting peptide specific manner. FIG. 6C shows immobilized sc-IA$^d$/blank protein with OVA peptide or sc-IA$^d$/OVA fusion protein (but not blank fusion proteins) stimulated release of IL-2 from DO11.10 cells.

Figure 7:
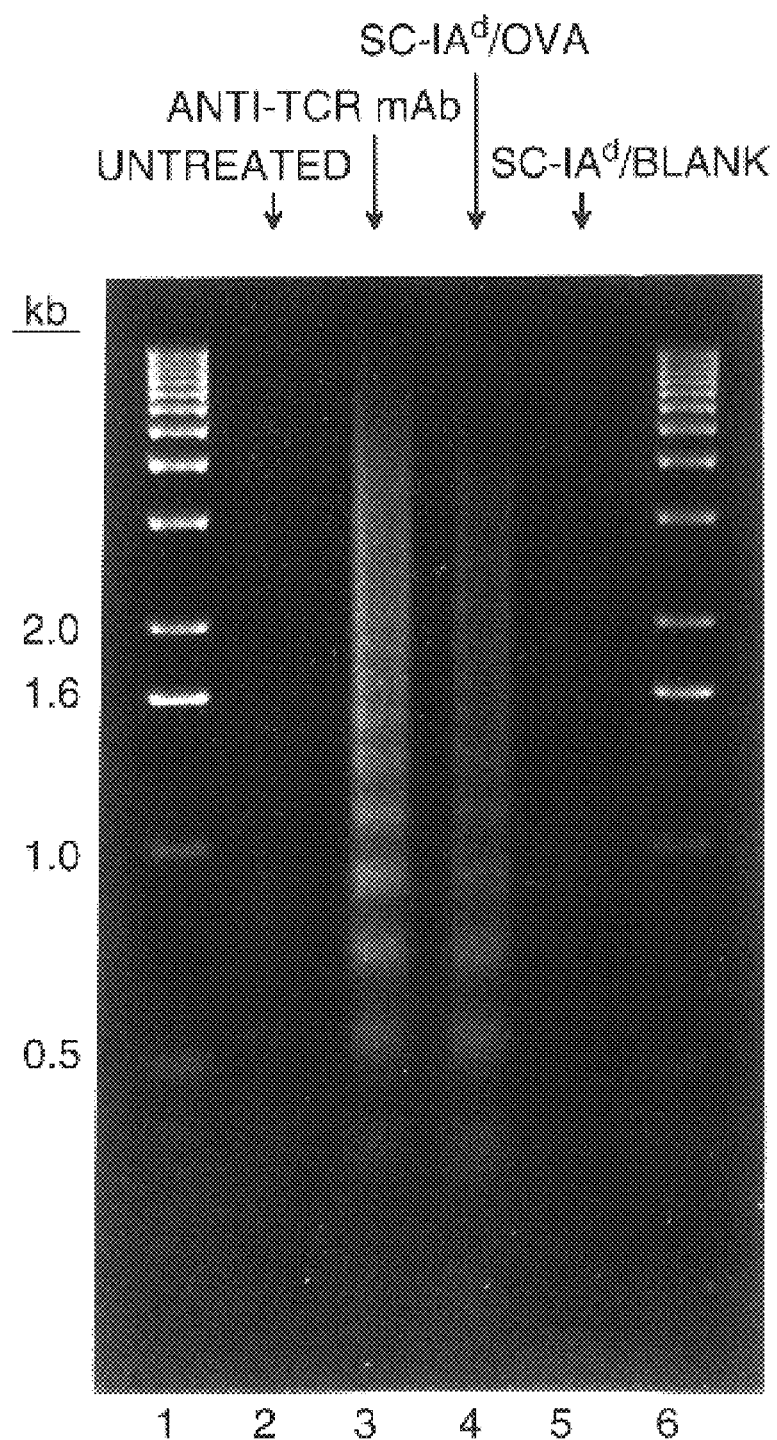

FIG. 7 is a photograph of an ethidium bromide stained gel showing that anti-T-cell receptor antibody (anti-TcR mAb) or sc-IA$^d$/OVA can induce T-cell apoptosis. The nucleosome ladder in lanes 3 and 4 is indicative of apoptosis.

Figure 8A:
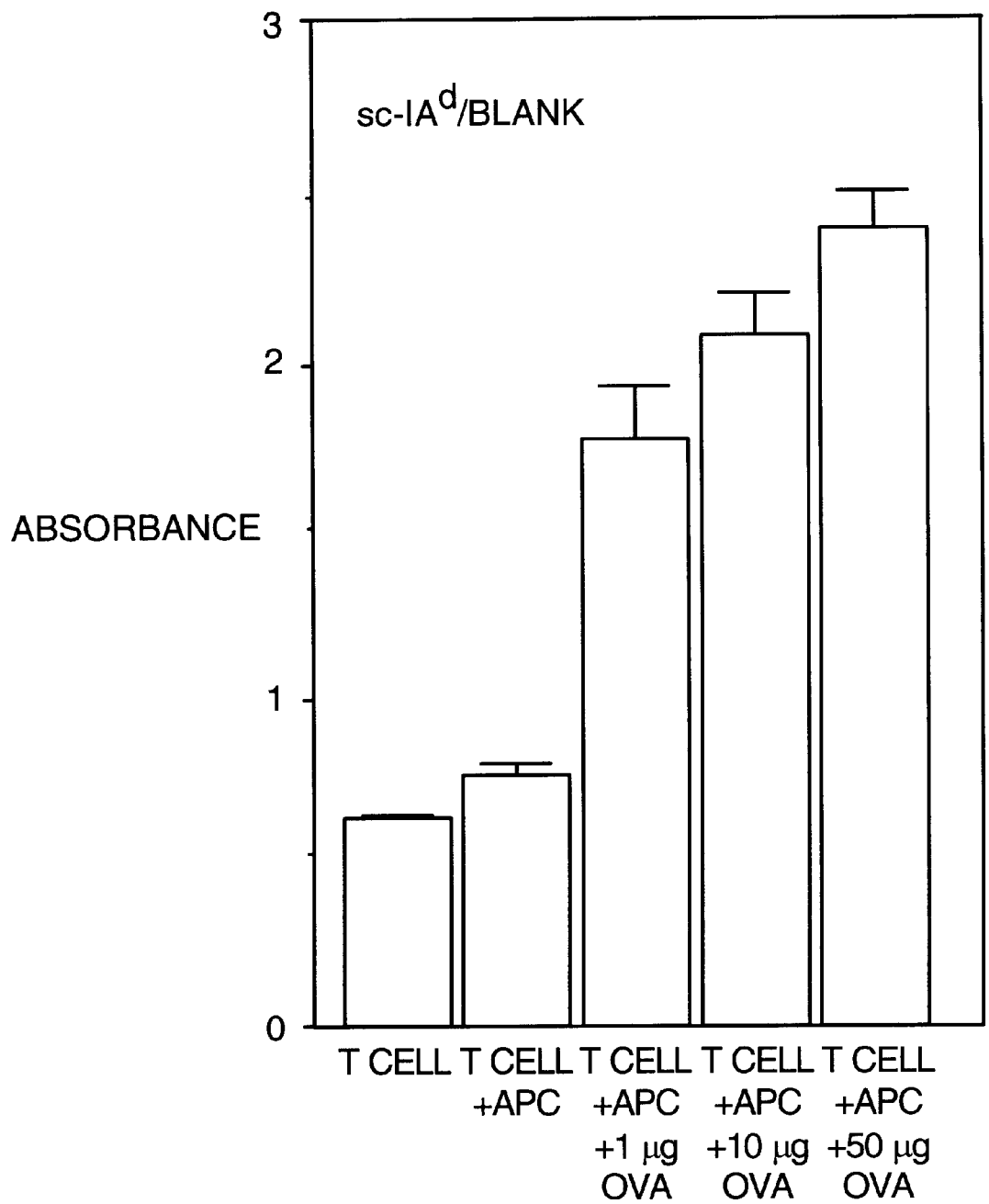
Figure 8B:
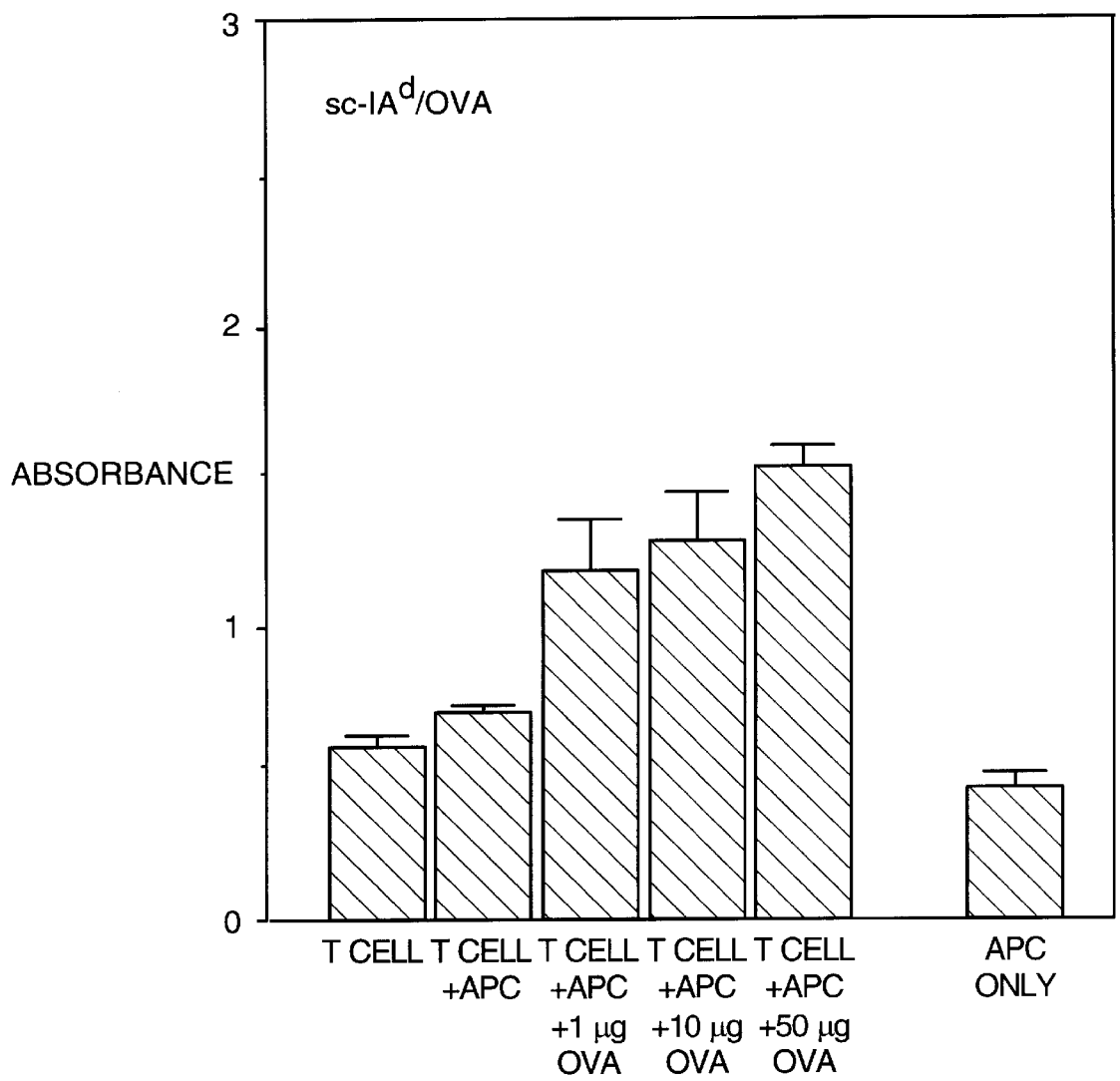

FIGS. 8A and 8B are graphs demonstrating that in vivo expression of SC-IA$^d$/OVA suppresses T-cell clonal expansion.

Figure 9A:
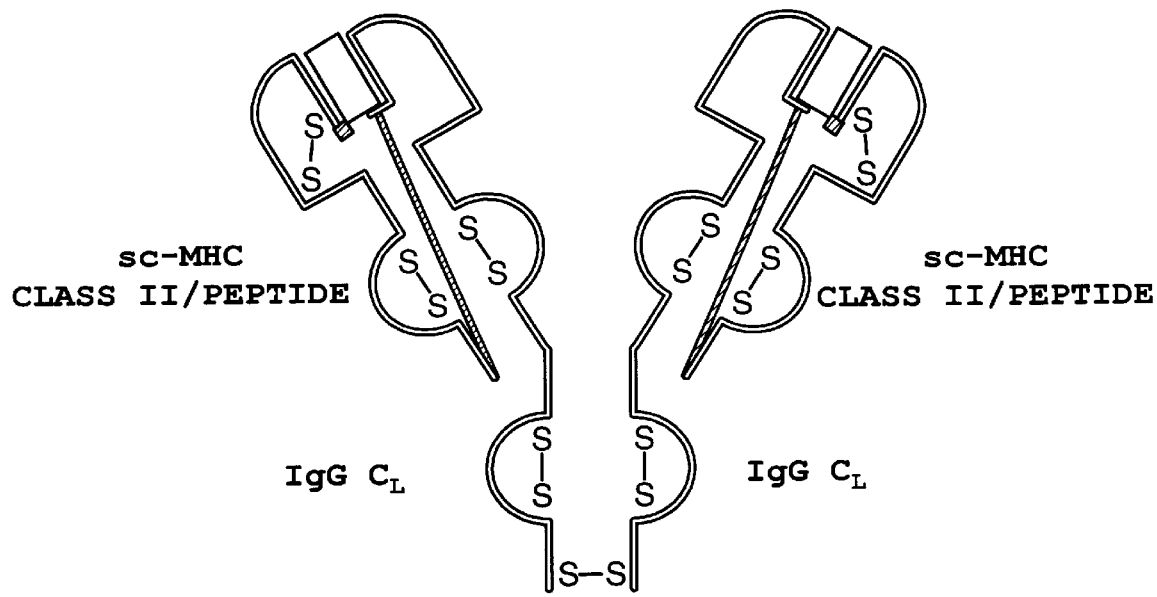
Figure 9B:
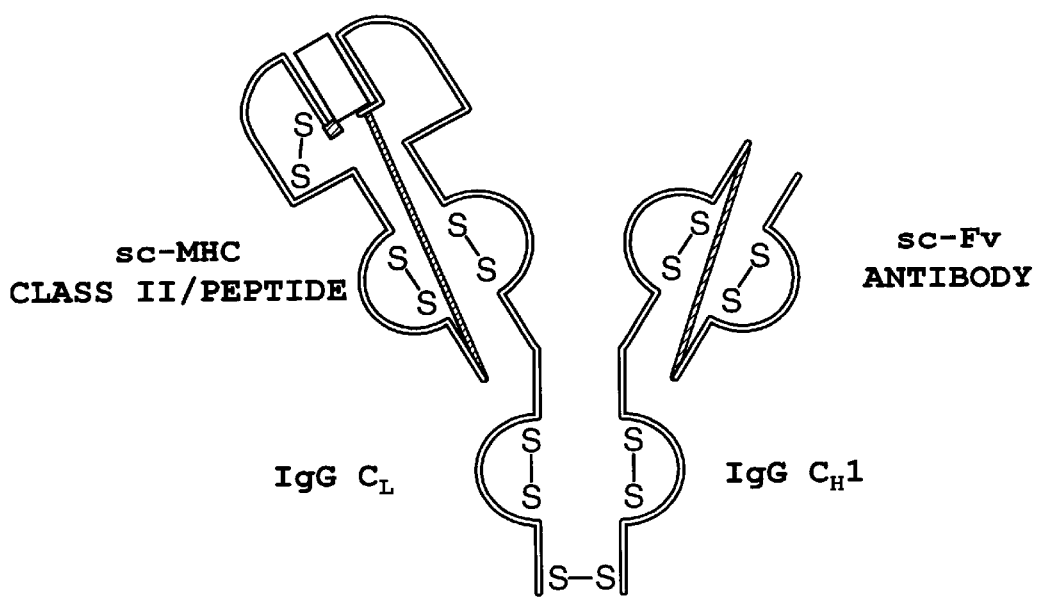

FIGS. 9A and 9B are schematic representations of polyspecific sc-class II/peptide IgG-C$_L$ dimer (9A) and a sc-class II/peptide IgG-C$_L$: single-chain antibody molecule (9B).

FIGS. 10A and 10B show oligonucleotides (10A) and polypeptide sequences (10B) used in examples below.

DETAILED DESCRIPTION OF THE INVENTION

As discussed above, the present invention provides novel MHC complexes that are fully soluble and functional. The MHC complexes include sc-MHC class I and class II complexes comprising a fused Ig-C$_L$ chain or fragment and/or a modified class II β2 chain. It has been found that by fusing the Ig-C$_L$ or suitable Ig-C$_L$ fragment to the MHC complexes, and/or by modifying the class II β2 chain, it is possible to significantly increase soluble expression of the MHC complexes. As mentioned above, polyspecific MHC complexes of the present invention can include a modified class II β2 chain and/or the Ig-C$_L$ chain or suitable Ig-C$_L$ chain fragment to facilitate soluble expression if desired.

In general, preparation of the MHC complexes of the invention includes conventional recombinant steps involving, e.g., oligonucleotide primer directed and site specific mutagenesis, polymerase chain amplification reactions (PCR), preparation of plasmid DNA, cleavage of DNA with restriction enzymes, ligation of DNA, isolation of mRNA, introduction of the DNA into a suitable cell, culturing of the cell, and isolation and purification of the expressed MHC complex. See generally, Sambrook et al.,

*Molecular Cloning: A Laboratory Manual.* (2nd ed. (1989); Ausubel et al., *Current Protocols in Molecular Biology*, John Wiley & Sons, New York (1989). The methods are suitable for making the MHC complexes disclosed herein including empty or loaded MHC molecules e.g., empty or loaded polyspecific MHC complexes, partially empty or loaded sc-MHC class II molecules, and MHC complexes comprising a fused presenting peptide.

The following discussion relating to preparation of an sc-MHC peptide fusion complex comprising a fused presenting peptide, peptide linkers, etc., has been disclosed in the published PCT Application Nos. WO96/04314 and WO 97/28191. It will be appreciated that the discussion is generally applicable to making and using the MHC complexes of the invention, including empty or loaded complexes. It will be understood from the following that to prepare the empty or loaded MHC complexes, DNA sequence encoding the fused presenting peptide is not included in a nucleic acid construct coding for the empty or loaded molecule.

DNA encoding a desired MHC protein (i.e., heterodimeric MHC molecule) can be obtained from any of several sources including the cell line disclosed for instance in Example 1 which follows. Other sources of DNA coding for the MHC protein are known, e.g. human lymphoblastoid cells. Once isolated, the gene coding for the MHC protein can be amplified by the polymerase chain reaction (PCR) or other means known in the art. Suitable PCR primers to amplify the MHC protein gene may add restriction sites to the PCR product. The PCR product also preferably includes a sequence coding for the linker sequence, or a restriction enzyme site for ligation of such a sequence. Suitable primers, PCR conditions and expression vector construction techniques are e.g. disclosed in the examples which follow and the Drawings.

The linker sequence is preferably a nucleotide sequence that codes for a peptide that can effectively position the presenting peptide in the binding groove of the MHC molecule. As used herein, the phrase "presenting peptide is effectively positioned in the binding groove of an MHC molecule" or "MHC fusion complex capable of modulating the activity of a T-cell", or other similar phrase, is intended to mean the presenting peptide linked to a MHC protein is positioned so that the presenting peptide fusion complex is capable of modulating the activity of a T-cell receptor, either to induce T-cell proliferation or to inhibit or inactivate T-cell development as determined by an assay disclosed below. One exemplary assay includes sequential steps of culturing T-cells to proliferate, and contacting the T-cells with a MHC complex of the invention and then evaluating whether the complex inhibits further development of the T-cells.

In general, a sc-MHC peptide fusion complex comprises MHC single-chains separated by a covalently linked peptide linker sequence. For example, a sc-MHC class II molecule will generally comprise an MHC class II β1,β2 chain linked to an MHC class II α1, α2 chain through a suitable single-chain linker sequence. As mentioned above, the class II β2 chain will often be modified as provided below. The single chain linker sequence thus should enable the linked MHC complex to fold to an active form, i.e., a form where the MHC molecule can modulate the activity of a T-cell. Such effective single chain linker sequences can be readily determined empirically. Thus, e.g., a DNA construct coding for a single chain MHC complex where the α and β chains are linked by a linker sequence can be cloned and expressed, and the single chain MHC complex tested to determine if the complex is capable of modulating the activity of a T-cell receptor, either to induce T-cell proliferation or to inhibit T-cell development as determined by the assays disclosed below.

The single-chain linker preferably predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. In general, the linker sequence does not contain any proline residues, which could inhibit flexibility. For those MHC fusion complexes that include an sc-MHC class II molecule with a covalently linked peptide, the linker sequence is suitably linked to the β chain of the MHC molecule, although the linker peptide sequence also could be attached to the a chain of the MHC molecule if desired. Exemplary peptide linker sequences comprise from about 7 to 20 amino acids, preferably from about 8 to 16 amino acids, more preferably from about 8 to 12 amino acids. The linker sequence is generally flexible so as not hold the presenting peptide in a single undesired conformation. For covalently linking a presenting peptide to a MHC class II β chain molecule, the amino sequence of the linker should be capable of spanning approximately 30 Angstroms from the N-terminal residue of the MHC class II p chain to the C-terminal residue of the presenting peptide. See for example FIGS. 1A and 1B of the published PCT Application. When such a β+peptide chain is expressed along with the α chain, the linked presenting peptide should fold into the α1 and β1 binding groove resulting in a functional MHC molecule as generally depicted in FIG. 1C of the published PCT Application. One suitable linker sequence is ASGGGGSGGG (SEQ ID NO: 35) (i.e., Ala Ser Gly Gly Gly Gly Ser Gly Gly Gly), linked, e.g., to the first amino acid of the β1 domain of the MHC class II protein. Different linker sequences could be used including any of a number of flexible linker designs that have been used successfully to join antibody variable regions together [(i.e. M. Whitlow et al., *Methods: A Companion to Methods in Enzymology*, 2:97–105 (1991)). Suitable size and sequence of single chain linker sequences also can be determined by conventional computer techniques.

Other suitable linker sequences can be identified empirically. For example, a DNA construct coding for a MHC fusion complex that includes a linker sequence can be cloned and expressed, and the fusion complex tested to determine if the complex is capable of modulating the activity of a T-cell receptor, either to induce T-cell proliferation or to inhibit or inactivate T-cell development as determined by the assay disclosed below. Suitable size and sequences of linker sequences also can be determined by conventional computer modeling techniques based on the predicted size and shape of the MHC complex.

In most instances restriction sites are engineered in the DNA construct comprising the fused nucleotide sequences coding for the linker sequence and MHC protein so that essentially any nucleotide sequence coding for a presenting peptide of interest (e.g. either an antigenic or an antagonist presenting peptide) can be attached to the construct. For example, in one system exemplified in the examples which follow, suitable restriction sites (e.g., AflII and NheI sites) are included between the end of the leader sequence and the beginning of the linker to facilitate insertion of a wide variety of presenting peptides to the β chain gene of the MHC molecule. See, for example, FIG. 3 of the published PCT application and examples which follow. The nucleotide and amino acid sequences of exemplary leader sequences are depicted in FIGS. 18A and 18B of the published PCT application No. WO96/04314. See also the examples which follow and the published PCT application No. WO 97/28191.

The presenting peptide component of a MHC fusion complex should be capable of modulating the activity of a T-cell as discussed above. For a MHC fusion complex that contains a class II MHC molecule, the presenting peptide usually has from about 4 to 35 amino acids, more preferably about 6 to about 30 amino acids, still more preferably from about 8 to about 25 amino acids. For a MHC fusion complex that contains a class I MHC molecule, preferably the presenting peptide has from about 4 to 25 amino acids, more preferably about 6 to about 20 amino acids, still more preferably from about 6 to about 15 amino acids, even more preferably 8 to about 10 amino acids. Class I and class II MHC molecules show preferential binding toward different peptide sequences. Recently, anchor residues defining MHC allele-specific peptide motifs have been identified in class II binding peptides (F. Sinigaglia et al., *Curr. Opin. in Immun.*, 6:52–56 (1994)). For example, in human class II HLA-DR1 molecules, an aromatic amino acid (e.g., Tyr, Phe, or Trp) is usually found near the amino terminus of the peptide (position 1), a hydrophobic residue (e.g., Met or Leu) at position 4 and a small amino acid (e.g., Ala or Gly) at position 6. Other MHC molecules have different motifs, e.g., for class II molecules, see Sinigaglia., supra; for class I molecules (see K. Parker et al., *J. Immunol.*, 152:163–175 (1994)). Preferred presenting peptides include the desired MHC binding motif in order to facilitate optimum MHC binding. Thus, for example, in human class II HLA-DR1 MHC molecules, an aromatic amino acid (e.g., Tyr, Phe, or Trp) is preferably located near the amino terminus of the presenting peptide (position 1), a hydrophobic residue (e.g., Met or Leu) is at position 4 of the presenting peptide, and a small amino acid (e.g., Ala or Gly) is at position 6 of the presenting peptide. For the immunosuppression methods of the invention (e.g., to treat autoimmune diseases or allergies, or otherwise suppress an unwanted T-cell response), the presenting peptide preferably may be the same as or homologous to (e.g., at least greater than about 80 or 90% shared sequence) a peptide known or suspected to be responsible for activating T-cells in the targeted disorder. Thus, for example, the MPB peptide 80–105 is recognized by over 30% of MPB-specific T-cells isolated from multiple sclerosis patients (see E. Meinl et al., *J. Clin. Invest.*, 92:2633–2643 (1993)) and should be a suitable as a presenting peptide in MHC fusion complexes used for immunosuppression applications as disclosed herein. See example 3 below. Additionally, the activity of a particular presenting peptide, i.e. antigenic or antagonist or partial agonist, can be readily determined empirically by the methods disclosed herein, including the in vivo assays disclosed below.

Figures 1, 6B:
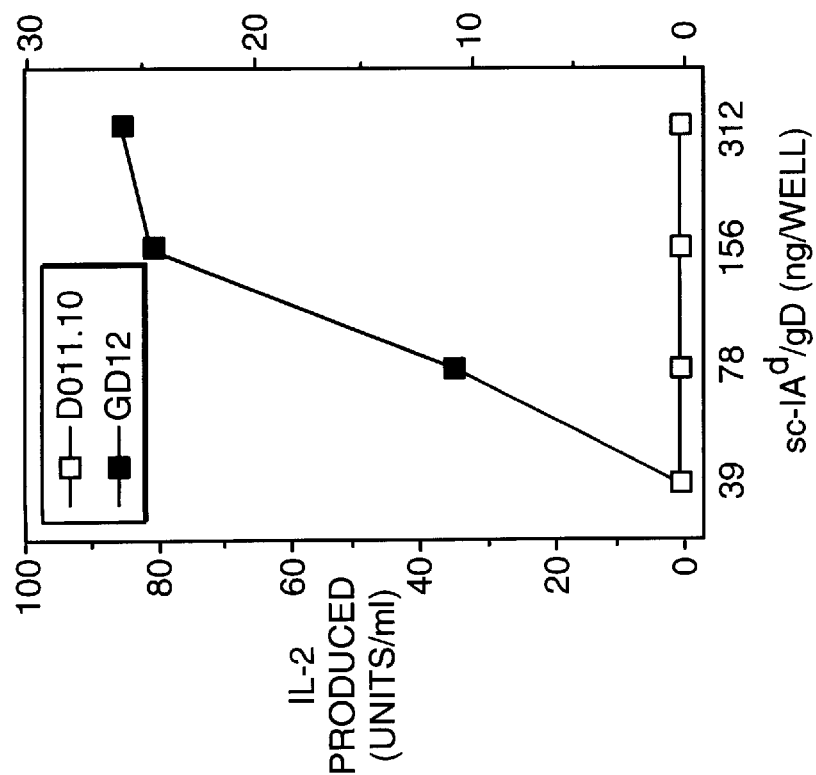
FIG. 1 is a schematic representation of the gene encoding the single chain IA$^d$/OVA 323–229 MHC fusion molecule (i.e., sc-IA$^d$/OVA) (SEQ ID NO: 24). The IA$^d$β2 chain is encoded by nucleotides 452 to 734 of the IA$^d$/OVA single-chain gene (SEQ ID NO: 24). The IA$^d$β2 chain spans amino acids 150 to 243 (SEQ ID NO: 25). The Kozak consensus sequence is indicated. The arrow designates the signal peptidase cleavage site. "//" in the IA$^d$β1-β2 and IA$^d$ α domains represents amino acid and nucleotide sequences omitted for clarity. The OVA 323–339 peptide (SEQ ID NO: 26) (dashed line) is absent in the sc-IA$^d$/blank MHC molecule.

As discussed above and in said PCT application Nos. WO 96/04314 and WO 97/28191 single-chain MHC fusion complexes are desirable, i.e. a fusion complex that consists of a single polypeptide rather than a multiple chain aggregate such the native heterotrimeric class II/peptide complex where α and β chains and a peptide are associated through non-covalent interactions. In the case of a single chain MHC class II complex, the α and β chain sub-units are linked as a single chain fusion protein with the presenting peptide preferably linked to the β chain of the chain fusion protein. Exemplary sc-MHC class II fusion complexes are depicted in FIGS. 1, 4A and 4B. Preferably a linker sequence is used to link the α and β chains. Such a linker sequence used to link domains of an MHC molecule is sometimes referred to herein as a "single chain linker sequence" and is thereby distinguished from the linker sequence discussed above that is interposed between and covalently links a presenting peptide and an MHC molecule. Examples of such linker sequences are shown in FIG. 1 below.

Preferably a single chain MHC class II complex is linked between the carboxyl terminus of the β2 domain and the amino terminus of the α1 domain, although multiple domains of a MHC complex may be linked through other positions.

The MHC molecules of the complexes provided herein suitably correspond in amino acid sequence to naturally occurring MHC molecules, e.g. MHC molecules of a human (class I or class II), mouse or other rodent, or other mammal. Preferably at least about 70 percent of the amino acid sequence of a MHC molecule of the fusion complex will be the same as the amino acid sequence of a naturally-occurring MHC molecule such as those mentioned above, more preferably at least about 90 percent amino acid sequence of a MHC molecule of the fusion complex will be the same as the amino acid sequence of a naturally occurring MHC molecule, and even more preferably about 98 percent to all of the amino acid sequence of a MHC molecule of the fusion complex will be the same as the amino acid sequence of a naturally occurring MHC molecule.

An empty MHC complex of the invention, particularly an empty single chain MHC molecule, can be made according to any suitable method described above, except that the presenting peptide is not covalently linked to the molecule. For example, as disclosed in the PCT Application No. WO97/28191 and in Examples 1–3 below, steps which join an oligonucleotide encoding the OVA presenting peptide to the linker-β1-β2 gene fragment can be omitted. In another example, a presenting peptide can be excluded from an MHC molecule of the invention which already has a covalently linked presenting peptide by using standard recombinant DNA manipulations. For example, DNA encoding the sc-IA$^d$/OVA presenting peptide can be removed with a suitable restriction enzyme (e.g., AflII and NheI).

As discussed above, we have found that it is possible to facilitate soluble expression of a variety of sc-MHC complexes by modifying the class II β2 chain. In particular, we have found that the β2 class II chain is dispensable for specific binding of the MHC complex. As noted earlier, the class II β2 chain modified in accordance with the invention can be any IA, IE, DR, DQ or DP chain for which a DNA sequence is known. DNA sequences for the class II β2 chains can be obtained from a variety of sources, e.g., Kabat, E.A., et al., (1991) *Sequences of Proteins of Immunological Interest* (5$^{th}$ Ed.) Public Health Services, National Institutes of Health; the disclosure of which is incorporated by reference.

Particularly, the human class II β1 and β2 chain domains typically correspond to amino acid positions 1 to 94 and 95 to 188 respectively where position 1 corresponds to N-terminal amino acid of the mature class II β chain. The positions may vary between 1 to 5 amino acids depending on the particular class II molecule. Exemplary class II β2 chain deletions include a deletion of the amino acid at position 95 at the start of the β2 domain to position 188 at the end of the β2 domain. See example 3 below. Alternatively, one or more contiguous or non-contiguous amino acids can be deleted from between positions 95 and 188 up to the entire length of the class II β2 chain.

More specifically, the class II β2 IA$^d$ chain is encoded by DNA sequence spanning nucleotides 452 to 734 of the IA$^d$/OVA 323–229 MHC molecule (See FIG. 1 and SEQ ID NO: 24). The IA$^d$/OVA β2 chain spans amino acids 150 to 243 (SEQ ID NO: 25). See also Examples 1 and 3 below for disclosure relating to making single chain MHC molecules comprising a class II IA$^d$ or DR β2 chain.

As noted above, in one embodiment of the present invention, an MHC class II complex is provided with a deleted β2 class II chain deletion. The β2 class II chain deletion can span at least 1 amino acid, preferably at least 5, 10, 25, 50, 60, 70, 80 or 90 amino acids and more preferably essentially all of the amino acids of the class II β2 chain. In another embodiment, the MHC complex can include a modified β2 class II chain comprising a deletion of one or more non-contiguous amino acids up to a deletion of essentially the entire class II β2 chain.

Preferred non-contiguous deletions can span at least 2 amino acids, preferably at least 5 to 10, or more amino acids of the class II β2 chain.

In another illustrative embodiment of the invention, the MHC class II complex can include a β2 class II chain modification in which one or more amino acids are substituted with another amino acid. Preferred substitutions of the class II β2 chain can be conservative or non-conservative amino acid substitutions in which at least 1 amino acid of the chain, preferably at least 2, 5, 10, 25, 50, 60, 70, 80, 90 or more amino acids of the chain are substituted with a conservative or non-conservative amino acid. Accordingly, a tyrosine amino acid substituted with a phenylalanine will be an example of a conservative amino acid substitution, whereas an arginine replaced with an alanine would represent a non-conservative amino acid substitution. Preferably, the conservative or non-conservative amino acid substitution is a hydrophilic or neutral amino acid. In particular, one or more Cys residues in the β2 class II chain can be substituted with a non-Cys residue so that potential for cross-linking is substantially reduced or eliminated. Preferably at least 1 and more preferably all of the Cys residues are substituted with a non-Cys residue. See Example 3 below which discloses an exemplary class II β2 chain in which a Cys residue has been replaced by Ser.

Other class II β2 chain modifications are within the scope of the present invention. For example, the class II β2 chain can be modified to include one or more amino acid additions between position 95 and the final position 188 of the class II β2 domain. More particularly, the β2 chain can be modified to include one or more additions of preferably neutral or hydrophilic residues. Preferably, the modified class II β2 chain includes at least one neutral or hydrophilic amino acid, more preferably 2, 5, 10, 15 or 20 amino acids up to about 25 to 30 amino acids. In this embodiment, it will usually be desirable to constrain the number of added amino acid residues to about the length of the class II β2 chain. Thus, in most instances it will be desirable to remove an equivalent or nearly equivalent number of class II β2 chain residues for each amino acid added to the chain. In some cases, removal of additional sequence adjacent to the β2 class II chain such as linker sequence and/or β1 chain sequence can further improve solubility without negatively impacting specific binding between the presenting peptide binding and the MHC molecule. Such constructs can be readily made and tested in accordance with the methods described herein.

A class II β2 chain modification in accordance with invention can be accomplished by a variety of standard recombinant techniques, including use of restriction enzymes or PCR primers to excise nucleic acid encoding one or more amino acids from pre-amplified DNA sequence encoding the class II β2 chain. Preferred methods of making such deletions include oligonucleotide primer directed site specific mutagenesis using mutagenic DNA oligonucleotide primers and PCR to amplify pre-determined β2 chain sites.

As discussed above, an MHC complex of the invention can include a covalently linked Ig-C$_L$ chain linked, e.g., to the C-terminus of the complex. In one embodiment, the MHC complex includes a fused mammalian Ig-C$_L$ chain, preferably a full-length murine or human Ig-C$_L$ chain (Cκ or Cλ). The nucleic acid and protein sequences of murine and human Ig-C$_L$ chains have been disclosed. See e.g., *Fundamental Immunology*, (1993) 3$^{rd}$ Ed., W. Paul. Ed. Rsen. Press Ltd. New York; and Kabat, E. A. supra.

By the term Ig-C$_L$ chain is also meant an immunoglobin light chain constant region which varies from a disclosed full-length sequence by one or more amino acid substitutions or additions. An amino acid can be added to a disclosed Ig-C$_L$ chain sequence at one or both ends of the chain, e.g., by conventional recombinant methods. In addition, the recombinant methods can be used to substitute one or more than one specified amino acid in the chain if desired, preferably by neutral or hydrophilic amino acids. The substitutions can be conservative or non-conservative if desired. Generally, the amino acid additions will include between about 1 to 30 neutral or hydrophilic amino acids, preferably between about 2, 5, 10, 20 or 25 of such amino acids. An amino acid substituted for another amino acid in the Ig-C$_L$ chain will typically be a conservative or non-conservative amino acid replacement. As will be pointed out below for Ig-C$_L$ chain fragments, an MHC molecule of the invention comprising the fused Ig-C$_L$ chain will be fully soluble and functional.

It will be desirable in some instances to fuse a suitable Ig-C$_L$ chain fragment such as a murine or human Cκ chain fragment to the MHC complexes disclosed herein. By the phrase "suitable Ig-C$_L$ chain fragment" is meant a portion of a full-length Ig-C$_L$ λ or κ sequence which when fused to a desired MHC complex, forms a fully soluble and functional complex as defined below. The Ig-C$_L$ chain fragments (both Cκ and Cλ type) can be made according to standard recombinant methods, and can be contiguous or non-contiguous deletions of the full-length sequence. For example, a suitable Ig-C$_L$ fragment can be made by PCR amplification of a murine or human Cκ or Cλ chain fragment of interest followed by ligation of the PCR product to a DNA segment or vector encoding the MHC complex. The PCR product can be manipulated as desired to include restriction enzyme cleavage sites. A particularly preferred method of making an Ig-C$_L$ chain fragment is oligonucleotide directed site specific mutagenesis using mutagenic DNA primers and PCR to amplify pre-determined β2 chain sites. Generally, a suitable murine or human Cκ chain fragment will be between about 80 to 130 amino acids, preferably between about 90 to 120 amino acids, and more preferably between about 100 to 110 amino acids in length. Cells comprising murine or human Cκ chain DNA suitable for PCR amplification are known in the field. See the examples which follow.

The class II β2 chain modifications, Ig-C$_L$ chain, and Ig-C$_L$ chain fragment fusions discussed above do not significantly impact the capacity of an MHC complex of the invention to specifically bind a ligand. That is, by modifying the class II β2 chain and/or by fusing the Ig-C$_L$ chain or the Ig-C$_L$ chain fragment to an MHC complex, specific binding by the MHC complex is not reduced by more than about 30%, preferably by not more than 10%, and more preferably by not more than 5% or less when compared to a suitable control such as a sc-MHC complex comprising a full-length class II β2 chain and lacking a fused Ig-$C_L$ or fragment. Exemplary binding assays are disclosed in the examples which follow and include standard Western blots and T-cell stimulation assays.

As mentioned above, an MHC complex of the invention is fully soluble and functional. By the term "fully functional" or similar term is meant that the fusion protein specifically binds ligand in the presence of the class II β2 chain modification and/or fused Ig-$C_L$ chain or suitable Ig-$C_L$ chain fragment. Assays for detecting such specific binding are disclosed herein.

By the term "fully soluble" or similar term is meant that the fusion protein is not readily sedimented under low G-force centrifugation (e.g. less than about 30,000 revolutions per minute in a standard centrifuge) from an aqueous buffer, e.g., cell media. Further, an MHC complex is soluble if the fusion protein remains in aqueous solution at a temperature greater than about 5–37° C. and at or near neutral pH in the presence of low or no concentration of an anionic or non-ionic detergent. Under these conditions, a soluble protein will often have a low sedimentation value e.g., less than about 10 to 50 svedberg units. Aqueous solutions referenced herein typically have a buffering compound to establish pH, typically within a pH range of about 5–9, and an ionic strength range between about 2 mM and 500 mM. Sometimes a protease inhibitor or mild non-ionic detergent is added. Additionally, a carrier protein may be added if desired such as bovine serum albumin (BSA) to a few mg/ml. Exemplary aqueous buffers include standard phosphate buffered saline, tris-buffered saline, or other well known buffers and cell media formulations.

The present invention also relates to single-chain and multi-chain polyspecific MHC class I and class II complexes. The multi-chain polyspecific complexes are represented by the following general formula:

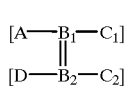

Formula I wherein,
a) A is one or more sc-MHC class I or class II molecules,
b) $B_1$, $B_2$ are each independently one or more of a joining molecule the same or different,
c) $C_1$, $C_2$ are each independently one or more of an effector molecule the same or different, or -H; and
d) D is one or more sc-MHC class I or class II molecules the same or different from A as defined above, or D is one or more of a ligand binding molecule.

Further provided are single-chain polyspecific MHC class I or II complexes represented by the following general formulae: A-$B_1$-$C_1$, $B_1$-A-$C_1$, and A-$C_1$-$B_1$, where A, $B_1$, $C_1$ are as defined above provided that when the polyspecific class I or class II complex is represented by A-$C_1$-$B_1$, $C_1$ is not -H.

With respect to each of the formulae provided above, a single line represents a covalent bond (e.g., a peptide bond), whereas a double line represents one or more covalent bonds, e.g., a disulfide bond such as those linking immunoglobin heavy chains; or the double line represents hydrogen bonds. The brackets indicate flexibility in the sequential arrangement of the bracketed molecules (i.e., subunits). Thus, the order of the subunits is not important so long as each subunit performs the function for which it is intended.

As noted above, in each of the formulae shown representing the polyspecific MHC complexes, the subunits A, $B_1$, $B_2$, $C_1$, $C_2$ and D, each independently represent one or a plurality of the molecules. In instances where the subunit represents a plurality of the molecules, each molecule will typically be attached to the same type of molecule (e.g., a sc-MHC class II molecule recombinantly attached to another sc-MHC class II molecule). In addition, the number of such linked molecules will generally be between about 2 to 10, preferably about 2 to 5, more preferably 2 of such molecules, and most preferably 1 of such molecules. The sc-MHC class II molecules can each independently include a covalently linked presenting peptide, or alternatively, the sc-MHC class II molecule can be empty and a suitable presenting peptide can be loaded according to methods described herein. Each subunit or plurality of molecules comprising same can be spaced by suitable peptide linkers to enhance flexibility as desired.

In accordance with the present invention, it will often be desirable to modify the β2 class II chain of those polyspecific MHC complexes comprising class II β2 chains. Alternatively, or in addition, an Ig-$C_L$ chain or suitable Ig-$C_L$ chain fragment, can be fused to the polyspecific MHC complex. For example, with respect to the polyspecific MHC complexes provided, $B_1$ or $B_2$ in the above formulae can each represent an Ig-$C_L$ chain or suitable Ig-$C_L$ chain fragment, e.g., a murine or human Cκ chain fragment. In this embodiment, the multi-chain polyspecific MHC molecule may include a suitable heavy chain constant domain such as $CH_1$ or a suitable fragment thereof so that the complex can form a specific binding pair.

The polyspecific MHC complexes of the present invention can include one or more joining molecules derived whole or in part from an immunoglobin. In cases where the complex includes more than one joining molecule (e.g., a multi-chain polyspecific molecule), the joining molecules can be the same or different class (IgG, IgA, IgM, IgD, or IgE class). Thus, chimeric polyspecific MHC complexes are within the scope of the present invention. For example, a joining molecule can be an immunoglobin light chain (κ or λ type) or a joining molecule can be a heavy chain constant region or fragment as indicated above. Exemplary joining molecule pairs thus include $C_L$ (κ or λ type), $CH_1$; $CH_2$ $CH_2$; or $CH_3$, $CH_3$ chains; or suitable fragments thereof capable of forming specific binding pairs as determined by assays described herein. Examples of other suitable joining molecules include helix-turn-helix and coiled-coil protein binding motifs capable of forming specific binding pairs.

The immunoglobin joining molecule may be of animal (e.g., a rodent such as a mouse or rat), or human origin or may be chimeric or humanized (see e.g., Morrison et al., *PNAS* 81, 6851 (1984); Jones et al. *Nature* 321, 522 (1986)). Exemplary joining molecules include those capable of being specifically bound by anti-idiotype antibodies such as those disclosed below as well as, e.g., commercially available anti-idiotype antibodies such as those disclosed in Linscott's Directory (40 Glen Drive, Mill Valley Calif. 94941), and by the American Type Culture Collection (ATCC) 12301 Parklawn Drive, Rockville, Md. 20852.

An illustrative example of a polyspecific MHC complex of the invention is the bispecific complex shown in FIG. 9A. In this embodiment, the bispecific MHC complex includes two sc-MHC class II peptide complexes and two Ig-$C_L$ joining molecules that form a specific binding pair. The two sc-MHC class II peptide complexes can be the same or different although in some instances it is preferred that they be the same to increase binding strength of the bispecific MHC complex.

Another illustrative example is shown in FIG. 9B. In this embodiment, the bispecific complex includes a sc-MHC class II peptide complex and sc-Fv antibody (often referred to as a "single-chain antibody"). The bispecific complex further includes Ig-$C_L$ and an IgG$C_H$1 joining molecules that form a specific binding pair. The sc-MHC class II peptide complex and the sc-Fv antibody can bind the same or different molecule, e.g., a T-cell receptor or other molecule on a T-cell.

A bispecific complex according to the invention can include one or several ligand binding molecules. The ligand binding molecule can be a single-chain antibody as shown in FIG. 9B or it can be a fragment thereof or an immunoglobin variable region (e.g., Fv) capable of specifically binding an antigen. Such antigen-binding immunoglobin fragments or variable regions are known. See e.g., protein sequences disclosed in the Brookhaven Protein Data Bank (Brookhaven Protein Data Base, Chemistry Dept. *Brookhaven National Laboratory*, Upton, N.Y. (1973); Kabat, et. al., supra.

A single-chain antibody suitable for inclusion in a polyspecific complex of the invention can be made by several well-known methods. See generally, Pastan, I and Fitzgerald D., (1991) *Science* 254:1173; Webber, et al., *Molecular Immunol.* (1995), 32:249; and published PCT application Nos. WO96/05228 and WO 97/28191 for disclosure relating to making and using single-chain antibodies. Exemplary single-chain antibodies are those capable of specifically binding cell surface targets such as glycoproteins and lipoproteins. Examples of particular glycoproteins include, but are not limited to, CD2, CD3, CD4, CD8, CD28, CD40, CD45, CTLA4, and Fas. See Gilliland L. K., et al., (1996) *Tissue Antigens* 47:1 for disclosure relating to generating and characterizing single-chain antibodies that bind these molecules.

In another illustrative embodiment, the ligand binding molecule D as shown in Formula I above can be a receptor ligand, which ligand can tether the complex to a cell receptor binding partner. Exemplary receptor ligands include FasL.

As an alternative to making polyspecific MHC complexes comprising a fused single-chain antibody, it will be useful in some cases to couple a desired antibody (or antigen binding fragment thereof e.g., a monoclonal antibody, to an MHC complex of the invention. For example, such an approach can be useful when DNA sequence encoding a desired antibody variable region is unknown. Typically, the coupling will include standard protein coupling reactions such as those generally described in means, G. E. and Feeney, R. E. (1974) in *Chemical Modification of Proteins*, Holden-Day. See also, S. S. Wong (1991) in *Chemistry of Protein Conjugation and Cross-Linking*, CRC Press. Exemplary monoclonal antibodies include those that specifically bind CD28, CTLA4, or FAS.

As mentioned previously, the present invention also features polyspecific MHC complexes which include non-immunoglobin joining molecules. For example, the first and second joining molecules can be proteins (or polypeptides) which include (or consist of) a protein-protein binding motif such as, e.g., a helix-turn-helix or leucine zipper motif. Many examples of these binding motifs have been described (see e.g., Horberg, et al., (1993) *Science* 262:1401; Kamtekar, et al., (1993) *Science* 262:1680; Harris, et al., *J. Mol. Biol.* (1996) 236:1356) Such protein-protein binding motifs generally form specific binding pairs and are often found in, e.g., transcription factors such as, e.g., fos, jun and the like. Example 14 below discloses preferred non-immunoglobin joining molecules.

Additionally, it will be appreciated that the polyspecific MHC complexes of the invention can be modified in several well-known ways to suit intended uses. For example, the complexes can be disulfide-stabilized in accordance with known methods (see e.g., the published PCT application no. WO/29350).

Molecular weights of the MHC molecules of the invention will vary, depending on several parameters including whether the molecule is soluble or full length (including membrane bound) and/or if an Ig-$C_L$ chain or suitable fragment is selected for fusion to the MHC molecule. A soluble MHC class II fusion complex generally will have a molecular weight of greater than about 45 kDa, and mature α and β chains without trans-membrane and cytoplasmic domains each will have a molecular weight of greater than about 20 kDa, more typically between about 21 to about 26 kDa. Typically, mature single-chain MHC class II molecules without transmembrane and cytoplasmic domains will have a molecular weight of about 48 to about 50 kDa. For full length (membrane bound) molecules, mature α and β chains generally will have a molecular weight of greater than about 25 kDa, preferably between about 26 and about 30 kDa. Typically, mature single-chain MHC class II fusion molecules with a single (linked to α or β chain) transmembrane or membrane anchor domain will have a molecular weight of greater than about 49 kDa, preferably between about 50 and 52 kDa. All of the above mentioned molecular weights can be made by a SDS-PAGE gel electrophoresis.

Multivalent sc-MHC complexes are desirable for a number of applications. The valence of a MHC-antigenic peptide complex influences the effect of the complex on T-cell receptor(s). For example, activation of the 3DT52.5 T-cell hybridomas requires a MHC-antigenic molecule that has been made multivalent. Monovalent, soluble MHC complexes are incapable of stimulating this T-cell (J. McCluskey et al., *J. Immunology*, 141:1451–1455 (1988)). Desired multivalent MHC complexes include those linked to an immunoglobulin, e.g., IgG, IgM or Fab'2. Chemically cross-linked MHC fusion complexes (for example cross-linked to dendrimers) are also suitable multivalent species. For example, the MHC complex can be genetically modified by including sequences encoding amino acid residues with chemically reactive side chains such as Cys or His. Such amino acids with chemically reactive side chains may be positioned in a variety of positions of a MHC fusion complex, preferably distal to the presenting peptide and binding domain of the MHC fusion complex. For example, the C-terminus of the β chain of a MHC molecule distal from the presenting peptide suitably may contain such reactive amino acid(s). Suitable side chains can be used to chemically link two or more MHC complexes to a suitable dendrimer particle to give a multivalent MHC complex. Dendrimers are synthetic chemical polymers that can have any one of a number of different functional groups of their surface [D. Tomalia, *Aldrichimica Acta*, 26:91:101 (1993)]. Exemplary dendrimers for use in accordance with the present invention include e.g. E9 starburst polyamine dendrimer and E9 comburst polyamine dendrimer, which can link cysteine residues.

A DNA segment encoding a MHC complex of the invention can be inserted into a suitable DNA vector by several recombinant techniques. For those complexes including a fused presenting peptide, DNA coding for the presenting peptide can be obtained by isolating DNA from natural sources or by known synthetic methods, e.g. the phosphate triester method. See, e.g., *Oligonucleotide Synthesis*, IRL Press (M. Gait, ed., 1984). Synthetic oligonucleotides also may be prepared using commercially available automated oligonucleotide synthesizers. A nucleotide sequence coding for a MHC complex may be directly joined to a DNA sequence coding for the presenting peptide or, more typically, a DNA sequence coding for the linker sequence as discussed above may be interposed between the sequence coding for the MHC molecule and the sequence coding for the presenting peptide and joined using suitable ligases.

Other nucleotide sequences also can be included in the DNA segment. For example, a promoter sequence, which controls expression of the sequence coding for the MHC complex, or a leader sequence, which directs the MHC complex to the cell surface or the culture medium, can be included in the construct or present in the expression vector into which the construct is inserted. Exemplary promoters include immunoglobulin or viral promoters such as a cytomeglovirus (CMV) promoters. See the examples which follow. A strong translation initiation sequence also can be included in the construct to enhance efficiency of translational initiation. A preferred initiation sequence is the Kozak consensus sequence (CCACCATG) (SEQ ID NO: 1).

Preferably a leader sequence included in a DNA construct contains an effectively positioned restriction site so that an oligonucleotide encoding a presenting peptide of interest can be attached to the MHC molecule if desired. Suitably the restriction site can be incorporated into the 3-end of the leader sequence, sometimes referred to herein as a junction sequence, e.g. of about 2 to 10 codons in length, that is positioned before the coding region for the presenting peptide. An exemplary restriction site is the AflII site, although other cleavage sites also can be incorporated before the presenting peptide coding region. As discussed above, use of such a restriction site in combination with a second restriction site, typically positioned at the beginning of the sequence coding for the linker, enables rapid and straightforward insertion of sequences coding for a wide variety of presenting peptides into the DNA construct for the MHC complex. Exemplary leader sequences contain a strong translation initiation site and a cap site at the 3'-end of their mRNA. For example, a leader sequence can be attached to the α1 domain of a class I MHC molecule, or a leader sequence can be attached to the α1 domain of a class II MHC molecule. Preferred leader sequences provide for secretory expression of the MHC fusion complex.

Examples of particular sc-MHC class II constructs contain linked nucleotide sequences encoding in sequence: β chain leader/presenting peptide/linker sequence/β1-Δβ2 chain/single chain linker sequence/α1-α2 chain; β chain leader/presenting peptide/linker sequence/β1-Δβ2 chain/single chain linker sequence/α1-α2 chain/Ig-$C_L$ chain; and β chain leader/presenting peptide/linker sequence/β1-β2 chain/single chain linker sequence/α1-α2 chain/Ig-$C_L$ chain; wherein the Δ (delta) symbol denotes a β2 class II chain modification as described above, preferably a β2 class II chain deletion up to and including essentially the entire β2 chain. Further examples of sc-MHC class II constructs are the linked nucleotide sequences just-mentioned except the Ig-$C_L$ chain is substituted with a suitable Ig-$C_L$ chain fragment. MHC DNA constructs are suitably introduced into bacterial, baculoviral-insect cell and mammalian expression systems, including those specific expression systems disclosed herein. The MHC complexes are then expressed and purified if desired to obtain substantially pure MHC complex.

As noted above, the MHC complexes of the invention include those complexes comprising class II β2 chain modifications and/or Ig-$C_L$ chain or suitable Ig-$C_L$ chain fragment fusions to facilitate expression of fully soluble and functional molecules. However, if desired, the MHC complexes can be provided as part of a cell membrane, e.g., an immune cell membrane. Methods for making and using membrane-bound forms of MHC complexes have been disclosed in the published PCT application No. 96/04314.

It may be desirable to construct a single expression vector that expresses both chains of an MHC complex of the invention, i.e. sequences that code for both the α and β chains of an MHC fusion complex are each connected to a single expression vector, even if not a single chain molecule. Such an expression vector may provide better results than where separate vectors are used for each chain of a MHC complex, particularly where selection is difficult for cells into which the vector has been introduced. It also may be desirable to construct a single expression vector that codes for both chains of a MHC complex (e.g., a polyspecific MHC complex) as well as other agents, particularly a T-cell costimulatory factor such as B7 or B7-2, i.e. sequences that code for both chains of an MHC complex and sequence(s) that code for a costimulatory factor are each connected to a single expression vector, to enable a single transformation procedure. Again, this approach would avoid potentially difficult selection for cells that have been transformed or transfected two or more times.

As an illustrative example of a DNA vector encoding a polyspecific MHC complex of the present invention, the DNA vector can include a DNA segment encoding a suitable joining molecule, which DNA segment is recombinantly fused to the 5' or 3' end of another DNA segment encoding a sc-MHC class II molecule, including, e.g., a recombinantly fused presenting peptide. The DNA sequence can be optionally fused to sequence encoding an effector molecule if desired. Preferred joining molecules are derived from immunoglobin light or heavy chain constant regions which are capable of specifically binding another immunoglobin light or heavy chain constant region and have a molecular weight of between about 20 to 30 kDa as determined by SDS-PAGE gel electrophoresis.

The polyspecific MHC complexes of the present invention can be produced by one or a combination of strategies. As an illustrative example, a bispecific MHC complex can be prepared by co-expressing in a suitable cell: i) a DNA expression vector encoding the A-$B_1$-$C_1$ chain, and 2) a DNA molecule encoding the D-$B_2$-$C_2$ chain as defined above. In instances where the joining molecules are derived whole or in part from immunoglobins, suitable methods for making and using DNA expression vectors encoding immunoglobin heavy and light chains can be used (see e.g., Near et al. *Mol. Immunol.* 30, 4, 369 (1993); Near et al. *Mol. Immunol.* 27, 901 (1990)). Alternating, the bispecific MHC complex can be encoded by a single DNA vector comprising DNA segments encoding each single-chain.

As also mentioned above, the MHC complexes of the present invention can be provided in kit form suitable for a variety of applications including research, clinical and commercial use. For example, such a kit can be used in accordance with the present invention to detect structures of interest such as cells comprising desired cell surface molecules. Of particular interest are immune cells such as T-cells including desired TCRs or other cell surface molecules such as other receptors, glycoproteins, lipoproteins, or cells labeled with a tag or with an antibody, e.g., a monoclonal antibody. In general, the kit will include one or more MHC complexes of the invention featuring a desired binding specificity, or in the case of the polyspecific MHC complexes disclosed herein more than one desired binding specificity. A suitable aqueous buffer will usually be provided, e.g., to administer one or more of the MHC complexes to a subject or for performing a specific binding reaction between the MHC complexes and desired target structures in a biological sample. If desired, the kit can include one or more detectably-labeled MHC complexes, either in unbound form or immobilized on a desired solid support. Alternatively, the kit may include instructions for labeling the complex with a detectable label as described herein.

As disclosed in the PCT application Nos. WO 96/04314 and WO 97/28191 a number of strategies can be employed to express MHC complexes of the invention. For example, an MHC gene fusion construct described above can be incorporated into a suitable vector by known means such as by use of restriction enzymes to make cuts in the vector for insertion of the construct followed by ligation. The vector containing the gene construct is then introduced into a suitable host for expression of the MHC complex. See, generally, Sambrook et al., supra. Selection of suitable vectors can be made empirically based on factors relating to the cloning protocol. For example, the vector should be compatible with, and have the proper replicon for the host that is being employed. Further the vector must be able to accommodate the DNA sequence coding for the MHC complex that is to be expressed.

In one preferred protocol for preparation of soluble MHC fusion complexes, DNA sequences encoding the presenting peptide and β1-β2 chains of the MHC molecule (class II) are arranged such that the C-terminal end of the presenting peptide is attached to an initial amino acid of the β1 domain, preferably the first amino acid of the β1 domain by a flexible linker sequence. Such a construct is depicted in FIG. 4 below. For a class I MHC molecule, preferably the DNA sequence encoding the presenting peptide is attached to the α domain of the MHC molecule, preferably such that the presenting peptide will be linked to the N-terminus end of that a chain. As discussed above, preferably restriction sites are engineered between the end of the leader sequence and the beginning of the linker so that essentially any oligonucleotide encoding a presenting peptide of interest (i.e. antigenic or antagonist) can be attached to the β chain gene.

As discussed previously, the β2 class II chain can be modified and/or the Ig-$C_L$ chain or fragment fused to the MHC complexes to facilitate soluble expression. Expressed MHC fusion complexes can be isolated and purified by known methods. For example, in one particular method, culture medium is centrifuged and then the supernatant is purified by affinity or immunoaffinity chromatography, e.g. Protein-A or Protein-G affinity chromatography or an immunoaffinity protocol comprising use of monoclonal antibodies that bind the expressed fusion complex such as a linked MHC or immunoglobulin region thereof. For example, MHC fusion complexes containing human HLA-DR1 sequences can be purified by affinity chromatography on a monoclonal antibody L243-Sepharose column by procedures that are generally known and disclosed, e.g., see Harlow, E. et al., *Antibodies, A Laboratory Manual* (1988). The L243 monoclonal antibody is specific to a conformational epitope of the properly folded HLA-DR1 molecule (J. Gorga et al., *J. Biol. Chem.*, 262:16087–16094), and therefore would be preferred for purifying the biologically active MHC fusion complex. The MHC complex also may contain a sequence to aid in purification. See, e.g., Example 7 and FIG. 4A which follows which discloses use of the 6xHis and EE tags.

Single chain MHC complexes can be prepared as discussed above and in the PCT application Nos. WO 96/04314 and WO 97/28191 as well as the examples which follow, including Examples 1–8. For example, DNA coding for a desired MHC protein can be obtained from a suitable cell line, and the isolated gene can be amplified by PCR or other means. In the case of a MHC class II molecule, an α1-α2 gene fragment can be cloned into a vector, followed by cloning of a gene fragment cloning for the β1-β2 domains with an interposed single chain linker sequence. The single vector is then expressed in a suitable host and the single chain molecule harvested and purified if desired. See the examples which follow, including Examples 1–8. See also U.S. Pat. No. 5,260,203 to Ladner et al., which discusses preparation of single chain antibodies, which methods can be generally employed to the single chain MHC fusion complexes of this invention.

In an exemplary preparation method, coding regions of the α and β chains of the MHC class II molecules are obtained, particularly by isolating the coding regions by PCR from a B cell line or other MHC molecule source. A sequence encoding a single-chain β-α fusion MHC fusion molecule can be constructed by replacing sequences encoding the transmembrane spanning domain of the β chain gene with a single chain linker sequence as discussed above which joins the β chain gene to the mature α chain (particularly at the first codon of the a chain gene). The α chain gene may suitably contain its transmembrane region for membrane bound expression of the single chain fusion complex, or the α chain gene may be truncated at the end of the extracellular region for soluble expression of the single chain MHC fusion complex. A suitable restriction site and linker for the presenting peptide is preferably included between the β chain leader and the first codon of the β chain. As provided above, the class II β2 chain can be deleted to facilitate soluble expression, in which case the β1 chain will be linked to the single-chain linker. Alternatively, or in addition, the resulting construct can be further modified by fusing a suitable Ig-$C_L$ chain or suitable Ig-$C_L$ fragment to the molecule, preferably at the end encoding the β chain. The coding region of essentially any presenting peptide can then be introduced as an oligonucleotide into the created restriction site. The construct is then suitably placed under the control of a mammalian or bacterial promoter, including those specific promoters disclosed herein. As will be appreciated, fusion of the Ig-$C_L$ chain or suitable Ig-$C_L$ chain fragment can be accomplished by ligation to a suitable vector encoding the desired Ig-$C_L$ chain or fragment. See, e.g., Near, et al., supra and the examples which follow for a discussion of suitable vectors.

As mentioned above, the MHC complexes of the present invention can include a variety of effector molecules. Suitable effector molecules include those which impart a desired biological, chemical or physical property to the MHC complex. More specifically, the effector molecule can be a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin. Biologically active fragments of such toxins are well known in the art and include, e.g., DT A chain and ricin A chain. Additionally, the toxin can be an agent active at the cell surface such as, e.g., phospholipase enzymes (e.g., phospholipase C). As another example, the effector molecule can be a chemotherapeutic drug such as, e.g., vindesine, vincristine, vinblastin, methotrexate, adriamycin, bleomycin, or cisplatin, or, additionally, the effector molecule can be a radionuclide such as, e.g., iodine-131, yttrium-90, rhenium-188 or bismuth-212. See e.g., Moskaug, et al. *J. Biol. Chem.* 264, 15709 (1989); Pastan, I.

et al. *Cell* 47, 641, 1986; Pastan et al., *Recombinant Toxins as Novel Therapeutic Agents, Ann. Rev. Biochem.* 61, 331, (1992); "*Chimeric Toxins*" Olsnes and Phil, *Pharmac. Ther.*, 25:355 (1982); published PCT application no. WO 94/29350; published PCT application no. WO 94/04689; and U.S. Pat. No. 5,620,939, each reference hereby incorporated by reference).

Still further examples of a suitable effector is a protein tag which is a polypeptide bearing a charge at physiological pH, such as, e.g., 6xHIS. In this instance, a suitable synthetic matrix to purify the MHC complex, if desired, would be, e.g., a commercially available metallo-sepharose such as, e.g., Ni-sepharose or other such suitable matrix capable of binding 6xHIS at about pH 6–9. The EE epitope and myc epitope are further examples of suitable protein tags, which epitopes can be specifically bound by one or more commercially available monoclonal antibodies. In general, a wide variety of epitopes capable of being specifically bound by an antibody, preferably a commercially available monoclonal antibody, is capable as serving as a tag of the MHC complexes of the invention.

In some embodiments of the present invention, an MHC complex it may be useful to fuse a protein tag with a chemical or protease cleavage site such as, e.g., a thrombin or snake venom protease cleavage site, so that the tag (or other MHC sub-units fused to the tag) can be removed in a controlled fashion.

It will be appreciated from the foregoing that in some cases an effector molecule such as a protein tag can also be a joining molecule. Effector molecules may be conjugated to the MHC complexes by means of a heterobifunctional protein cross-linking agent such as, e.g., SPDP, carbodimide, or the like. See Meany and Feeney, supra; Wong, supra.

It will be useful for some applications to non-recombinantly modify the MHC complexes of the invention. For example, this can be achieved by conjugation of a desired agent although often that agent can be recombinantly fused to the complex if desired. For example, the MHC complexes can include a variety of pharmaceutical agents in addition to those described above such as drugs, enzymes, hormones, chelating agents capable of binding, e.g., a radionuclide, as well as other proteins and polypeptides useful for diagnosis or treatment of disease. For diagnostic purposes, the MHC complexes can either be labeled or unlabelled. For example, a wide variety of labels may be suitably employed, such as radionuclides, fluors, enzymes, enzyme substrates, enzyme cofactors, enzyme inhibitors, ligands such as, e.g., haptens, and the like.

As mentioned above, it may be desirable in some cases to flexibly position subunits of an MHC complex of the invention by including a fused peptide linker sequence. Several suitable peptide linkers and methods of testing same have been described and are readily adapted for use with the complexes. In addition, in some cases it may be useful to add an agent to a peptide linker fused to the MHC complex in accordance with well-known techniques. Examples of useful agents include photometrically detectable labels such as, e.g., a dye or a fluor; an enzyme (such as, e.g., β-galactosidase, alkaline phosphatase, or horseradish peroxidase; which enzymes are capable of forming a photometrically detectable label). See generally U.S. Pat. No. 5,434,051 for a discussion of suitable photometrically detectable labels. Alternatively, the agents can be conjugated to the polyspecific MHC complexes disclosed herein by a variety of other means not involving a peptide linker, some of which means are disclosed below.

Further, the MHC complexes of the invention can be post-translationally modified if desired by e.g., carbohydrate or fatty acid addition. For example, the MHC complexes can be modified by glycosylation. Glycosylation sites on proteins are known in the art and are typically either N-linked (asparagine-linked) or O-linked (serine- or threonine-linked). Such glycosylation sites can be readily identified by inspection of the MHC complex protein sequence. The MHC complexes can be glycosylated by suitable eukaryotic cells as evidenced by, e.g., SDS-PAGE gel electrophoresis. SDS-PAGE gel electrophoresis and other related methods can be combined with conventional biochemical techniques such as, e.g., enzymatic digestion, to detect carbohydrate bound to the MHC complexes of the invention. Examples of preferred digestive enzymes include, e.g., endoglycosidases, and exoglycosidases available, e.g., from New England Biolabs (Beverly Mass.) and used in accordance with the manufacturer's instructions. Accordingly, MHC complexes of the invention can be readily analyzed for the presence of carbohydrate groups, particularly oligosaccharide groups. In some instances, it may be useful to obtain substantially pure MHC complexes of the invention in glycosylated form. Particularly, such glycosylated MHC complexes may exhibit less in vivo degradation in some settings when administered as a therapeutic agent, thereby increasing circulating half-life (see e.g., Goto, M. et al. *Bio/Technology* 6:67 (1988)). Accordingly, the methods of the present invention are well-suited for obtaining large-scale quantities of substantially pure glycosylated MHC complexes.

The MHC complexes of the invention can be purified if desired by one or a combination of techniques. Exemplary methods for the production of MHC complexes include expression in cells capable of expressing the complexes. For example, the MHC complexes can be obtained by expressing the MHC complex in insect cells e.g., a baculovirus-based protein expression system. See, e.g., Example 5 which follows. Suitable insect cells include those capable of being infected by a baculovirus such as, e.g., cells derived from *Spodoptera freugiperda* (e.g., SF9 cells) or *Trichoplusia ni*. (see e.g., Ausubel et al. *Current Protocols in Molecular Biology*, John Wiley & Sons, New York, 1989; Summer and Smith, *A Manual of Methods for Baculovirus Vectors and Insect Cell Culture Procedures*: Texas Agricultural Experimental Station Bulletin No. 1555, College Station, Texas (1988); D.R. O'Reilly et al., *Baculovirus Expression Vectors: A Laboratory Manual*, W.H. Freeman & Co., New York (1992). Suitable insect cells are also preferably capable of producing foreign proteins on a large-scale in, e.g., spinner flasks, roller bottles, multiple tissue culture plates, a bioreactor, or a fermentor.

In addition to expressing the MHC complexes of the invention in insect cells, other eukaryotic cells such as mammalian cells can be used to produce the MHC complexes. See for instance, Example 6 which follows. Generally, the methods include introducing a suitable mammalian expression vector encoding the MHC complex in a mammalian cell, and culturing the cell under conditions which support the production of the MHC complex. Suitable mammalian cells are those preferably capable of expressing large-scale quantities of foreign proteins in, e.g., spinner flasks, roller bottles, multiple tissue culture plates, a bioreactor or a fermentor.

The term "vector" as used herein (including "expression vector") means any nucleic acid sequence of interest capable of being incorporated into a host cell resulting in the expression of a nucleic acid of interest. Vectors can include, e.g., linear nucleic acid sequences, plasmids, cosmids, phagemids, and extrachromosomal DNA. Specifically, the vector can be a recombinant DNA. Also used herein, the term "expression", or "gene expression", is meant to refer to the production of the protein product of the nucleic acid sequence of interest, including transcription of the DNA and translation of the RNA transcript.

Other suitable cells for expressing the MHC complexes of the invention include prokaryotes such as, e.g., *E. coli, Bacillus subtilus*; and other eukaryotes such as animal cells and yeast strains, e.g., *S. cerevisiae* and *S. pombe*. Mammalian cells are often preferred, e.g., J558, NSO, COS, CV-1, SP2-O, CHO, HeLa, p3-X63Ag8, or myeloma cells. See Examples 4–6 which follow.

In addition to particular cells disclosed herein, other cells can be tested for capacity to express the MHC complexes. In general, it is possible to test nearly any plant, insect, mammalian, bacterial, fungal or yeast cell for the capacity to express, preferably on a large-scale, the MHC complexes disclosed herein.

For example, one method of testing a cell for expression of an MHC complex of the invention is as follows. A protein expression experiment is performed whereby a DNA sequence encoding the MHC complex of interest preferably in a suitable vector is introduced into the cell by, e.g., transformation or transfection. After introduction of the DNA sequence encoding the MHC complex of interest, the host cell is then cultured under conditions which favor the production of the MHC molecule. Protein expression is then monitored by e.g., ELISA, Western blot or SDS-PAGE gel electrophoresis, to determine if the cell expresses, either in the cell or cell culture medium, an MHC molecule exhibiting an appropriate pre-determined molecular weight. Generally, a suitable cell will be capable of producing between about 1 ng/$1\times10^6$ cells per day to 1000 ng/$1\times10^6$ cells per day or greater, as determined by, e.g., ELISA or SDS-PAGE gel.

In some instances, it may be desirable to transiently express an MHC complex of the invention in a suitable eukaryotic cell. For example, in cases where the eukaryotic cell is an insect or mammalian cell, it may be useful to transiently express the MHC complex by means of a suitable DNA expression vector.

Selection of suitable vectors for expressing the MHC complexes disclosed herein can be made empirically based on factors relating to list compatibility. For example, the vector should be compatible with, and have the proper replicon for the host that is being employed. Further the vector must be able to accommodate the DNA sequence coding for the MHC complex. Particularly with respect to the polyspecific MHC complexes of the invention, the vector may encode a portion of the polyspecific complex, e.g., one-half thereof or another pre-selected portion as desired.

More specifically, a suitable vector for replication in bacteria generally includes e.g., (i) an origin of replication functional in *E. coli* and derived e.g., from PBR322, preferably from well-known pUC19 vectors; (ii) a selectable antibiotic resistance gene, e.g., ampicillin and/or neomycin resistance gene; (iii) a transcriptional termination region, e.g., the termination region of the *E. coli* trp operon; (iv) a transcriptional promoter, e.g., a phoA, tac, tac-lac, lacZ, lac$^{uvs}$, T7, or T3 promoter; (v) a leader sequence, e.g., a pelB or ompA leader; (vi) a DNA segment encoding the MHC complex of interest and (vii) a transcriptional terminator, e.g., the T1T2 sequence from the ribosomal RNA locus of *E. coli*. As mentioned previously, the MHC complex will include a modified class II β2 chain such as a deletion of the essentially the entire chain, and/or the MHC complex will include a fused Ig-$C_L$ chain such as the murine or human Cκ fragment.

It is has been found that soluble expression of the MHC complexes of the invention can be facilitated in bacteria by specified induction conditions. By the term "induction conditions" is meant culture conditions in which an essential nutrient (e.g., an amino acid or inorganic salt such as phosphate) is depleted from the medium, thereby inducing expression of particular promoters operatively linked to sequences encoding the MHC complexes. It is thus preferred that the vector or segment encoding the MHC complex for bacterial expression be formatted to maximize expression under these induction conditions. Particular examples of host cells which can be cultured under the induction conditions include bacteria provided in examples that follow.

For example, the phoA promoter described below is an example of particularly preferred element for expressing the MHC complexes in bacteria under induction conditions where phosphate is depleted. See Example 4, which follows. A strong translation initiation sequence also can be included in the construct to enhance translation efficiency. In general, induction of the phoA promoter is rapidly initiated when phosphate in the media is used up.

DNA vectors encoding MHC complexes can be expressed in bacteria by inducing host cells over an extended growth period. Without wishing to be bound to any particular theory, it has been found that induction over approximately two to eight hours, preferably approximately four to six hours, appears to enhance expression of the MHC complexes. For example, a DNA vector was made that included a phoA promoter (strong) operably linked to sequences encoding a desired MHC complex. See examples 3 and 4 below. Host cells were then transformed with the DNA vector and phosphate in the host cell media was allowed to deplete from the media over several hours, generally approximately 2 to 10 hours, more typically 4 to 6 hours. It was found that when media phosphate is depleted the strong phoA promoter is induced, significantly increasing amounts of soluble and fully functional MHC complex.

Additional DNA vectors can be designed to express MHC complexes in eukaryotic cells. Exemplary DNA vectors are preferably formatted for replication in a bacterial host so that suitable amounts of the DNA vector can be obtained. For example, the DNA vector can generally include (i) the origin of replication functional in *E. coli*; (ii) the selectable antibiotic resistance gene; (iii) a strong viral promoter such as the cytomeglovirus (CMV) promoter and optional enhancer element, (iii) a DNA segment encoding a desired MHC complex (iv) a growth hormone polyadenlyation sequence, e.g., bovine growth hormone (bgh) polyA sequence and (v) DNA encoding a selectable eukaryotic marker such as a strong viral promoter such as the simian virus 40 (SV40) promoter linked to an antibiotic resistance gene (e.g. neomycin) fused to a viral polyadenlyation sequence (e.g., the SV40 polyA sequence). Examples of suitable DNA vectors are disclosed below in Example 6. As mentioned previously, the MHC complex will often include a modified class II β2 chain, preferably a deletion of the essentially the entire chain, and/or the MHC complex will include a fused Ig-$C_L$ chain or suitable Ig-$C_L$ chain fragment such as the murine or human Cκ fragment.

A DNA vector of the invention for use in a desired mammalian cell can be modified according to conventional techniques to optimize soluble expression in one or a variety of other mammalian cells. For example, the eukaryotic marker encoding the neomycin resistance gene described above can be replaced, e.g., by DNA encoding the thymidine kinase (TK) gene to facilitate expression of the sc-MHC fusion protein in TK- (TK deficient) mammalian cells. The DNA vector can be modified in other ways well-known in the art (e.g., changing promoters, antibiotic resistance genes, replacing the CMV promoter with an immunoglobin, SV40, adenovirus or papilloma virus promoter, etc.) to optimize MHC complex expression in a desired mammalian cell. Alternatively, the DNA sequence encoding the sc-MHC protein can be inserted into well-known vectors suitable for expression in yeast or insect cells. See e.g. Ausubel, et al. supra.

Additional DNA expression vectors for expressing the MHC complexes of the present invention in mammalian cells include DNA vectors derived from the pEE13 or pCDNA-3 vector, e.g., SCE1, in which an MHC complex is placed downstream from a suitable cytomegalovirus promoter. See examples in the published PCT applications, and Example 6 below. Other known DNA expression vectors can be used in accordance with the present invention to express the MHC complexes (see e.g., Ausubel et al. supra and Sambrook et al., supra).

A variety of standard methods can be used to introduce a DNA segment encoding a desired MHC complex or DNA vector carrying same into a desired cell. For example, the DNA segment or DNA vectorcan be introduced into a suitable cell by any acceptable route such as, e.g., calcium phosphate or DEAE dextran mediated transfection or transformation, viral or phage infection (with recombinant virus encoding the MHC complex), electroporation, liposome-mediated transfer, or biolistic transfer, in accordance with conventional techniques (see, e.g., Cockett, et al., *Bio/Technology* 8:662 (1990); Ausubel et al., supra; and Sambrook et al., supra). The cells are then cultured under conditions which support the expression of the MHC complex such as, e.g., microcarrier or hollow fiber culture systems, suspension systems, culture systems associated with roller bottles, spinner flasks, bioreactors or fermentors; whereby the selected culture system is maintained under optimal conditions of media, atmosphere and temperature. If desired, the culture conditions can be optimized for the large-scale production of desired MHC complexes. See examples 4–6 below.

In some cases, it may be desirable to propagate a eukaryotic cell that includes a vector (including a selectable marker) encoding an MHC complex under conditions which result in the chromosomal integration of the vector. Cell lines obtained by selection of the marker are particularly useful for the capacity to constitutively express the MHC complex.

MHC complexes of the present invention can include a variety of class I or class II MHC molecules. For example, referring to the soluble sc-MHC class II peptide fusion molecule illustrated in FIG. 1, the $IA^d$ β1-β2 and $IA^d$ α1-α2 class II molecules may be independently substituted with other class I (H-2 or HLA) or class II (IA, IE, DR, DQ, or DP) molecule. Alternatively, the $IA^d$ β1-β2 and $IA^d$ α1-α2 class II molecules may be independently substituted with a presenting-peptide binding portion of the class I or class II molecules. For example, FIGS. 4A and 4B show sc-MHC class II molecules comprising $IA^d$ (FIG. 3A) or DR2 (FIG. 4B) chains. Generally, the class I or class II molecule will be of known DNA sequence so that the molecule (or presenting peptide-binding portion thereof) can be made part of the MHC complex by the recombinant DNA techniques disclosed herein.

More particularly, MHC class I or II molecules of the present invention include allergy-or autoimmune-associated MHC molecules such as, e.g., HLA-DR2 (DRB1*1501) associated with multiple sclerosis (MS); HLA-DR4, HLA-DQ8, and HLA-DQ7, each associated with rheumatoid arthritis (RA); HLA-Q8 (DQB1*0302) associated with insulin-dependent diabetes mellitus (IDDM); HLA-DQw2 associated with celiac disease; IAs domain associated with experimental autoimmune encephalomyelitis in SJL/J mice; IAg7 associated with spontaneous diabetes in NOD mice; IAq associated with collagen induced arthritis in DBA/1 mice; or peptide-binding portions thereof. See Example 3 below.

Presenting peptide-binding portions of class I and class II MHC molecules can be readily identified by labeling the presenting peptide with a detectable molecule (e.g., $^{125}I$, $^{131}I$, $^{3}H$ or biotin), and contacting the class I or class II MHC fragment with the labeled presenting peptide under conditions sufficient to load the presenting-peptide to the corresponding full-length MHC molecule. Generally, a presenting-peptide binding portion of a class I or class II MHC molecule will bind at least about 50% (mole percent), more preferably, 60%, 70%, 80%, 90% or more, of the labeled presenting peptide when compared to the corresponding full-length MHC molecule under equivalent or related loading conditions. Certain presenting peptide-binding portions of certain MHC molecules also have been reported.

In general, the methods for loading a presenting peptide to an empty MHC molecule will involve incubation of the purified MHC complex with about a 20–50 fold molar excess of the presenting peptide for between about 20–60 hours at elevated temperature, e.g. about 37° C. The optimal pH of these loading reactions may vary depending upon the particular MHC class II molecule in the MHC complex and the presenting peptide used, however, generally, the pH optimum for loading presenting peptides will be between about pH 4.5 to pH 7. These methods can be readily applied to loading virtually any presenting peptide to the MHC class II complex. See Example 8 which follows. See also Stern, L. J. et al., 1992 *Cell* 68:465; Sette, A. S. et al. 1992, *J. Immunol.* 148:844.

Also, the loading pH can be optimized for a presenting peptide and an MHC complex pair by labeling the presenting peptide with a suitable detectable molecule, contacting the labeled presenting peptide to the MHC complex and then monitoring loading at the desired pH or pH range by, e.g., HPLC gel filtration membrane filtration, immunoabsorption or spin ultrafiltration. MHC complexes that exhibit loading at a particular pH or pH range can be separated from unloaded labeled peptide by standard separation techniques. Generally, the optimum pH or pH range for loading a particular presenting peptide to a class II MHC complex is that pH or pH range which results in at least about 50% (mole percent), more preferably 60%, 70%, 80%, 90% or greater of the class II MHC complex bound by the peptide.

A variety of presenting peptides can be loaded or covalently linked (e.g. recombinantly fused) to MHC complexes. For example, the OVA (323–339) and HSV-1 gD (246–261) presenting peptides can be fused or loaded to soluble sc-$IA^d$ MHC class II molecules (See for instance Examples 1 and 3 below). Other suitable presenting peptides include allergy-associated peptides such as, e.g., peptides derived from insect allergens such as, e.g., house dust mite allergen DER p I; domesticated animal allergens such as, e.g., cat allergen FeldI; plant allergens such as, e.g., ragweed allergen Amb a I and Amb a V; and neuronal sheath proteins. For example, Example 3 below provides the immunodominant MBP epitope of amino acids 84–102. Other potential presenting peptides of interest include proteolipid protein (e.g., the immunodominant epitope of amino acids 30–49, and the immunodominant epitope of amino acids 180–199, each associated with MS;), peptides derived from structural proteins such as, e.g., type II collagen associated with RA; and peptides derived from enzymes and peptide hormones such as, e.g., glutamic acid decarboxylase and insulin associated with IDDM.

An exemplary presenting peptide of an MHC complex will have from about 4 to 35 amino acids, preferably about 6 to 30 amino acids, more preferably from about 8 to 25 amino acids. Preferably, such presenting peptides are encoded by a DNA of known sequence, although the DNA sequence of such peptides can be readily determined by techniques known in the art. Other suitable presenting peptides include those suspected of being associated with an allergy, an autoimmune disease, or both an allergy and an autoimmune disease. Such peptides can be readily tested for the capacity to modulate T-cell activity in accordance with the T-cell assays disclosed below as well as in the published PCT Application Nos. WO 96/04314 and WO 97/28191.

As mentioned previously, the MHC complexes of the invention can be purified in a variety of ways. For example, substantially pure MHC complexes are generally preferred of at least 90 to 95% homogeneity, and at least 98 to 99% homogeneity are most preferred for many pharmaceutical, clinical and research applications. Once purified partially, or to the homogeneity as desired in a preparation, the MHC complex should be substantially free of contaminants for therapeutic applications.

A variety of other purification methods are suitable for the sc-class II MHC molecules and polyspecific MHC molecules disclosed herein. For example, tags such as EE or others known in the field such as myc can be fused to a sc-class II MHC molecule or polyspecific MHC molecule of interest to make "tagged" complexes. Such "tagged" complexes can be purified by several known immunoaffinity methods such as chromatography employing a metal-losepharose support or other chromatographic support comprising an antibody or antigen-binding fragment thereof, preferably a monoclonal antibody fragment, that specifically binds the tag and, indirectly, the attached MHC molecule. Still other known protein purification methods can be employed to purify the "tagged" molecules, e.g., immuno-precipitation. Examples of such methods are described in Example 7, below.

In most cases, the MHC complexes of the invention will be capable of modifying the activity of immune cells such as T-cells. Typically, a suitable presenting peptide is chosen for combining with a desired MHC complex (by loading or recombinant means) to activate peptide-specific T-cell responses (e.g., cytokine secretion). Alternatively, the presenting peptide can be selected to suppress T-cell activity, e.g., by inducing apoptosis, in peptide-specific T-cells in accordance with methods disclosed herein. Several assays for detecting the biological activity of the MHC complexes disclosed herein are described below. See examples 2, 9–13 below.

More particularly, the MHC complexes of the present invention are useful for a number of therapeutic and related applications, including modulating various immune system responses such as apoptosis, anergy, cytokine release, immunosuppression and immune cell induction. Of particular interest are those immune system responses directly or indirectly impacting T-cells. For example, MHC complexes bearing fused (covalently linked) or non-covalently loaded presenting peptides can be tested for capacity to suppress immunoreactive T-cells such as in accordance with the procedures illustrated in Example 11 which discloses screening methods to detect inhibition of Ig class switching and for inhibition of T-cell expansion in vivo. These methods are readily adapted to test nearly any MHC complex of the invention for the capacity to suppress immunoreactive T-cells in vivo.

For certain therapeutic applications, a DNA expression vector encoding a desired MHC molecule of the invention linked to the presenting peptide can be administered for in vivo expression of the MHC fusion complex. Such an approach avoids costly purification steps typically associated with preparation of recombinant proteins and avoids the complexities of antigen uptake and processing associated with conventional approaches. See example 12 which follows.

The invention also includes methods for in vitro identification of peptides recognized by a T-cell receptor, including peptides that can induce T-cell development as well as peptides that can antagonize T-cell receptors, i.e. T-cell receptor (TcR) antagonists or partial agonists.

Another method for suppression of an immune response provides for administration of an effective amount of one or more of the polyspecific MHC complexes disclosed herein which contain a presenting peptide that is a T-cell antagonist or partial agonist.

It has been shown that peptide-MHC complexes on the surface of APCs will only induce the clonal expansion of a reactive T-cell line specific for the MHC bound peptide if the APCs also deliver a co-stimulatory signal. In the absence of co-stimulatory signals delivered by APCs, these reactive TH cells are believed to be induced to a state of anergy. Soluble heterotrimeric peptide/MHC class II complexes isolated from APCs have been shown to suppress TH cell immune responses (Sharma, S. D. et al.,1991, *Proc. Natl. Acad. Sci. USA* 88:11465–11469; Nicolle, M. W., 1994, *J. Clin. Invest.* 93:1361–1369).

An MHC complex disclosed herein comprising a presenting peptides that is a T-cell receptor antagonist or partial agonist, can be administered as a soluble complex lacking co-stimulatory signals.

Further, an MHC complex disclosed herein comprising a modified class II-$\beta$2 domain that alters binding to the CD4 a receptor can also act to induce T-cells into an anergic state.

Alternatively, administration of a MHC complex of the invention can take the form of an effective amount of a DNA sequence comprising a DNA vector encoding a "full-length" MHC fusion complex, i.e., a complex that contains one or more full-length MHC proteins including the transmembrane portion and a presenting peptide with antagonist or partial agonist activity covalently linked to the MHC molecule.

As disclosed in said PCT application No. WO 96/04314, sc-MHC class I and II molecules can be used to detect and characterize peptides. For example, the invention includes a method that can be used to map an uncharacterized epitope for T-cells as follows: sequences encoding either a library of random peptides or selected peptides can be cloned into the presenting peptide position of an expression vector system of the invention such as those identified above that contains a DNA sequence encoding the sc-MHC complex and, optionally, a DNA sequence coding for a linker sequence. Suitably, restriction fragments of an appropriate cDNA or genomic DNA library (see Sambrook, et al., supra, Ausubel et al. supra) are used as the source of the sequences inserted into the expression vector or, alternatively, selected oligonucleotides such as synthetic oligonucleotides of known sequence are used as the inserted sequences. Suitable hosts, such as mammalian cells and others identified above, are transformed or transfected with the vector containing the gene fusion, i.e. the sequence coding for the MHC molecule linked to sequence coding for the additional peptide. Transformants are cultured under suitable conditions and the cells screened for expression of fusion complex of interest that reacts with T-cell clones as determined by assays disclosed below. Reactive colonies can then be picked and the vectors isolated. Sequence analysis of the DNA insert would reveal which of the cloned peptide sequences corresponded to the epitope(s) recognized by the T-cell clone. Empty sc-MHC molecules can be used in the same way except that the peptides are loaded onto the empty molecule rather than adding the peptide by recombinant methods. Related uses of the polyspecific MHC complexes disclosed herein are within the scope of the present invention with the proviso that for some polyspecific MHC complexes, more than one suitable vector will be employed, which vector will encode a suitable portion of the polyspecific MHC complex.

The ability of sc-MHC molecule (with a loaded or fused presenting peptide) to modulate the activity of a T-cell receptor (including inactivation of the T-cell responses) can be readily determined by an in vitro or in vivo assay. Typically T-cells for the assays will be provided by transformed T-cell lines such as T-cell hybridomas or T-cells which are isolated from a mammal, e.g., from a human or from a rodent such as a mouse. Other suitable T-cells include: 1) T-cell hybridomas which are publicly available or can be prepared by known methods, 2) T helper cells, and 3) T cytotoxic cells, preferably cytotoxic CD4+ cells. T-cells can be isolated from a mammal by known methods. See, for example, R. Shimonkevitz et al., *J. Exp. Med.*, 158:303 (1983) and the examples which follow. Examples of suitable in vitro assays have been disclosed in the published PCT Application Nos. WO 96/04314 and WO 97/28191. Particularly, the published PCT applications disclose assays and methods of use for sc-MHC class II molecules including empty or loaded peptide binding sites as well as molecules comprising recombinantly fused presenting peptides. As will be understood by the following, the assays and methods of use disclosed in the published PCT Applications can be readily adapted for use with the MHC complexes of the present invention. Related uses of the polyspecific MHC complexes of the present invention have been disclosed previously and are within the scope of the present invention.

There follows an exemplary assay to determine if a MHC complex of the invention comprising a fused peptide is capable of modulating the activity of T-cells. It will be understood that the assay is suitable for a variety of MHC complexes such as those loaded MHC complexes disclosed herein. The assay is generally conducted as follows, by the sequential steps 1–4 below. T-cells suitably express a marker that can be assayed and that indicates T-cell activation, or modulation of T-cell activity after activation. Thus, e.g., as disclosed in Examples 2, and 9 below, the murine T-cell hybridoma DO 11.10 that express interleukine-2 (IL-2) upon activation can be employed. IL-2 concentrations can be measured to determine if a particular presenting peptide is capable of modulating activity of this T-cell hybridoma. Such a suitable assay is conducted by the following sequential steps:

1. T-cells carrying the T-cell receptor specific to the peptide/MHC complex are obtained such as from a T-cell hybridoma of interest or by isolating from a mammal.

2. The T-cells are cultured under conditions that allow proliferation.

3. The proliferating T-cells are contacted with a selected MHC fusion complex.

4. The T-cell are contacted with the antigen presenting cells to provide signal necessary for activation and assayed for a marker, e.g. IL-2 production is measured. An increase in IL-2 production, e.g., a 100 percent or greater increase in IL-2 production after a period of 24 hrs., more typically a 1000 percent or greater increase in IL-2 production after a period of 24 hrs., indicates the MHC fusion complex modulates the activity of the T-cells and can suppress an immune response. Example 9 which follows exemplifies such an assay. The assay is suitably employed for analysis of activity of soluble "truncated" MHC complexes that do not contain a transmembrane portion. In addition, the assay is suitably employed for identification of MHC fusion complexes that contain a covalently linked presenting peptide that functions as a T-cell receptor antagonist or partial agonist. The assay is also conveniently adapted for use with loaded MHC complexes of the invention.

The T-cells employed in the assays are incubated under conditions suitable for proliferation. For example, a DO11.10 T-cell hybridoma is suitably incubated at about 37° C. and 5% $CO_2$ in complete culture medium (RPMI 1640 supplemented with 10% FBS, penicillin/streptomycin, L-glutamine and $5 \times 10^{-5}$ M 2-mercaptoethanol). Serial dilutions of MHC fusion complex can be added to the T-cell culture medium. Suitable concentrations of the MHC fusion complex added to the T-cells typically will be in the range of from $10^{-12}$ to $10^{-6}$ M. T-cell activation signals are provided by antigen presenting cells that have been loaded with the appropriate antigenic peptide. It is believed that use of antigen dose and APC numbers giving slightly submaximal T-cell activation is preferred to detect inhibition of T-cell responses with MHC fusion complexes. A decrease in production of IL-2 following contact with the MHC fusion complex indicates the fusion complex modulates activity of the T-cells and can suppress immune response.

Alternatively, rather than measurement of an expressed protein such as IL-2, modulation of T-cell activation can be suitably determined by changes in antigen-dependent T-cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T-cell proliferation. This assay is not suitable for T-cells that do not require antigen presentation for growth, e.g., T-cell hybridomas. It is suitable for measurement of modulation by the MHC fusion complexes of T-cell activation for untransformed T-cells isolated from mammals. A decrease in the level of T-cell proliferation following contact with the MHC fusion complex indicates the fusion complex modulates activity of the T-cells and can suppress immune response. The in vitro T-cell proliferation assay is preferred for measuring the effects of MHC. fusion complexes on antigen-specific changes in T-cell clonal expansion in vivo.

These in vitro assays can be employed to select and identify peptide(s), coded by DNA from a random library or other oligonucleotides, that are capable of modulating the activity of T-cell receptor (including activation or inhibition of T-cell development). Specifically, DNA sequences encoding either a library of random peptides or selected peptides can be cloned into the presenting peptide position of an expression vector system such as those identified above that contains a DNA sequence encoding a MHC molecule and, optionally, a DNA sequence coding for a linker sequence. Suitably, restriction fragments of an appropriate cDNA of genomic DNA library (see Sambrook, et al., supra) are used as a source of the sequences inserted into the expression vector or, alternatively, selected oligonucleotides such as synthetic oligonucleotides of known sequence are used as the inserted sequence. Suitable hosts, such as a mammalian cells and others identified above, are transformed with the vector containing the gene fusion, e.g., the sequence coding for the MHC complex linked to sequence coding for the presenting peptide. Transformants are cultured under suitable conditions and the cells are screened for expression of the MHC complex of interest by contacting same with selected T-cells. Assays described above, e.g., measurement of IL-2 production or T-cell proliferation, are employed to determine if contact with the MHC complex modulated T-cell activation. For example, an increase in IL-2 production of APC-stimulated T-cells identifies those MHC fusion complexes that modulate activity of the T-cells. Alternatively, the in vitro assays can be employed to identify multivalent MHC complexes described above, that contained presenting peptides that increase T-cell responses.

In vivo assays also may be suitably employed to determine the ability of a MHC complex to modulate the activity of T-cells, including the ability to inhibit or inactivate T-cell development. For example, an MHC fusion complex can be assayed for its ability to inhibit immunoglobulin class switching (i.e. IgM to IgG) (see, e.g., P. Linsley et al., Science, 257:792–795 (1992)). Such an assay is specifically described in Example 13 which follows.

Diagnostic methods of using the MHC complexes of the invention including the MHC fusion molecules are also provided including in vivo diagnostic imaging and HLA typing (see, e.g., A. K. Abbas, Cellular and Molecular Immunology, page 328 (W. B. Saunders Co. 1991)). For example, for in vivo imaging applications, a MHC fusion molecule that has a radioactive label (e.g., $^{125}$I, $^{32}$P, $^{99}$TC) or other detectable tag can be administered to a mammal and the subject scanned by known procedures for binding of the MHC molecule. Such an analysis of the mammal could aid in the diagnosis and treatment of a number of disorders including e.g. undesired immune responses as disclosed herein.

The MHC complexes of the invention comprising empty peptide binding domains, e.g., the empty sc-MHC class II molecules disclosed herein, can be used to screen for presenting peptides which non-covalently bind the peptide binding groove or cleft of the MHC molecule. Such screens are useful for identifying those presenting peptides which can bind particular MHC molecules e.g., MHC class II molecules such as IA$^d$, DR1, IE, DP, and DQ. As an illustrative example, the sc-IA$^d$/blank molecule can be modified with a detectable tag (e.g., $^{125}$I, biotin or another protein tag disclosed herein) and then used to screen a random peptide library. Procedures for tagging proteins and screening libraries are well known [see, e.g., Sambrook et al., supra, and Ausubel et al., supra, John Wiley & Sons, New York, 1989; herein incorporated by reference]. Any one of several random peptide libraries can be suitably employed [see, e.g., J. Scott et al., Science, 249:386 (1990); J. Devlin et al., Science, 249:404 (1990); S. Cwirla et al., PNAS (USA), 87:6378 (1990); J. Hammer et al., J. Exp. Med., 176:1007 (1992); D. O'Sullivan et al., J. Immunol., 147:2663 (1991)]. Peptides which bind the sc-IA$^d$/blank molecule can be used to make the corresponding loaded molecule. The loaded molecule could then be tested in any T-cell assay described herein to see if the identified peptide is capable of modulating T-cell activity.

Assays also may be employed to evaluate the potential use of an MHC complex of the invention for treatment of an immune disorder. For example, experimental allergic encephalomyelitis (EAE) is an autoimmune disease in mice and a recognized model. for multiple sclerosis. A suitable mouse strain can be treated to develop EAE and then a MHC fusion complex administered and the animal evaluated to determine if EAE development is inhibited or prevented after administration of the MHC fusion complex. Such an assay is specifically described in the published PCT application Nos. WO 96/04314 and WO 97/28191.

The ability of an MHC complex of the invention to induce an immune response, including vaccination against a targeted disorder, may be readily determined by an in vivo assay. For example, an MHC complex of the invention including a fused recombinant peptide, or DNA coding for a MHC fusion complex, can be administered to a mammal such as a mouse, blood samples obtained from the mammal at the time of initial administration and several times periodically thereafter (e.g. at 2, 5 and 8 weeks after administration of the fusion complex or DNA). Serum is collected from the blood samples and assayed for the presence of antibodies raised by the immunization. Antibody concentrations may be determined. Examples 12 and 13 which follows specifically describe such an assays.

In some cases it will be useful to directly administer a DNA construct coding for an MHC complex of the invention, particularly those including a fused presenting peptide, to express the complex within cells of the subject. As an example, DNA carrying the coding regions of the MHC complex comprising a fused presenting peptide, suitably under the control of an appropriate promoter such as the CMV promoter and optional enhancer, is injected directly to skeletal muscle of the subject. To ensure the display of the MHC fusion molecules will induce an immune response in the subject, DNA vectors that code for a co-stimulatory factor is preferably co-administered to the subject with the DNA coding for the MHC-presenting peptide fusion. Preferred co-administered DNA vectors include e.g. those that comprise either the coding region of CD80 or CD86 under the control of the CMV promoter. The expressed CD80 and CD86 protein can provide the co-stimulatory signal to assist the initiation of the immune response.

Such an approach for induction of an immune response in a subject such as a mammal offers significant advantages over prior approaches. The initial step in the presentation of a foreign protein antigen is the binding of the native antigen to an antigen presenting cell (APC). After binding to APCs, antigens enter the cells, either by phagocytosis, receptor-mediated endocytosis or pinocytosis. Such internalized antigens become localized in intracellular membrane-bound vesicles called endosomes. After endosome-lysosome fusion, the antigens are processed into small peptides by cellular proteases located in lysosomes. The peptides become associated with the α and β chains of MHC class II molecules within these lysosomes. These MHC class II molecules, previously synthesized in the rough endoplasmic reticulum, are sequentially transported to the Golgi complexes and then to the lysosomal compartment. The peptide-MHC complex is presented on the surface of APCs for T and B cell activation. Therefore, the accessibility of proteolytic processing sites within the antigen, the stability of the resultant peptides in the lysosome and the affinities of the peptides for MHC molecules are determining factors for the immunogenicity of a particular epitope. These factors can not be changed by administration of adjuvants. Direct expression of the MHC fusion complexes (i.e. MHC directly covalently linked to the presenting peptide), however, should bypass such complications and induce immune response against the epitope carried on the MHC fusion molecules.

However, rather than directly administering DNA coding for an MHC complex to a subject, host compatible antigen presenting cells into which such DNA has been introduced may be administered to the subject. That is, DNA coding for one or more MHC complexes of the invention may be introduced into host compatible antigen presenting cells and such transformed or transfected antigen presenting cells can be administered to the targeted host, and with the site targeted where the most efficient interaction with the appropriate T-cell would take place. Upon administration to a subject, such engineered cells can then express in vivo on the cell surface the MHC complex coded for by the DNA. Such engineered cells can be administered to a subject to induce an immune response or alternatively to suppress an immune response, as disclosed herein, depending on the expression of other co-stimulatory signals of the cells. That is, if upon administration the cells can provide an MHC complex in the absence of an effective amount of co-stimulatory signal(s), or in the presence of an effective amount of tolerance-inducing signal(s) or provide a MHC complex that contains a presenting peptide with antagonist or partial agonist activity, the cells can be administered to a host to suppress an immune response. For example, an effective amount of tolerance-inducing signal can be provided by factors expressed on the surface of cells that interact with tolerance-inducing receptors, such as CTLA-4 or Fas, on T-cells. Alternatively, if the cells can provide a MHC complex in the presence of an effective amount of co-stimulatory signal(s), e.g. if a T-cell co-stimulatory factor such as B7 or B7-2 is expressed on the surface of the cells, the cells can be administered to a mammal host to induce an immune response in the mammal, as disclosed herein. It may be preferred to construct a single expression that codes for both chains of a MHC complex as well as for a T-cell costimulatory factor if employed, as discussed above, and introduce that vector into a host compatible APC to prepare the cells for administration.

As will be recognized by those in the art, the term "host compatible" antigen presenting cells means antigen presenting cells that are of the same haplotype as that of the subject or "host" to which the cells are administered. Preferably the transformed host compatible antigen presenting cells are those that can migrate to lymph nodes of the subject to which the cells have been administered and, at that site, express the MHC complex.

The MHC complexes of the invention and DNA constructs that encode such complexes have a number of therapeutic applications. For example, MHC class II fusion complexes can be administered to suppress an immune response of a mammal, e.g., to treat a mammal including a human that suffers from or is susceptible to an autoimmune disorder such as e.g. multiple sclerosis, insulin-dependent diabetes mellitus, rheumatoid arthritis and the like. Also suitable for treatment are those subjects suffering or likely to suffer from an undesired immune response e.g. patients undergoing some type of transplant surgery such as transplant of heart, kidney, skin or other organs. In such situations, a treatment protocol may suitably be commenced in advance of the surgical procedure.

A number of distinct approaches can be employed to suppress an immune response of a mammal in accordance with the invention.

Specifically, as discussed above, it has been shown in the published PCT Application that an MHC molecule will only induce clonal expansion of a T-cell line specific if co-stimulatory signal(s) such as from antigen presenting cells are also delivered. In the absence of co-stimulatory signals, or at least in the absence delivery of an T-cell proliferation effective amount of such T-cell co-stimulatory signal(s), the T-cells will be induced to a state of anergy or apoptosis resulting in clonal deletion.

Accordingly, one treatment method for suppression of an immune response provides for the administration of an effective amount of one or more MHC class II complexes of the invention such as MHC fusion complexes, in the substantial absence of any costimulatory signal(s) to thereby induce anergy for specific T-cells and effectively suppress an undesired immune response. For example, a "truncated" soluble MHC complex can be administered, i.e. the MHC complex does not contain a transmembrane portion. The presenting peptide of the administered soluble MHC fusion complex can be selected that are specific for T-cells of an undesired immune response to induce a state of anergy with respect to those T-cells. Such presenting peptides can be readily identified and selected by the in vitro protocols identified above.

The MHC complexes of the invention can be suitably administered to a mammal by injection, e.g., intraperitoneal or intravenous injection. Topical administration, e.g., eye drops, and administration through nasal and lung inhalers also should be possible. An MHC complex, at least those complexes used in therapeutic applications, may be produced in mammalian cells and purified prior to use so it is essentially or completely free of any bacterial or pyrogens. The optimal dose for a given therapeutic application can be determined by conventional means.

The MHC complexes of the invention, including those complexes comprising a fused presenting peptide may be suitably administered to a subject (particularly mammal such as human or livestock such as cattle) in treatment or pharmaceutical compositions which comprise the fusion complex. Such pharmaceutical compositions of the invention are prepared and used in accordance with procedures known in the art. For example, formulations containing a therapeutically effective amount of an MHC complex may be presented in unit-dose or multi-dose containers, e.g., sealed ampules and vials, and may be stored in a freeze dried (lyophilized) condition requiring only the addition of the sterile liquid carrier, e.g. water for injections, immediately prior to use. Liposome formulations also may be preferred for many applications. Other compositions for parenteral administration also will be suitable and include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Another treatment method for suppression of an immune response provides for the administration of an MHC complex of the invention that contains a modified class II-β2 domain that fails to efficiently recruit the TCR-coreceptor CD4 on T-cells. Engaging the T-cell receptor with the peptide-MHC complex while blocking association with CD 4 results in partial agonist T-cell signaling and T-cell anergy (Madrenas, et al., *J. Exper. Med.*, 185:219–229 (1997)). The MHC fusion complex may be loaded with presenting peptides or be covalently linked to presenting peptides as described above. The MHC fusion complex may be a truncated form lacking all or part of the transmembrane portion and be administered as a soluble protein as described above. Alternatively, the MHC fusion complex may be full length, i.e., will contain a transmembrane protein. Treatment with these complexes will comprise administration to a mammal an effective amount of DNA sequence that comprises a DNA vector encoding the full length MHC fusion complex of the invention that contains a modified class II-β2 domain. Alternative, treatment will comprise administration to a mammal an effective amount of cells that express on their surfaces the full length MHC fusion complex of the invention that that contains a modified class II-β2 domain.

Another treatment method for suppression of an immune response provides for the administration of a polyspecific MHC complex of the invention that contains a MHC complex and one or more additional binding activities that interacts with tolerance-inducing receptors on T-cells. For example, the additional binding activities may be defmed by proteins or peptides, such as single-chain antibodies or FasL, that specifically interact with T-cell surface proteins, such as CTLA-4 or Fas. Engagement of CLTA-4 and Fas result in either down-regulation of T-cell functions or T-cell apoptosis. The MHC complex may be loaded with presenting peptides or be covalently linked to presenting peptides as described above. The polyspecific MHC complex may be a truncated form lacking transmembrane portion and be administered as a soluble protein as described above.

Yet another treatment method for suppression of an immune response provides for administration of an MHC complex of the invention that contains a covalently linked presenting peptide that is a T-cell receptor antagonist or partial agonist (see A. Sette et al., *Annu. Rev. Immunol.*, 12:413–431 (1994)). The MHC fusion complex may be a truncated form and be administered as a soluble protein as described above. Alternatively, the MHC fusion complex may be full length, i.e. will contain a transmembrane portion. Treatment with these complexes will comprise administration to a mammal an effective amount of a DNA sequence that comprises a DNA vector encoding the full length MHC fusion complex of the invention and a presenting peptide that is a TCR antagonist or partial agonist. See, e.g., the discussion above and Examples 3, 11–13 which follow for suitable means of preparation of such MHC fusion complexes and use of same for immunosuppressive therapy. Presenting peptides that are TCR antagonists or partial agonists can be readily identified and selected by the in vitro protocols identified above. A MHC fusion complex that contains a presenting peptide that is a T-cell receptor antagonist or partial agonist is particularly preferred for treatment of allergies and autoimmune diseases such as multiple sclerosis, insulin-dependent diabetes mellitus and rheumatoid arthritis.

Further, as discussed above and in said PCT application No. WO 96/04314, host compatible antigen presenting cells into which DNA coding for an MHC complex of the invention has been introduced may be administered to a subject to suppress an immune response. Upon administration the cells express the MHC complex in the absence of an effective amount of T-cell co-stimulatory signal(s), i.e. such that T-cell anergy is induced, and/or the administered cells express an MHC fusion complex that contains a linked presenting peptide with antagonist or partial agonist activity.

Different immunosuppressive therapies of the invention also may be used in combination as well as with other known immunosuppressive agents such as anti-inflammatory drugs to provide a more effective treatment of a T-cell-mediated disorder. For example, immunosuppressive MHC fusion complexes that can be used in combination with anti-inflammatory agents such as cortico steroids and nonsteroidal drugs for the treatment of autoimmune disorders and allergies.

The invention also provides methods for invoking an immune response in a mammal such as a human, including vaccinating a mammal such as a human against an infectious agent or a targeted disorder such as cancer, particularly a melanoma cancer, or other disorder such as malaria.

These methods include administering to a mammal an effective amount of a DNA sequence that comprises a DNA vector that codes for an MHC complex of the invention that contains a transmembrane portion, and/or administration of such a MHC fusion complex that contains a transmembrane portion and/or administration of host compatible antigen presenting cells that contain such DNA that code for such MHC complexes. Preparation of expression vectors of MHC complexes is described above and in Examples 1–3 which follow. Methods for administration of plasmid DNA, uptake of that DNA by cells of the administered subject and expression of protein has been reported (see J. Ulmer et al., *Science*, 259:1745–1749 (1993)).

In an illustrative method, the DNA that codes for an MHC complex is administered to a mammal together with a DNA sequence coding for a T-cell costimulatory factor such as DNA coding for CD80 or CD86. The CD80 gene and expression thereof is described in D. Harlan et al., *Proc. Natl. Acad. Sci.* USA, 91:3137–3141 (1994). Upon uptake of that DNA by the cells of the subject, the T-cell co-stimulatory factor will be expressed and can provide the co-stimulatory signal(s) and thereby assist in the initiation of the immune response. See the published PCT application and the pending U.S. application for disclosure relating to construction of expression vectors containing CD80 or CD86 genes.

While administration of DNA coding for an MHC complex to a mammal such as a human as discussed above is a method for invoking an immune response in the subject, MHC complexes also may be suitably administered by other routes. Thus, as discussed above, host compatible antigen presenting cells into which DNA coding for an MHC complex has been introduced may be administered to a subject to induce an immune response. Upon administration the cells express an MHC complex in the presence of an effective amount of T-cell co-stimulatory signal(s) such as CD80 or CD86 genes to invoke an immune response, and/or the administered cells express a full length MHC complex that is capable of invoking an immune response, e.g. as shown by an increase in T-cell proliferation such as by procedures detailed in Examples which follow.

Alternatively, a suitable MHC complex of the invention capable of invoking an immune response may be directly administered to a subject, e.g. a MHC complex that contains a covalently linked antigenic presenting peptide which can stimulate or induce T-cell proliferation. Typically, the MHC complex will include a recombinantly fused presenting peptide although empty or loaded complexes may be used for some applications as desired.

Another treatment method for invoking of an immune response provides for the administration of an polyspecific MHC complex of the invention that contains a MHC complex and one or more additional binding activities that interact with costimulatory receptors on T-cells. For example, the additional binding activities that may be defined by proteins or peptides, such as single-chain antibodies, CD80 or CD86, that specifically interact with T-cell surface proteins, such as CD28. Costimulatory signals provided by CD28 determine the outcome of TcR engagement, since they augment T-cell proliferation and effector cell functions, such as cytokine production and cytolysis. The MHC complex may be loaded with presenting peptides or be covalently linked to presenting peptides as described above. The polyspecific MHC complex may be truncated form lacking transmembrane portion and be administered as a soluble protein as described above.

Methods of the invention for inducing an immune response, including vaccinating a subject against a targeted disorder, may be used in combination with known methods for inducing an immune response. For example, a sc-MHC class II complex of the invention, or DNA construct coding for such a MHC complex, may be administered to a subject in coordination or combination with administration of a vaccine composition, in order to boost or prolong the desired effect of such vaccine composition.

Additionally, MHC complexes of the invention, DNA vectors that encode such complexes and host compatible antigen presenting cells that contain such DNA vectors each suitably may be administered to a subject by a variety of other routes. For example, to induce an immune response, it may be preferable to administer DNA vectors that encode antigenic MHC fusion complexes, alone or together with DNA coding for a co-stimulatory factor, intradermally to a subject, by procedures known to those skilled in the art. Such administration can result in transformation of intradermal antigen presenting cells (e.g., dendritic cells) and T-cell proliferation. MHC fusion complexes and DNA vectors encoding such fusion complexes also may be administered to a subject by other routes, e.g., orally or transdermally.

In addition to treatment of human disorders, MHC complexes of the invention such as those complexes including fused presenting peptides and DNA constructs that encode such complexes will have significant use for veterinary applications, e.g., treatment of disorders of livestock such as cattle, sheep, etc. and pets such as dog and cats.

While the MHC complexes disclosed herein or DNA constructs coding for such complexes may be administered alone to a subject, they also each may be used as part of a pharmaceutical composition. Pharmaceutical compositions in general comprise one or more MHC complexes of the invention or DNA constructs coding for such complexes together with one or more acceptable carriers. The carriers must be "acceptable" in the sense of being compatible with other ingredients of the formulation and not deleterious to the recipient thereof. For example, for parenteral administration such as by an injection formulation, a sterile solution or suspension with water may be prepared, or other pharmaceutically acceptable solutions. Such pharmaceutical compositions are suitably prepared by methods known in the art.

Actual preferred amounts of a given MHC complex or DNA construct coding for same used in a given therapy will vary to the particular active compound or compounds being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests conducted e.g. with regard to the foregoing guidelines and the assays disclosed herein.

As described previously, empty MHC complexes of the invention, e.g., empty sc-MHC class II complexes, can be combined with a suitable presenting peptide to form a loaded sc-MHC complex of the invention. It will be appreciated that such loaded complexes can be suitably employed in some cases where administration of a MHC peptide fusion complex is indicated, as described above. In instances where a DNA construct encoding a MHC peptide fusion complex is used, one or more DNA constructs encoding a suitable empty single chain MHC complex may be employed, provided that appropriate conditions are provided for non-covalently binding a suitable presenting peptide to the peptide binding groove or cleft of the empty MHC molecule. Examples of conditions for the binding of a suitable presenting peptide to an empty single chain MHC molecule are discussed more fully, infra. Loaded MHC complexes of the invention, e.g., loaded MHC class II peptide fusion complexes, have use in the treatment of human, livestock and pet disorders as described above.

It will also be appreciated that the MHC complexes of the invention can be used to construct transgenic mouse strains in accordance with methods described in the published PCT application No. WO 96/04314. Such mouse strains are useful as, e.g., model systems in which the activity of specific immune cells such as T-cells can be modulated.

By the term "specific binding" or similar term is meant a molecule disclosed herein which binds another molecule, thereby forming a specific binding pair, but which does not recognize and bind to other molecules as determined by, e.g., Western blotting, ELISA, RIA, gel mobility shift assay, enzyme immunoassay, competitive assays, saturation assays or other suitable protein binding assays known in the art. See generally Ausubel et al. supra, Sambrook et al. supra, and Harlow and Lane Antibodies: A Laboratory Manual, CSH Publications, N.Y. (1988), for suitable conventional methods for detecting specific binding between proteins.

It will also be understood that by "promoter" is meant a segment of DNA to which a transcriptional enzyme complex binds prior to initiating transcription of the gene. For construction of transgenic mice, preferred promoters include the $IA^d$ promoter and the rat insulin prompter described by Ohashi et al. in Cell 65, 305–317 (1991).

All documents mentioned herein are incorporated herein by reference in their entirety.

The following non-limiting examples are illustrative of the invention.

EXAMPLE 1

Construction and Cell Surface Expression of a Single-chain Class II MHC Molecule with one TM Domain (sc-$IA^d$/OVA)

In accordance with the methods described herein, an sc-$IA^d$/OVA fusion molecule (see FIG. 1 and SEQ ID NOS: 24 and 25) was made by the following method:

Reverse transcriptase-polymerase chain reactions (RT-PCRs) were carried out to amplify $IA^d$ α and β chain gene fragments from total RNA isolated from A20-1.11 cells [K. Kim et al., *J. Immunol.*, 122:546 (1979)]. Suitable restriction enzyme sites were introduced at the each end of the gene fragments by PCR in order to facilitate cloning. DNA sequence encoding a 10 amino acid peptide linker was introduced into the 5' end of the β1-β2 gene fragment and the Kozak consensus sequence was introduced at the 5' end of the β signal sequences by PCR. The regions encoding the 24 amino acid linker and OVA antigenic peptide were generated from annealed oligonucleotides. Assembly of the PCR fragments and double-strand oligonucleotides in the pBlueScript-II vector (Stratagene) generated the sc-$IA^d$ fusion gene (see FIG. 1 and SEQ ID NO 24). For mammalian expression, the pSCT1 vector was generated by subcloning the sc/$IA^d$-OVA gene (including the a chain TM and cytoplasmic regions) downstream of the CMV promoter of pEE13 (Cell Tech). The pEE13 vector also carries a selectable glutamate synthetase gene.

The sc-$IA^d$/OVA fusion molecule was tested for cell surface expression by the following method: Plasmacytoma NS-0 cells transfected with an expression vector carrying the sc-IA$^d$/OVA fusion gene were selected and surface expression of class II molecules was examined by flow cytometry. The NS-0 cells were transfected by electroporation with linearized pSCT1 DNA carrying the sc-IA$^d$/OVA fusion gene. The cells were selected by growth in glutamine-free medium. Transfectants (i.e. T12 cells) became evident after 14–21 days and were analyzed for surface expression of class II MHC molecules. The cells were stained with FITC-conjugated anti-IA$^d$mAb (AMS-32.1 PharMingen) and fluorescence was examined by flow cytometry. An isotype matched FITC-conjugated anti-IA$^k$ mAb (10-3.6; PharMingen) was used as a negative control.

Figure 2A:
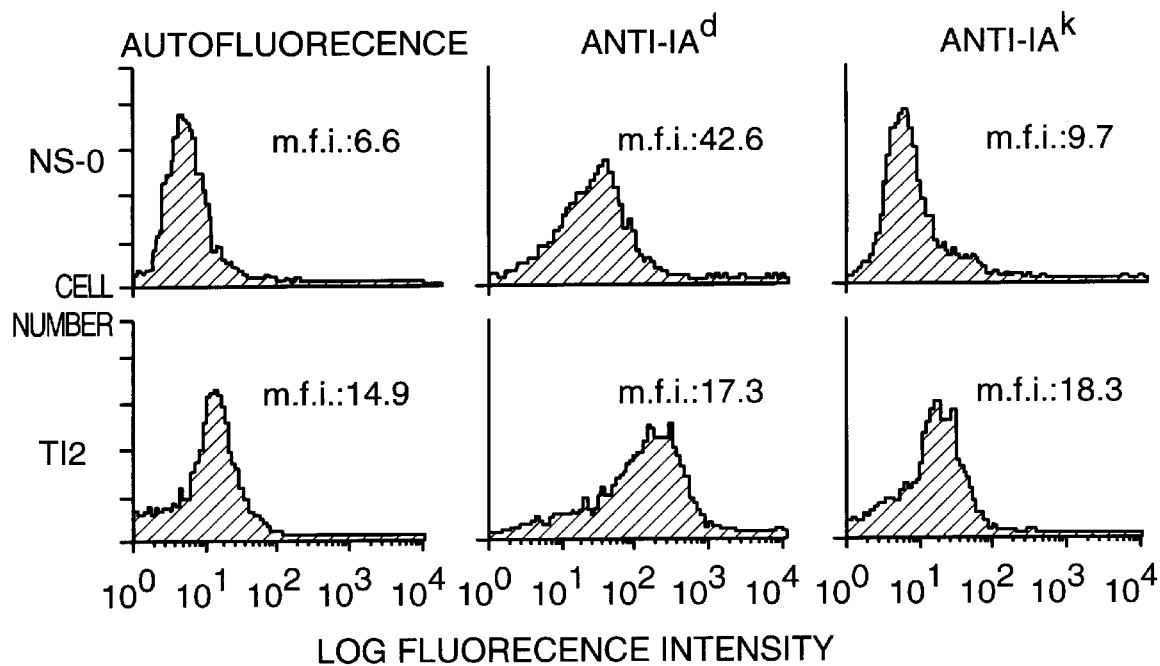
FIGS. 2A and 2B are graphs illustrating the cell surface expression (2A) and T-cell inducing activity (2B) of the sc-IA$^d$/OVA molecule.

FIG. 2A shows the cell surface expression of a functional single-chain fusion molecule. Stable transfectants were analyzed by flow cytometry using-IA$^d$ and anti-IA$^k$ mAbs. Results shown for the T12 transfectant are similar to those seen for three other independent transfectants (m.f.i.=mean fluorescence intensity). The results demonstrate an increase in sc-IA$^d$/OVA expression on the surface of cells transfected with the sc-IA$^d$/OVA expression vector. An intact β TM domain is not required for cell surface expression of class II molecules; a flexible linker connecting the β and α chains can replace the function of the β TM domain. Finally, the results also demonstrate that covalently linking the presenting peptide to a single chain MHC class II molecule facilitates stable assembly and surface expression of the MHC molecule. Linking the presenting peptide to the β chain will also allow stable assembly and cell surface expression of a single chain MHC fusion molecule.

Figure 2B:
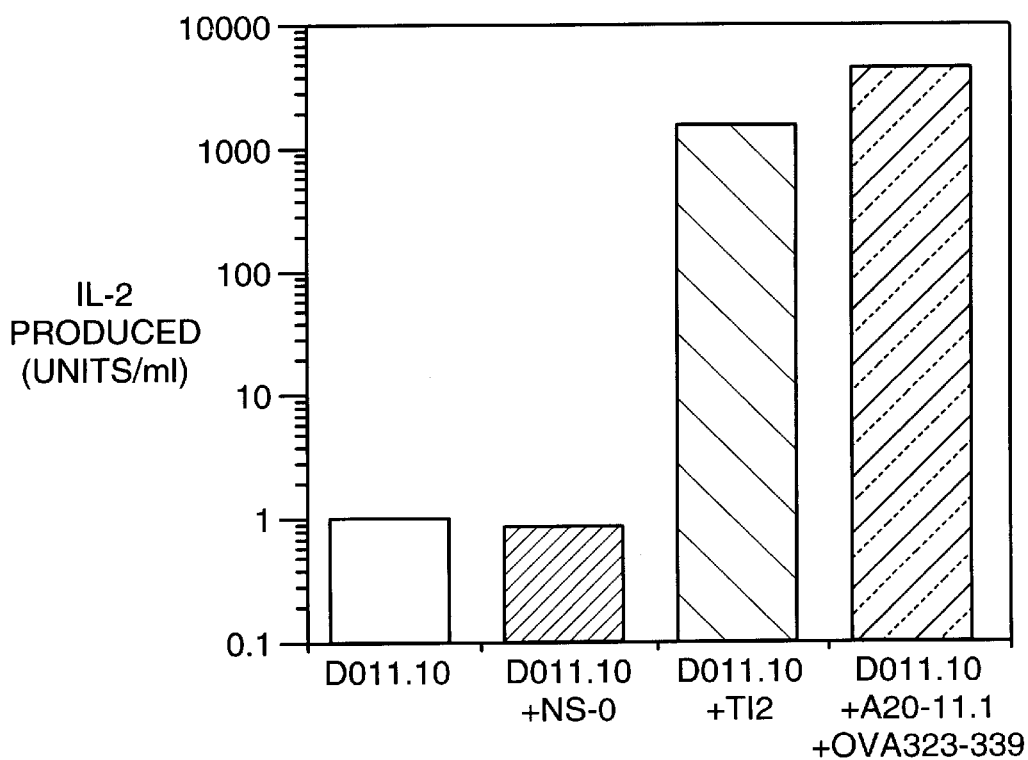

EXAMPLE 2
A Cell Surface sc-IA$^d$/OVA Fusion Complex Induces a T-cell Response in Vitro To check whether the OVA peptide folded properly into the sc-IA$^d$ fusion complex, sc-IA$^d$/OVA transfected cells were assayed for their ability to stimulate T-cells. A murine T-cell hybridoma (DO11.10) that expresses a T-cell receptor (TcR) was used. The TCR recognizes the OVA 323–339 peptide in the context of IA$^d$. When the TcRs of these cells interact with the APCs (here, sc-IA$^d$/OVA transfectants) the DO11.10 cells secrete interleukin-2 (IL-2). DO11.10 cells (2×10$^5$/well) were cultured in the presence of NS-0 cells of the T12 transfectants (1×10$^5$/well) for 24 hours and IL-2 released into the culture medium was determined by an IL-2-specific ELISA (PharMingen). The murine IA$^d$-bearing B cell lymphoma, A20-1.11 (1×10$^5$/well) was pulsed with 20 mM OVA 323–339 served as a positive control for antigen presentation [K. Kim et al., *J. Immunol.*, 122:549 (1979)]. No IL-2 was detected in the culture medium of the T12 cells alone. As shown in FIG. 2B, NS-0 cells (untransfected) failed to stimulate DO11.10 cells, whereas cells transfected with the sc-IA$^d$/OVA fusion gene strongly stimulated the release of IL-2 from DO11.10 cells. Results were similar to those observed for two other sc-IA$^d$/OVA transfectants. The extent of IL-2 secretion was comparable to those seen for IA$^d$-bearing APCs pulsed with OVA peptide. The results demonstrate that the OVA peptide folds properly within the sc-IA$^d$ fusion complex and that the folded OVA peptide in the context of IA$^d$ is recognized by the TcR on the surface of DO11.10 cells.

EXAMPLE 3
Construction of Single-chain Class II and Single-chain Class II-IgG C$_L$ Fusion Genes Two different IA$^d$-restricted peptides were used: OVA 323–339 (ISQAVHAAHAEINEAGR (SEQ ID NO: 26)) from chicken ovalbumin (Buus, S. et al. *Science* 235:1353 (1987)) and gD 246–261 (APYSTLLPPELSETP (SEQ ID NO: 27)) from HSV-1 glycoprotein D (Grammer, S. F., et al. *J. Immunol.* 145:249 (1990)). Oligonucleotides encoding these peptides were inserted between the signal peptide sequence and the peptide linker in the sc-IA$^d$ gene (see e.g., FIGS. 1 and 3A, B). The resulting fusion genes constructed encode the sc-IA$^d$ fusion protein carrying no peptide (sc-IA$^d$/blank), the OVA 323–339 peptide (sc-IA$^d$/OVA) or the gD 246–261 peptide (sc-IA$^d$/gD).

Figure 3A:
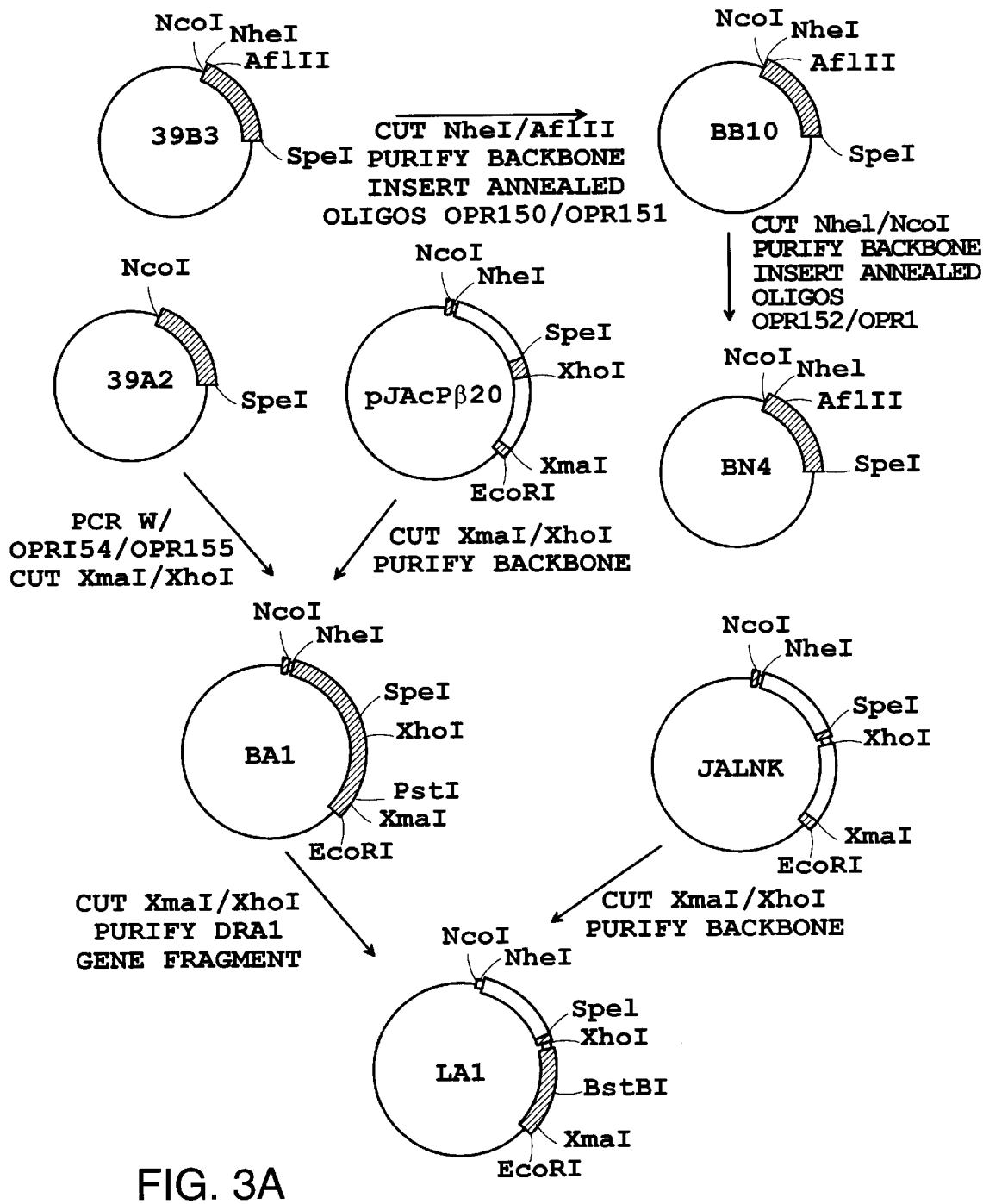
FIGS. 3A–3N are drawings outlining synthesis of the DNA vectors SDE3, pMB959, pMB808, pIADK and pDRHK.
Figure 3B:
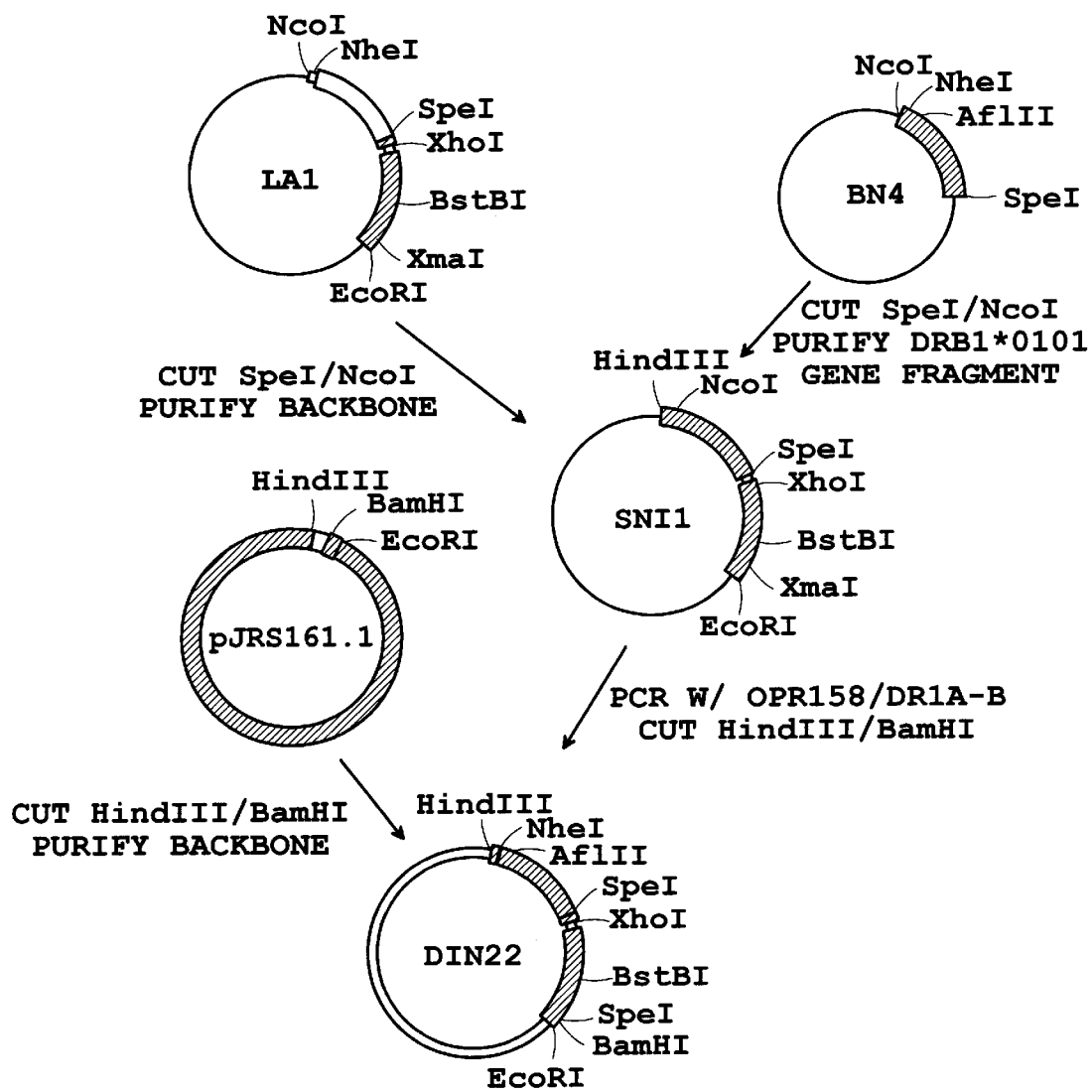
Figure 3C:
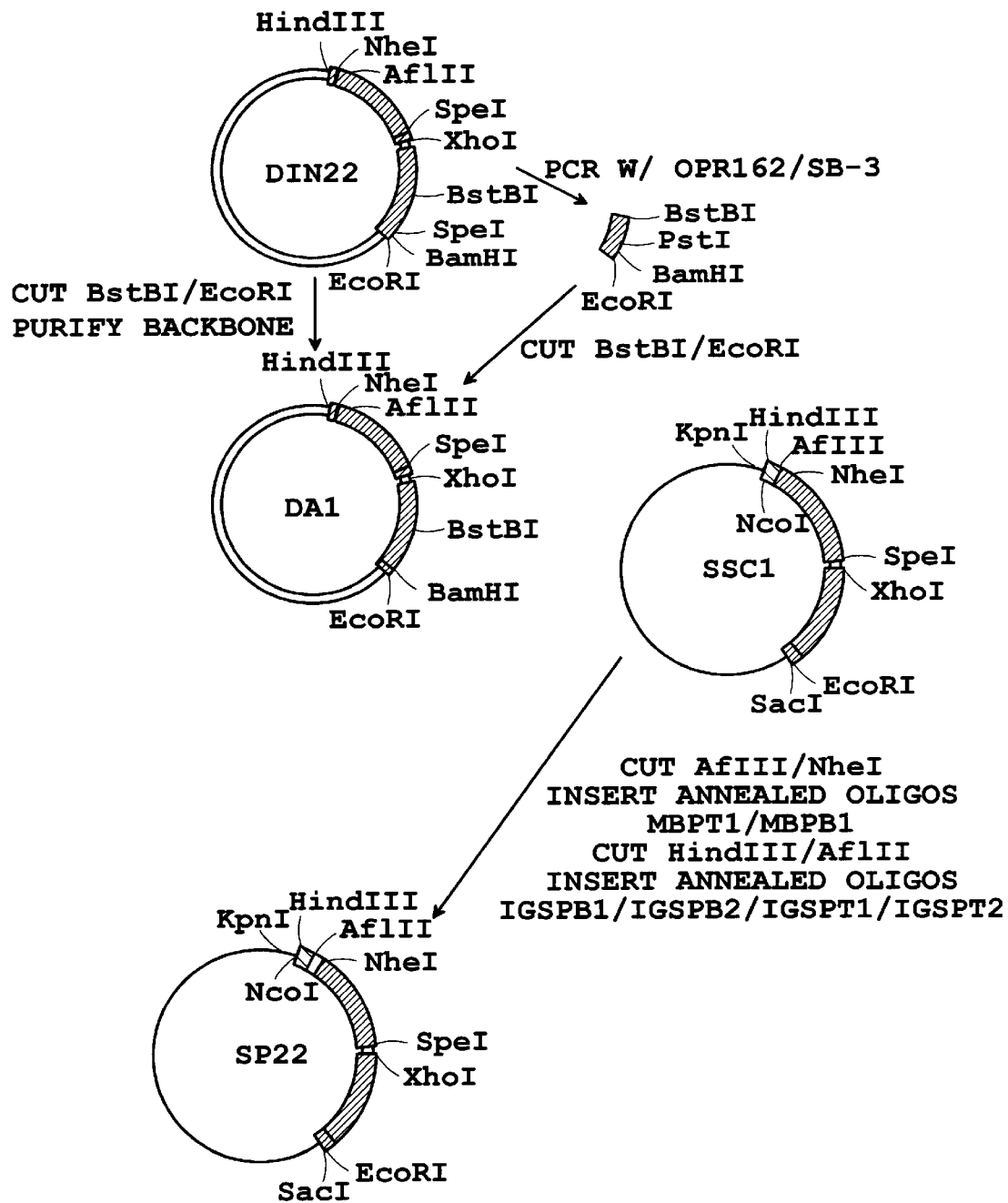
Figure 3D:
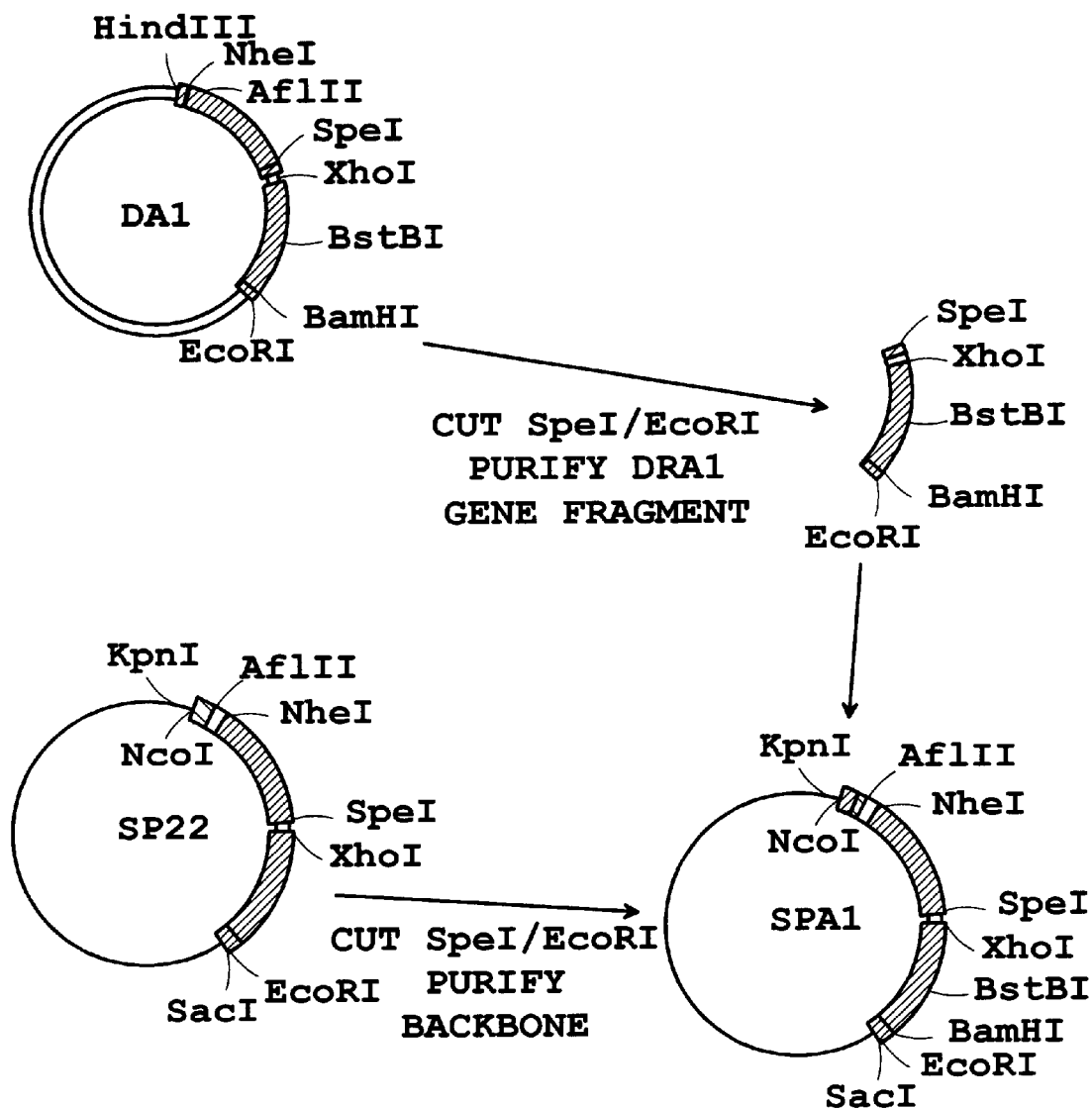
Figure 3E:
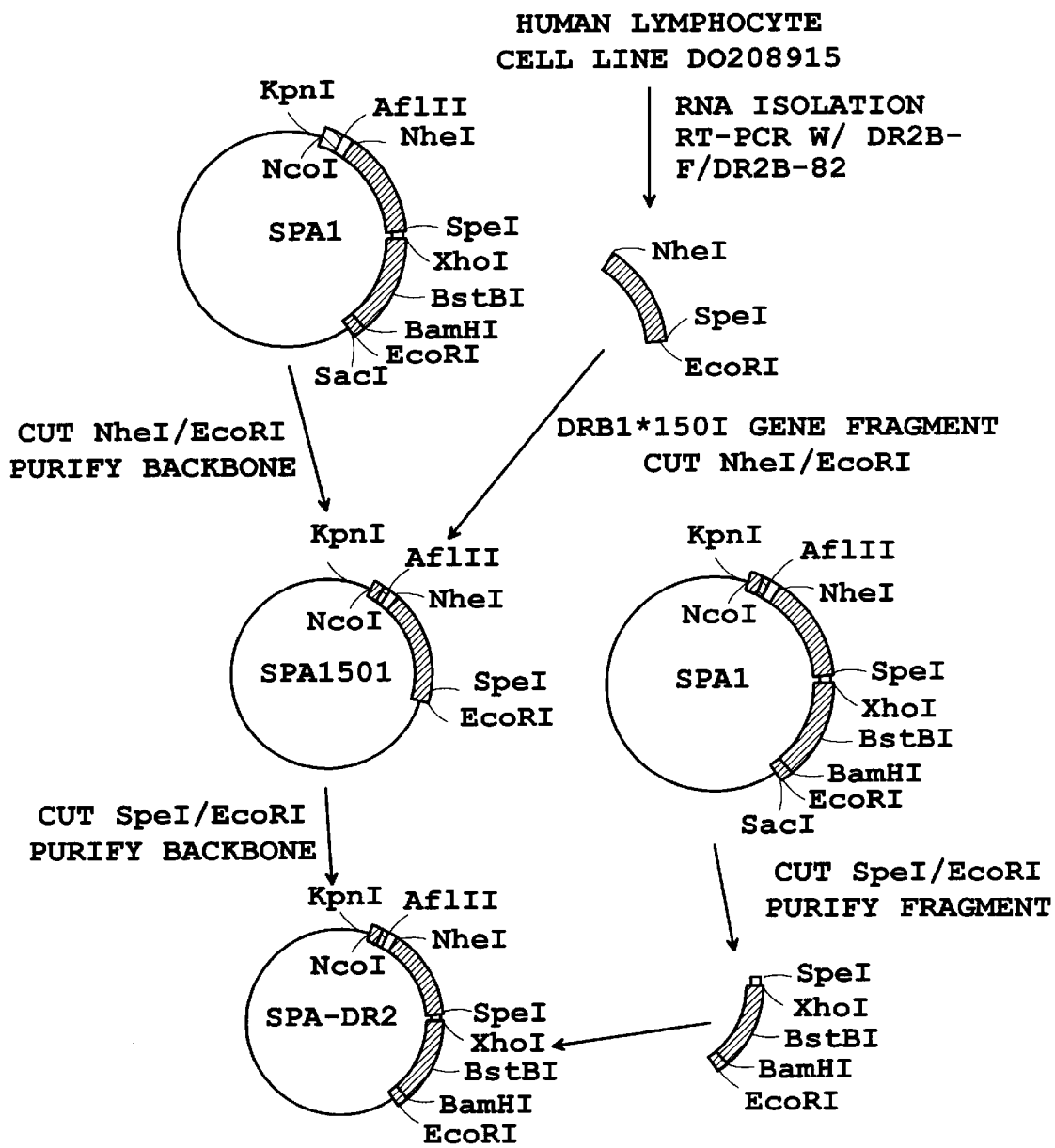
Figure 3F:
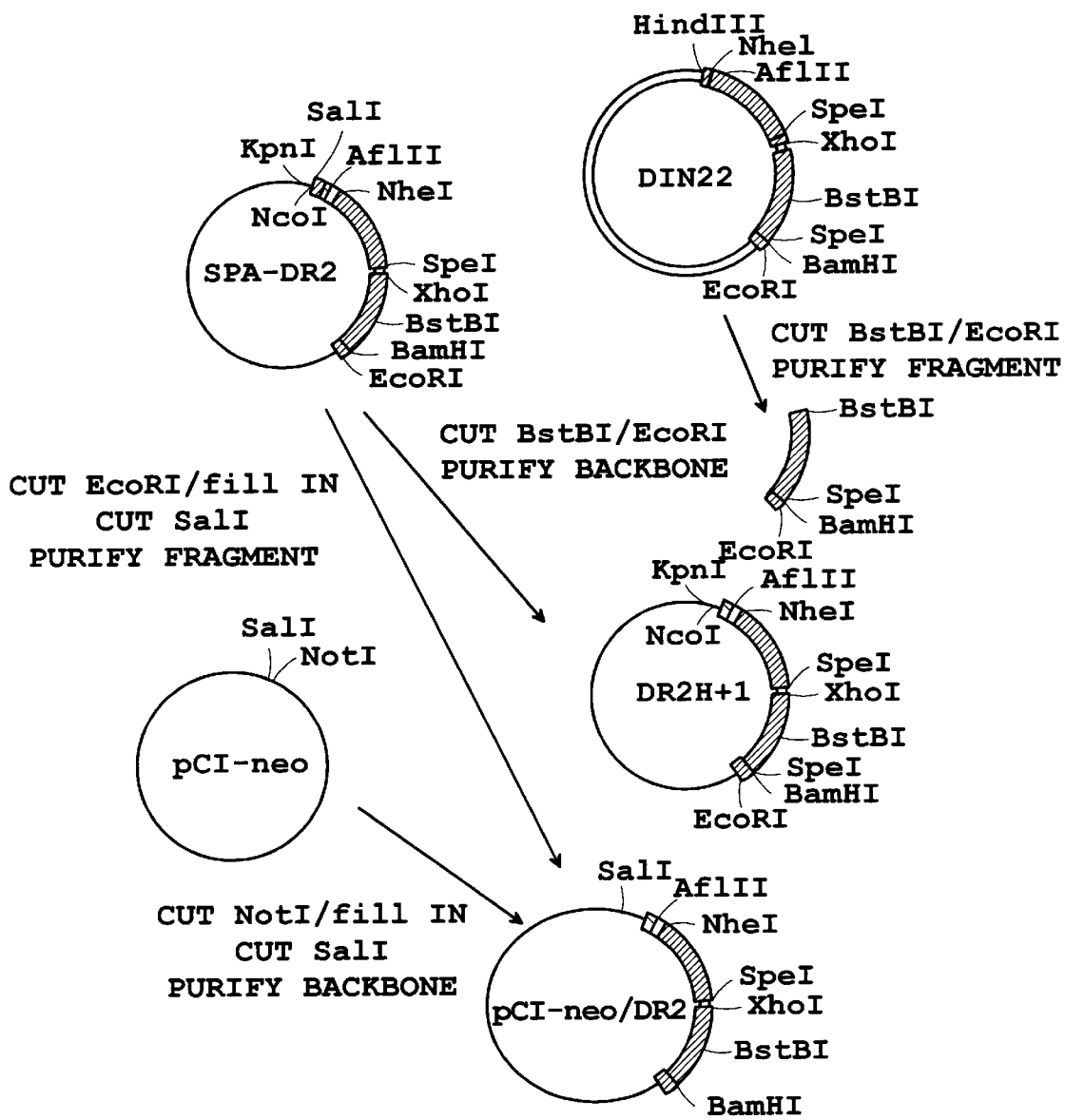
Figure 3G:
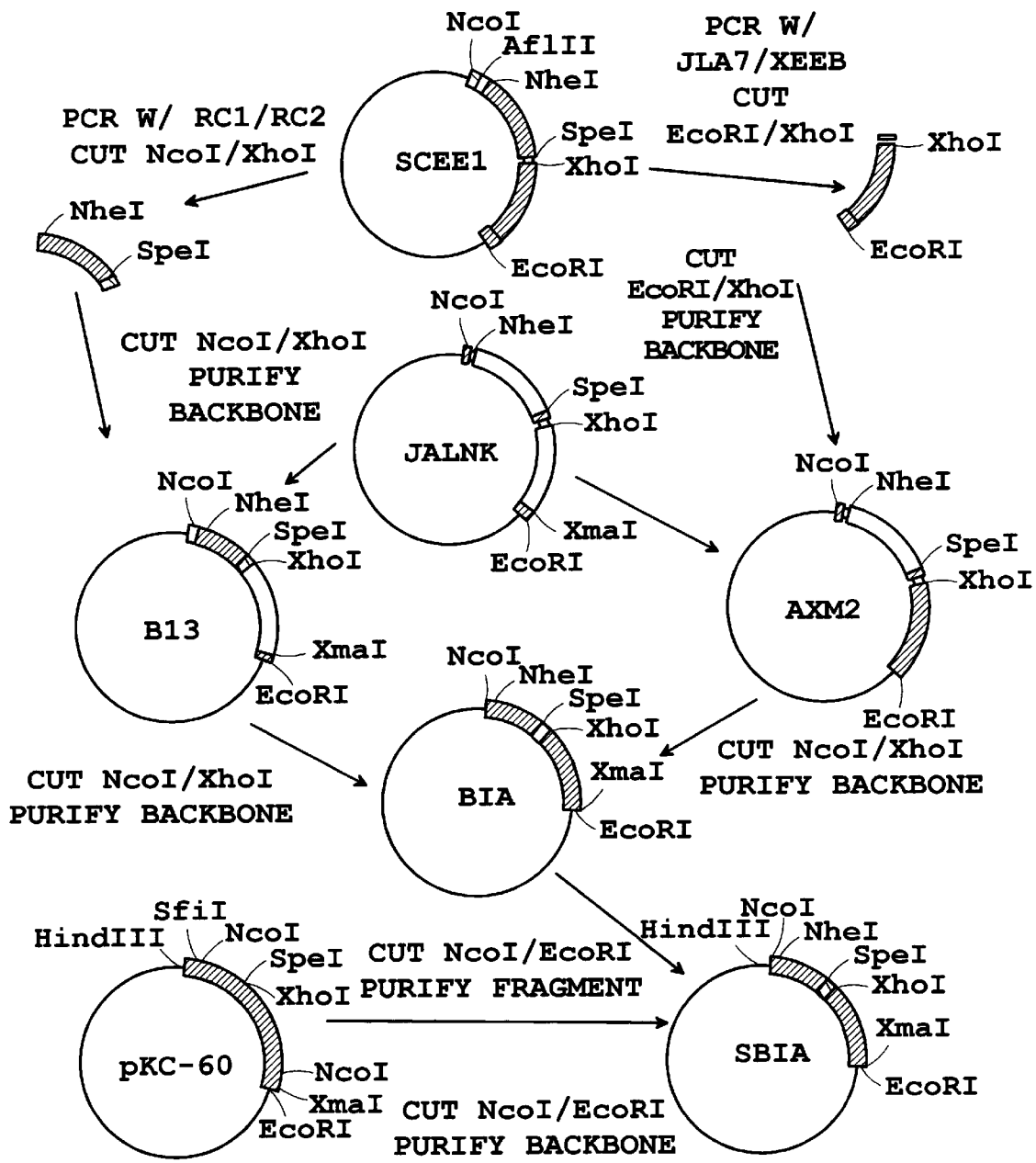
Figure 3H:
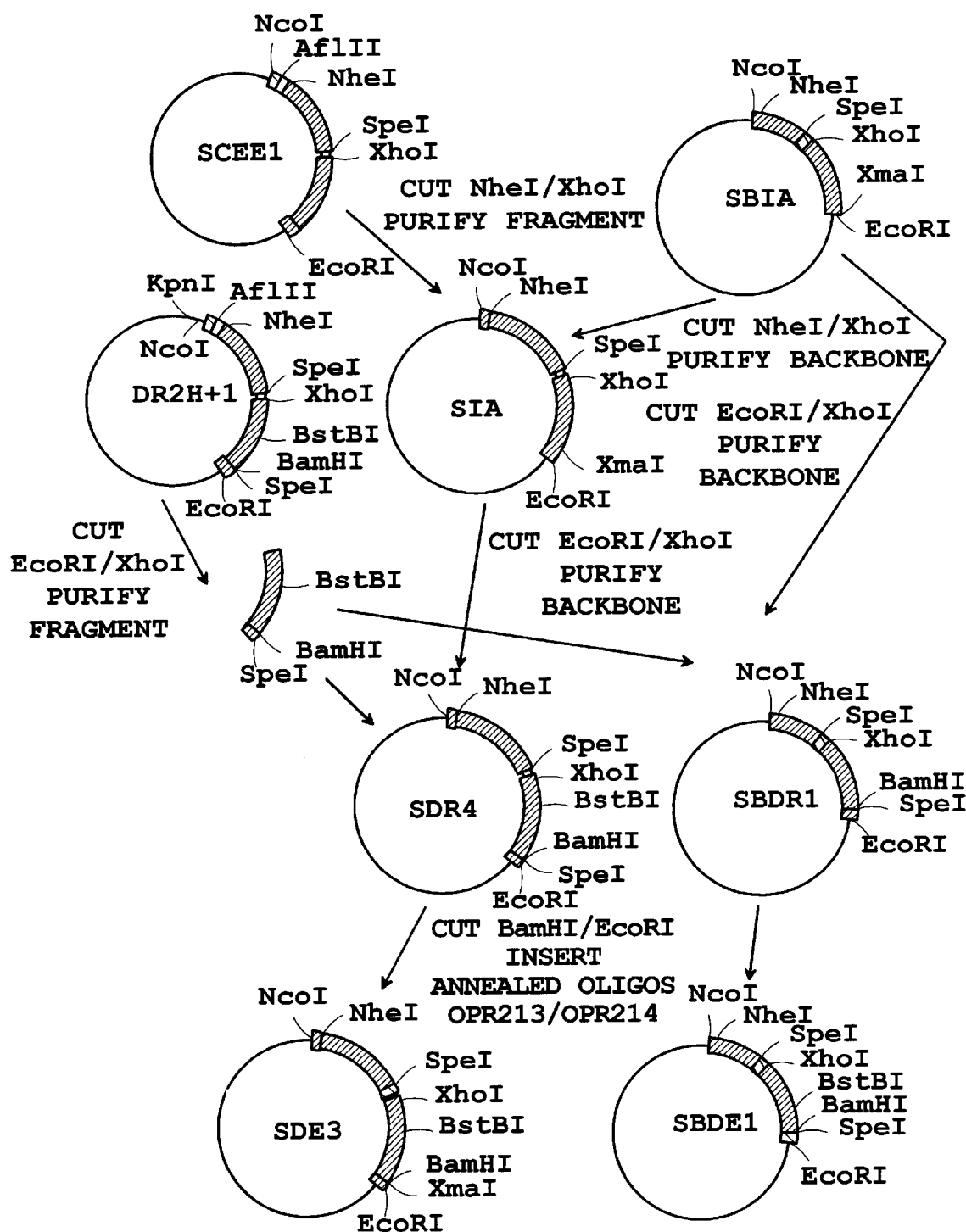
Figure 3I:
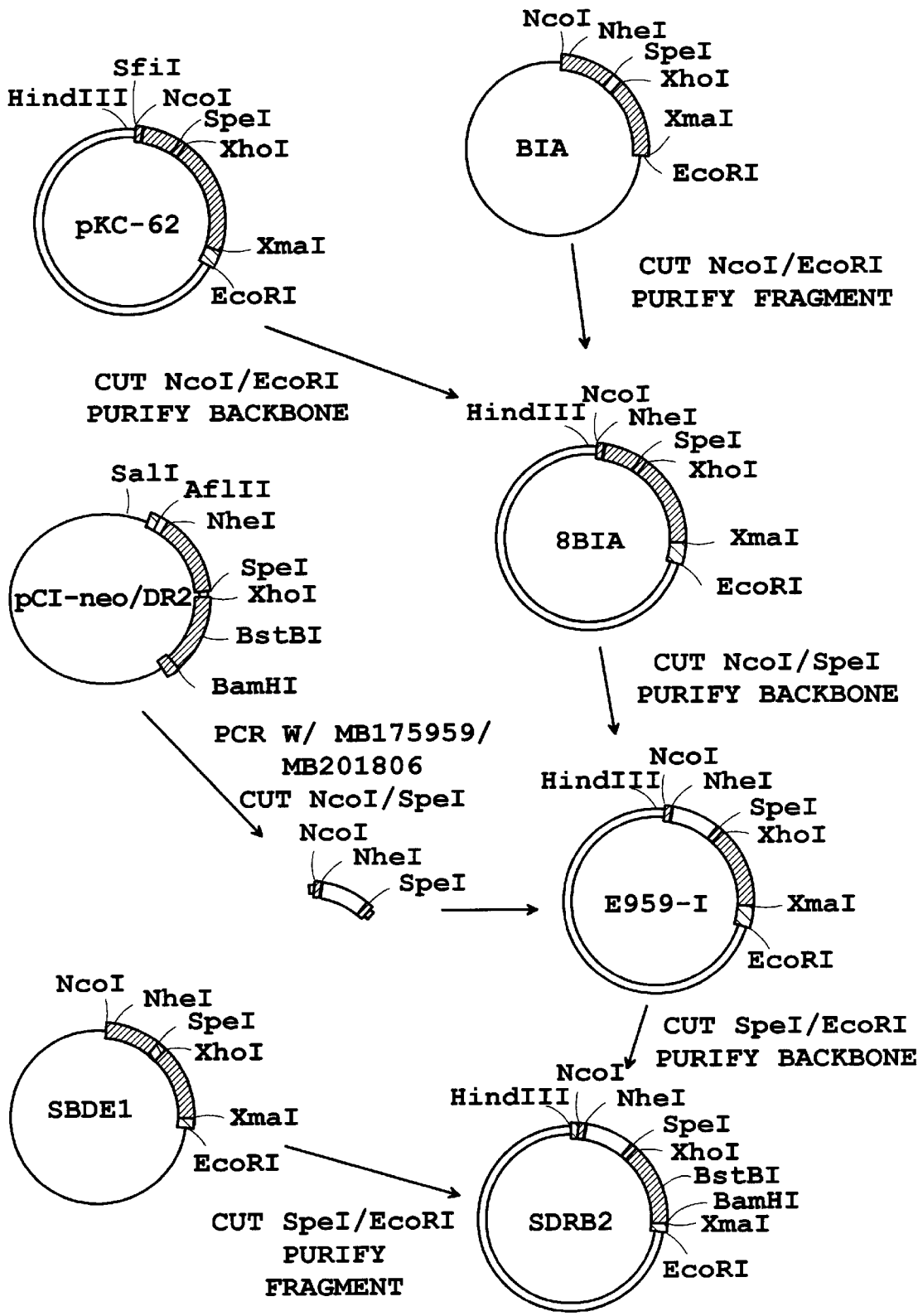
Figure 3J:
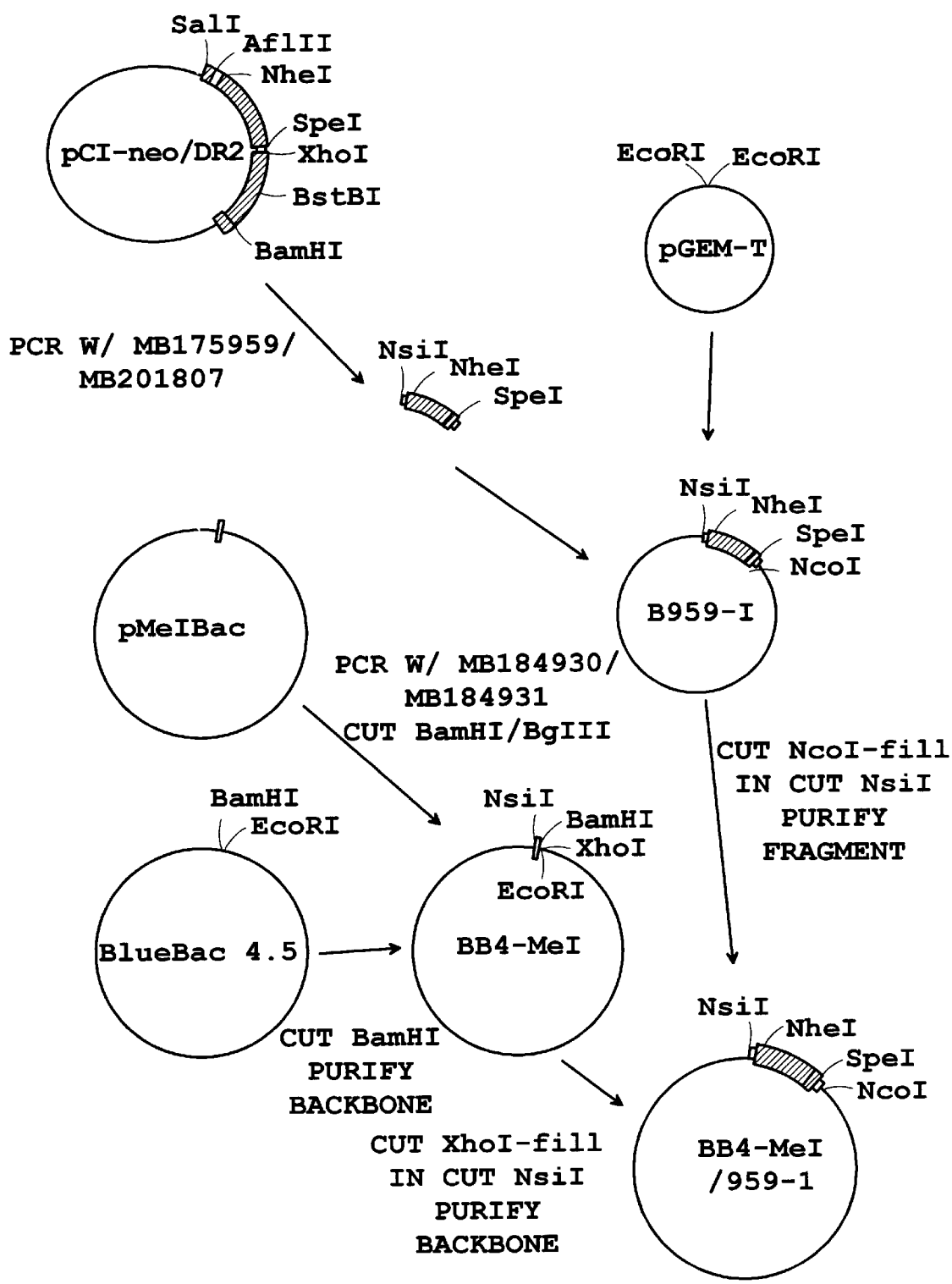
Figure 3K:
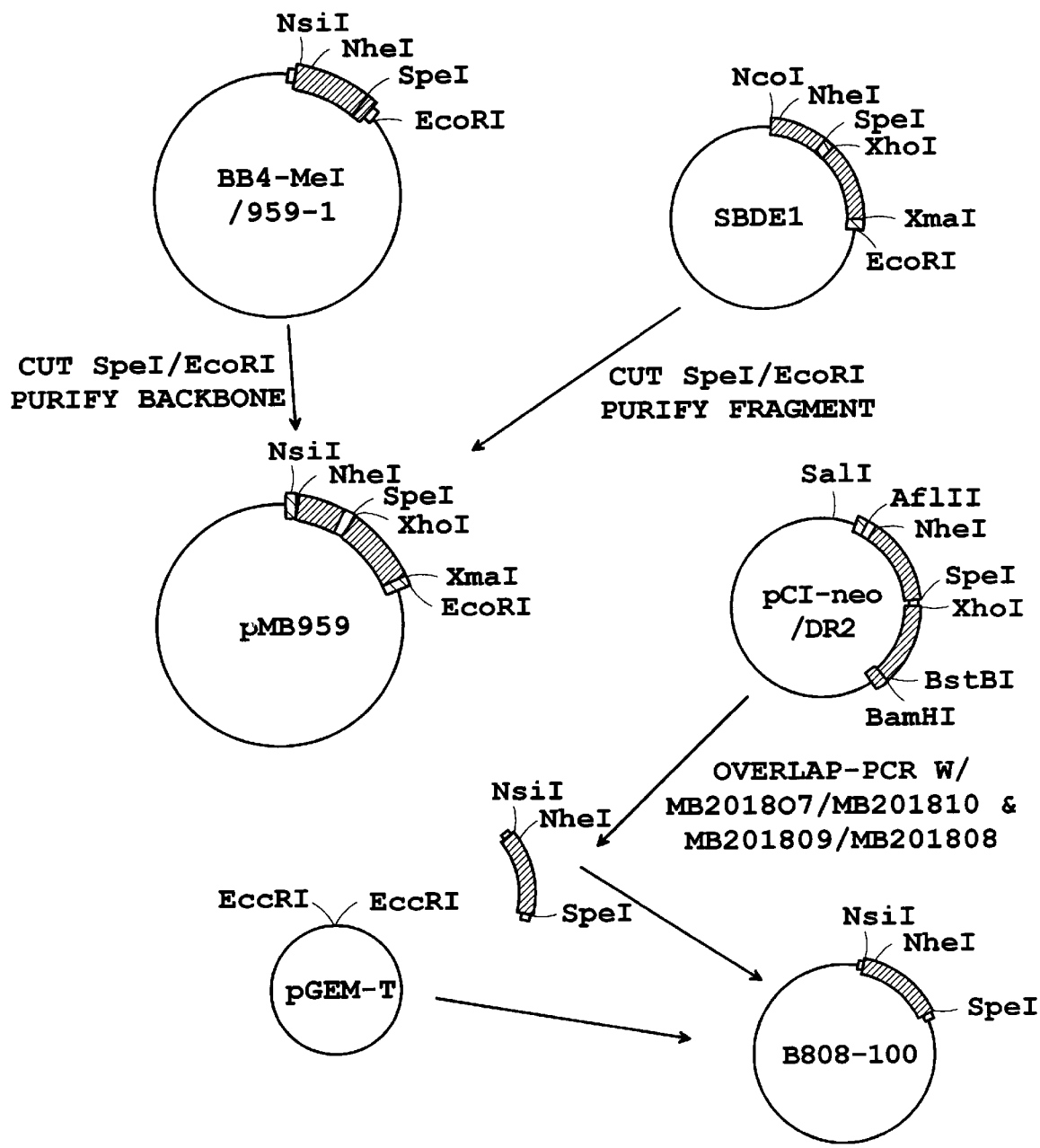
Figure 3L:
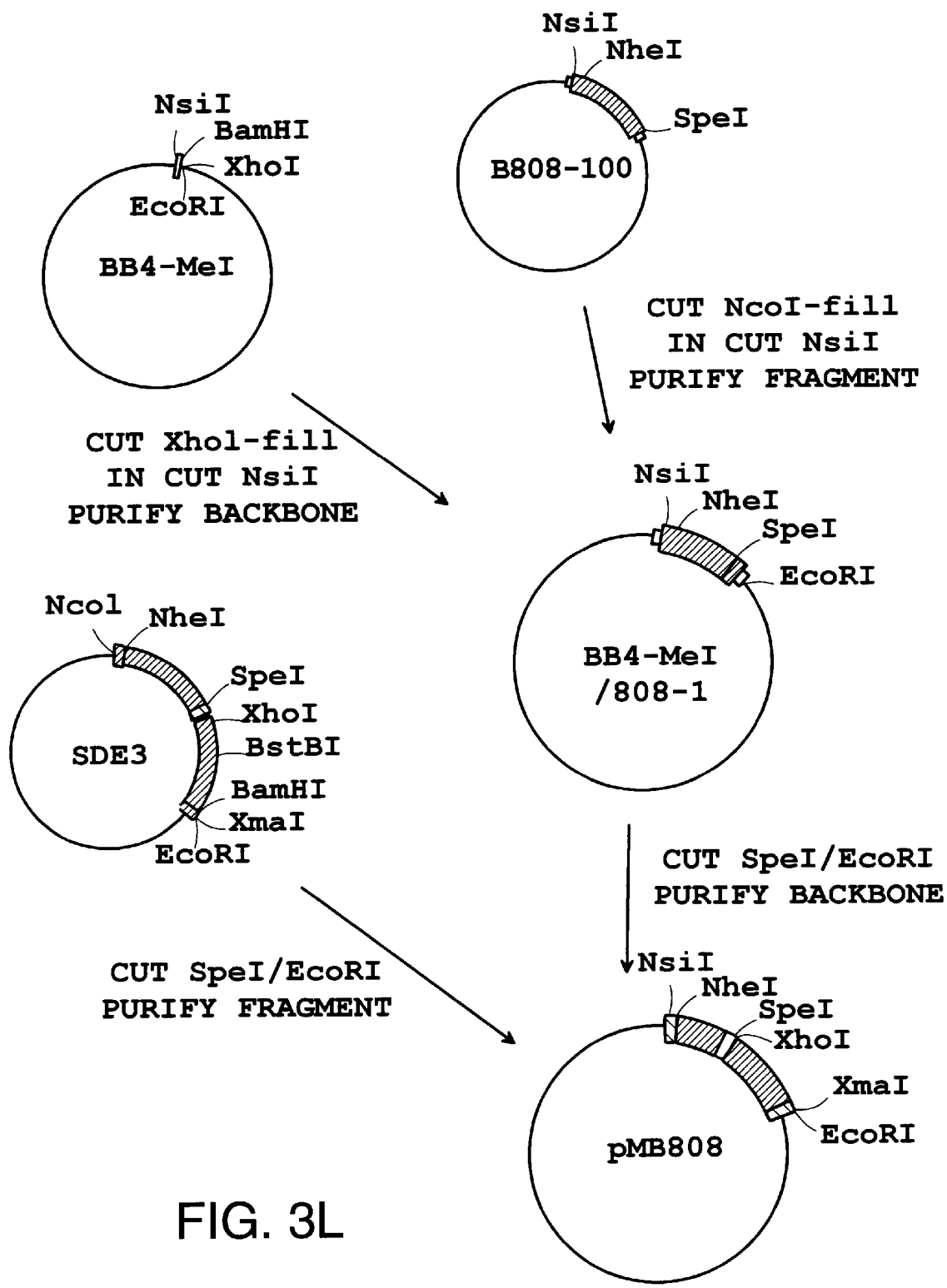
Figure 3M:
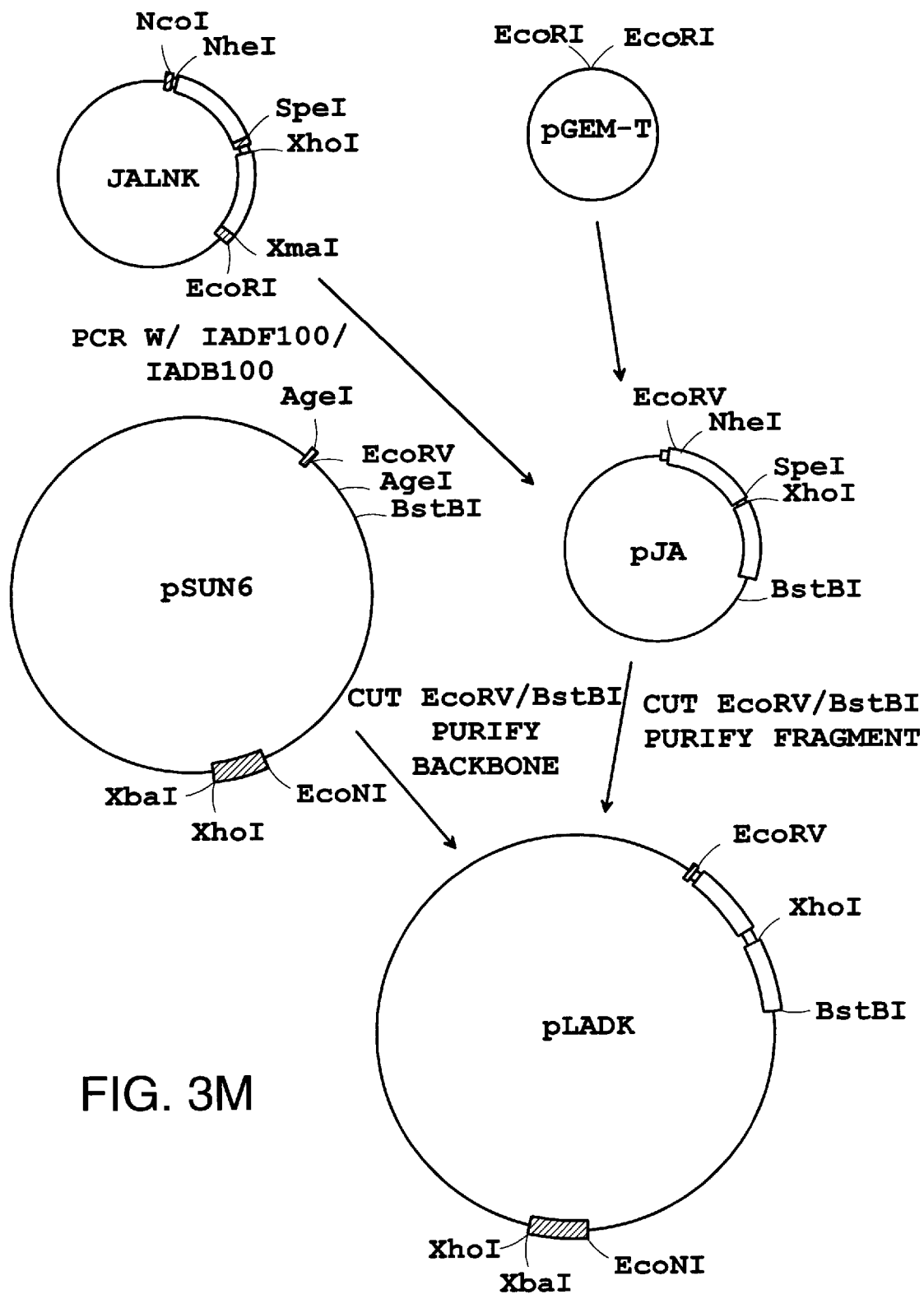
Figure 3N:
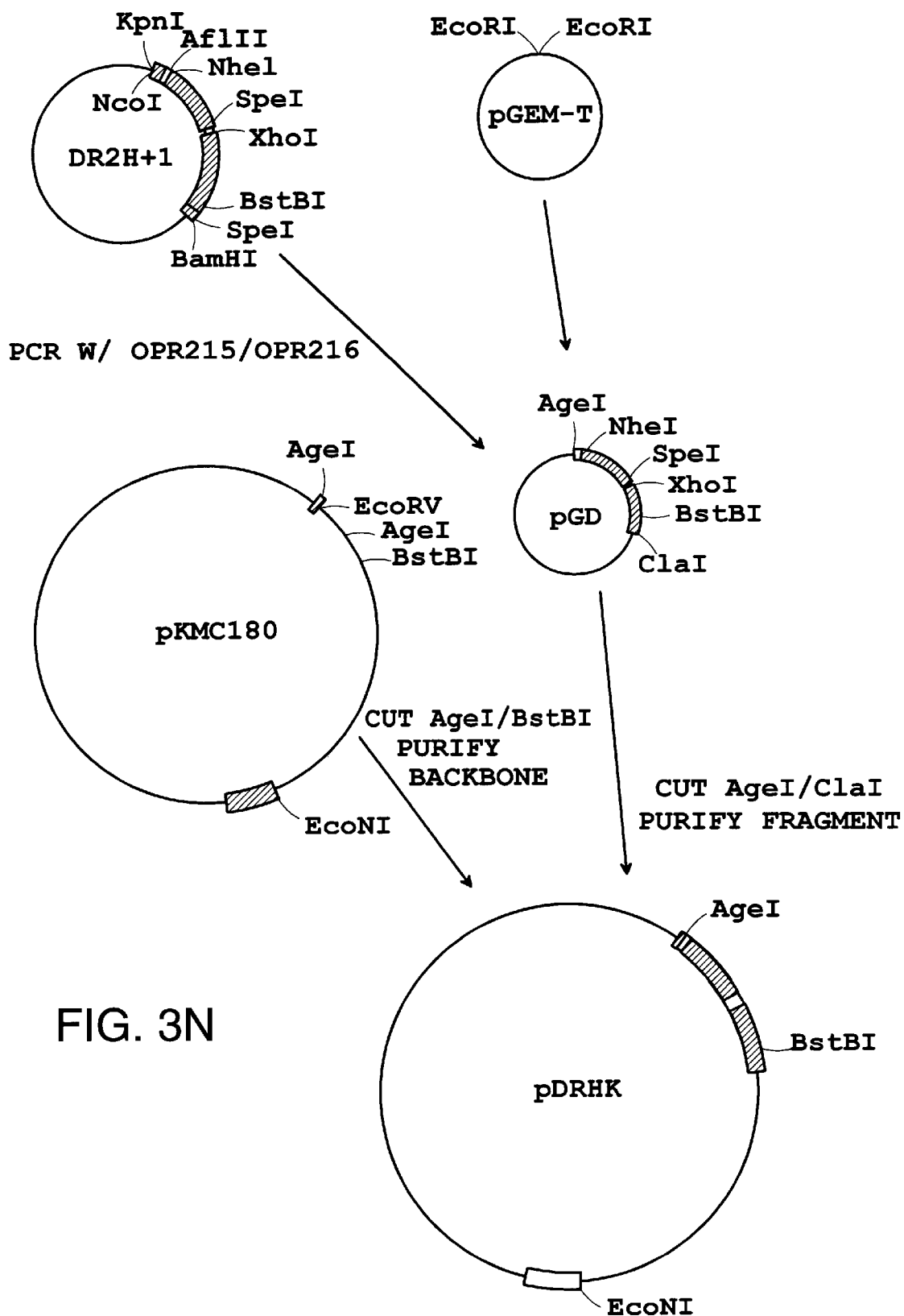

A detailed scheme for the generation of vector described in this example is shown in FIGS. 3A–3N. A list of the primers used in the constructions on the sc-class II gene is shown in Table 1. Reverse transcriptase-polymerase chain reactions (RT-PCRs) were carried out to amplify IA$^d$ α and β chain gene fragments from total RNA isolated from A20-1.11 cells. The following oligonucleotide pairs were used in the initial PCR amplifications: IA$^d$ β leader gene fragment-OPR132, (SEQ ID NO: 2) OPR133 (SEQ ID NO: 3); IA$^d$ β1-β2 gene fragment-OPR102 (SEQ ID NO: 4), OPR104 (SEQ ID NO: 5); and IA$^d$ α1-α2-OPR100 (SEQ ID NO: 6), OPR101 (SEQ ID NO: 7). Restriction sites were introduced at the ends of the gene fragments in subsequent PCR amplifications in order to facilitate fragment cloning. Sequence encoding a 10 amino acid peptide linker was introduced to the 5' end of the β1-β2 gene fragment and the Kozak consensus sequence (SEQ ID NO: 1) was introduced to the 5' end of the β signal sequences by PCR. The regions encoding the 24 amino acid linker and antigenic peptides were generated from annealed oligonucleotides. Assembly of the PCR fragments and double-stranded oligonucleotides in pBlueScript-II generated the sc-IA$^d$ fusion genes represented in FIGS. 3A and 3B.

For soluble expression, the sc-class II fusion gene encodes a signal peptide for proper secretion and processing, a region for insertion of antigenic or auto-reactive peptides, a peptide linker sequence, the class II β1-β2 domains, a single-chain peptide linker sequence and the class II α1-α2 domains. Additional sequences can be inserted after the class II α1-α2 domains in order to facilitate purification and provide the sc-class II molecules the ability to bind joining proteins and/or effector molecules. These sequences include those encoding six histidine residues (6XHis or 6H), an antibody tag sequence (EE tag) or the IgG C$_L$ domains.

For example, the generation of the sc-IA$^d$-IgG Cκ fusion construct was carried out as follows: The OVA-IA$^d$ β1-β2-sc linker-IA$^d$ α1-α2 template (see Example 1) was PCR amplified with oligonucleotide primers, IADF100 (SEQ ID NO: 8), IADB100 (SEQ ID NO: 9). These reactions added an EcoRV site at the 5' end of the OVA sequence and add kappa exon/intron sequences and a BstBI site to the 3' end of the α2 sequence. The sc-IA$^d$/OVA PCR product was cloned into the pGEM-T vector and sequence verified. The fusion gene was then subcloned into a mammalian expression vector pSUN6 (described below) carrying the CMV promoter, mouse IgG kappa leader peptide, the cloning region, mouse kappa intron and mouse kappa constant domain exon sequences. The resulting vector is called pIADK.

1. Insertion of a Multiple Sclerosis-associated Gene into Class II MHC Molecule

The multiple sclerosis-associated HLA-DR2 (1501) genes were linked into a single chain format similar to that of the sc-IA$^d$ gene (see FIGS. 4A and 4B). The sc-DR2 gene product can be complexed (covalently or non-covalently) with multiple sclerosis-associated peptides, e.g. MBP (83–102)Y83:Y-D-E-N-P-V-V-H-F-F-K-N-I-V-T-P-R-T-P-P (SEQ ID NO: 28) (Arimilli, S. et al. (1995), *J. Biol. Chem.* 270:971). The DRA1*0101 α1 α2 gene fragment (encoding aa1 to 192) was initially isolated as described previously (see published PCT Application WO 96/04314). This gene fragment was reamplified by PCR with primers (OPR158, DR1A-B) that added a HindIII and XhoI site to its 5' end and a BamHI site to its 3'end. The HLA-DR2 α1-α2 gene fragment was subcloned (using HindIII and BamHI) into a shuttle vector pJRS161.1 carrying a cloning region (HindIII, BamHI and EcoRI sites) for sequence verification. The HLA-DR2 α1-α2 gene fragment was subcloned (using XhoI and EcoRI) into bacterial shuttle vector, SBIA, carrying a cloning region (NcoI, NheI and SpeI sites), a 14 amino acid linker sequence (T-S-G-G-G-G-S-G-G-G-G-S-S-S SEQ ID NO: 29) and a second cloning region (XhoI, BamHI and EcoRI sites). Annealed oligonucleotides (OPR203000 (SEQ ID NO: 12), OPR203001 (SEQ ID NO: 13)) encoding the EE antigen tag (E-E-E-E-Y-M-P-M-E-P-G-Stop (SEQ ID NO: 30) were subcloned between the BamHI and EcoRI sites of the second cloning region. The resulting vector is referred to as SBDE1. The HLA-DR2 α1-α2 gene fragment was also subcloned (using XhoI and EcoRI) into a bacterial shuttle vector, SIA carrying a cloning region (NcoI, NheI and SpeI sites), 24 amino acid single-chain linker sequence (T-S-G-G-G-G-S-G-G-G-G-S-G-G-G-G-S-G-G-G-G-S-S-S (SEQ ID NO: 31)) and a second cloning region (XhoI, BamHI and EcoRI sites). Annealed oligonucleotides (OPR 203000, OPR 203001) encoding the EE antigen tag were subcloned between the BamHI and EcoRI sites of the second cloning region. The resulting vector is referred to as SDE3. See, Kabat, E. A., supra for disclosure relating to the HLA-DR2 (1501) gene sequence.

For the HLA-DRB1*1501 gene, total RNA was isolated from the human lymphocyte cell line, DO208915 (ASHI Repository Accession No. 9008). Generation of cDNA and PCR amplification of the DRB1*1501 β1-β2 gene fragment (aa1-188) was carried out using oligonucleotide primers (DR2B-F (SEQ ID NO: 14), DR2B-B2 (SEQ ID NO: 15)). These primers allow for the addition of an NheI site and an 8 amino acid linker sequence to the 5' end of the β1 sequence and SpeI and EcoRI sites to the 3' end of the β2 sequence. This DRB1*1501 PCR product was cloned (NheI/EcoRI) into a vector carrying AflII, NheI and EcoRI restriction sites. Annealed oligonucleotides (MBPF, MBPR) encoding MBP (84–102) (D-E-N-P-V-V-H-F-F-K-N-I-V-T-P-R-T-P-P (SEQ ID NO: 32)) were subcloned between the AflII and NheI sites of the DRB1*1501 vector. A DNA fragment encoding a 24 amino acid single-chain linker sequence (T-S-G-G-G-G-S-G-G-G-G-S-G-G-G-G-S-G-G-G-G-S-S-S SEQ ID NO: 31) was inserted between the SpeI and EcoRI sites of the DRB1*1501 vector. Finally, the DRA1*0101 α1 α2 gene fragment (encoding aa1 to 192) described above was inserted after the sc-linker sequence. The completed vector carries the MBP-DRB1*1501 β1-β2-sc linker-DRA1*0101 α1 α2 gene fragment and served as the template for further manipulations.

1. Deletions in the MHC Class II β2 Domain Increase Soluble Expression

To test for increased soluble expression, single-chain DR2 constructs were generated that carrying deletions in the β2 domain (See FIG. 4B). In one example, the entire β2 domain was deleted by PCR amplifying the MBP-DRB1*1501 β1-β2 template with the appropriate oligonucleotide primers (for bacterial expression—MB201806 (SEQ ID NO: 16) and MB175959 (SEQ ID NO: 17), for baculoviral expression—MB201807 (SEQ ID NO: 18) and MB175959 (SEQ ID NO: 17)). These reactions changed the MBP sequence to the following: Y-D-E-N-P-V-V-H-F-F-K-N-I-V-T-P-R-T-P-P (SEQ ID NO: 28). The PCR bacterial expression was cloned into a bacterial expression vector, 8BIA, derived from pKC62 described in co-pending U.S. application Ser. No. 08/813,781, filed on Mar. 7, 1997, the disclosure of which is incorporated by reference. This vector carries the phoA promoter and pelB leader sequence for inducible soluble expression of cloned gene fragments. The PCR products were cloned into pGEM-T vector and sequence verified. For bacterial expression, the MBP-DRB1*1501 β1 fragment (NcoI-SpeI) was subcloned into the SBDE1 vector resulting the SDRB2 expression vector. For baculoviral expression, the MBP-DRB1*1501 β1 fragment in pGEM-T was cloned (NsiI-NcoI) into a version of pBlueBac4.5 (Invitrogen) modified to encode the mellitin signal peptide under the control of the polyhedrin promoter. The 14 aa linker-DR2 α1-α2-EE tag fusion gene fragment (SpeI-EcoRI) of SBDE1 was subcloned into the pGEM-T vector carrying the MBP-DRB1*1501 α1 fragment. The single-chain DR2Δβ2/MBP fragment was cloned (NsiI/EcoRI) into a version of pBlueBac4.5 (Invitrogen) modified to encode the mellitin signal peptide under the control of the polyhedrin promoter. The resulting vector is referred to as pMB959.

The pKC62 vector (pSUN19) described above has been deposited pursuant to the Budapest Treaty with the American type Culture Collection (ATCC) at 12301 Parkman Drive, Rockville, Md. The DNA vector was deposited on Feb. 26, 1997, and was assigned Accession NO. 97896. The pKC62 vector includes a pho A promoter, modified pelB sequence, gene 10 ribosome binding site and a bacteriophage gene VIII promoter. The DNA vector can be readily propagated in E. coli or other suitable host cells in accordance with standard methods.

To further modify the β2 domain, the pCI-neo/DR2 template was PCR amplifying with the appropriate oligonucleotide primers (MB201807 (SEQ ID NO: 18 and MB201810 (SEQ ID NO: 21) and MB201809 (SEQ ID NO: 20) and MB201808 (SEQ ID NO: 19) to mutate the Cys codon at amino acid 117 to a Ser codon, followed by overlap PCR using MB201807 (SEQ ID NO: 18 and MB201808 (SEQ ID NO: 19). These reactions changed the MBP sequence to the following: Y-D-E-N-P-V-V-H-F-F-K-N-I-V-T-P-R-T-P-P (SEQ ID NO: 28). The PCR products were cloned into pGEM-T vector and sequence verified. For baculoviral expression, MBP-DRB1*1501 β1-modβ2 fragment in pGEM-T was cloned (NsiI-NcoI) into a version of pBlueBac 4.5 (Invitrogen) modified to encode the mellitin signal peptide under control of the polyhedrin promoter. The 24 aa linker-DR2 α1-α2-EE tag fusion gene fragment (SpeI-EcoRI) of SDE3 was subcloned into the pGEM-T vector carrying the MBP-DRB1*1501 β1-mod β2 fragment. The single-chain DR2Δβ2/MBP fragment was cloned (NsiI/EcoRI) into a version of pBlueBac4.5 (Invitrogen) modified to encode the mellitin signal peptide under the control of the polyhedrin promoter. The resulting vector is referred tp as pMB808.

For generation of the sc-DR2-IgG Cκ fusion construct, the MBP-DRB1*1501 β1-β2-sc linker-DRA1*0101 α1 α2 template was PCR amplified with oligonucleotide primers, OPR215 (SEQ ID NO: 22), OPR216 (SEQ ID NO: 23). These reactions added an AgeI site at the 5' end of the MBP sequence, changed the MBP sequence to Y-D-E-N-P-V-V-H-F-F-K-N-I-V-T-P-R-T-P-P (SEQ ID NO: 28) and add kappa exon/intron sequences and a ClaI site to the 3' end of the α2 sequence. The sc-DR2/MPB PCR product was cloned into the pGEM-T vector and sequence verified. The fusion gene was then subcloned into a mammalian expression vector pKCM 180 (described below) carrying the CMV promoter, mouse IgG kappa leader peptide, the cloning region, mouse kappa intron and human kappa constant domain exon sequences. The resulting vector is called pDRHK.

The mammalian Ig-Cκ expression vectors, pSUN6 and pKCM180, were generated as follows: The backbone of the vector was the plasmid pCDNA3 (Invitrogen) which carries the CMV promoter to drive expression of cloned genes. This plasmid was cut HindIII/XhoI and a "light chain polylinker" DNA fragment was inserted to create the starting pCDNA:L-CPL vector. This linker contained the restriction sites HindIII, KpnI, ClaI, PmlI, EcoRV, AgeI, XmaI, BamHI and XhoI to facilitate subsequent cloning steps. A SmaI/BclI DNA fragment containing a light chain leader, anti-CKMB kappa light chain genomic fragment, and 3'UTR was cloned into the EcoRV/BamHI sites of pCDNA/LCPL. The mouse intron, exon and the 3'UTR in this fragment was derived from pneo/20-10VL described by Near, et al., (1990) *Mol. Immunol.* 27:901. Subsequent mutagenesis was then performed to eliminate and introduce appropriate restriction enzyme sites creating the pSUN6 vector. This vector carries the CMV promoter followed by light chain leader sequence and the anti-CKMMB kappa light chain genomic sequence of which the variable domain gene is present as an EcoRV/BstBI fragment and the mouse kappa constant domain gene sequence as an EcoNI/XhoI fragment.

To create the human Cκ expression vector, the mouse kappa constant domain sequence (EcoNI/XhoI) of pSUN6 was substituted with the appropriate PCR amplified fragment carrying the human kappa constant domain. The resulting vector, pKCM180, carries the CMV promoter followed by light chain leader sequence, the anti-CKMB kappa light variable domain exon, mouse intron, and human kappa light chain exon sequences.

The pDRHK and pIAdk vectors described above have been deposited with the ATCC at the address listed above pursuant to the Budapest Treaty. The DNA vectors were deposited on Sep. 17, 1997 and have been assigned Accession Nos. 209274 (pDRHK) and 209275 (pIAdk). The DNA vectors can be readily propagated in a variety of suitable mammalian host cells in accordance with standard methods.

EXAMPLE 4
Expression of Soluble sc-MHC Class II Molecules in Bacterial Cells

The MM294 *E. coli* strain (Sambrook et al, supra) was transformed with the SDE3 plasmid (e.g. soluble sc-DR2Δβ2/MBP, see Example 3) by standard molecular cloning methodologies. This vector carries a gene conferring resistance to ampicillin. Transformed MM294 cells were grown overnight at 30° C. in high phosphate medium (10 mM $KH_2PO_4$ in defined medium—50 µg/ml ampicillin, 0.4% glucose, 0.15% casamino acids, 0.0002% thiamine, 4 mM tricine, 10 mM $FeSO_4$, 9.7 mM $NH_4Cl$, 0.29 mM $K_2SO_4$, 0.07 mM $CaCl_2$, 0.53 mM $MgCl_2$, 50 mM NaCl, 40 mM MOPS, pH 7.4). To induce the expression of the sc-DR2 gene product, the cells were transferred to low phosphate media (0.1 mM KH2PO4 in defined medium) for 8 hours at 30° C. The cells were harvested and resuspended in PBS+ 1% Trition-X100. The cell wall was broken by sonication and soluble material collect following centrifugation. Expressed sc-DR2 molecules were detected by a conformation-specific DR-specific sandwich ELISA using MAS-96p (Harlan Sera-lab) as the capture mAb (0.1 µg/well) and HRP-conjugated L243 (0.1 µl/ml) (ATCC HB-55) as the probe mAb. Antibody binding was detected by incubating with avidin peroxidase (0.25 µg/well) followed by ABTS substrate (Kirkegaard and Perry). Purified native DR2 served as a positive standard. The results of such an assay are shown in Table 2.

TABLE 2

| Production of sc-DR2 from Bacterial Cells | |
| --- | --- |
| Construct | DR2 Detected |
| SDE3 (sc-DR2-Δβ2/MBP) | 1 µg/g cell pellet |

These results indicate that the sc-DR2 molecules lacking the β2 domain are expressed in a form that is recognized by antibodies that are specific to the proper folding of the native HLA-DR conformation. This was an unexpected result since the β2 domain of class II molecules know to interact with the α2 domain and is thought to play an important role in the proper folding of the complex (see Brown, J. H. et al. 1993. *Nature* 364: 33). Furthermore, removal of domain appears to improve the soluble expression of the sc-class II molecules in bacteria cells. This was not expected since sc-DR2 constructs carrying the full β2 domain are expressed in an insoluble form in *E. coli*.

1. Large Scale Production Of MHC Complex in Bacterial Cells

Large scale production of soluble sc-class II molecules can be achieved using bacterial expression systems. For example, fermentors containing 80 L of defined growth media can be each inoculated with transformed MM294 carrying the sc-DR2 fusion gene. The cells can be maintained in accordance with standard bacterial fermentation technique. Once the phosphate in the growth medium is depleted, expression of the sc-DR2 gene product will be induced. The cells can be collected at the suitable time by continuous flow centrifugation or by filtration using a Millipore Pellicon tangential flow microporous filtration unit. The cells can be broken using a Gaulin press and soluble material carrying the sc-MHC class II molecules can be obtained following centrifugation. It is expected that each fermentation will yield about 0.01–0.1 gram amounts of soluble MHC class II molecule.

EXAMPLE 5
Expression of Soluble sc-MHC Class II Molecules in Insect Cells

Soluble sc-IA$^d$ and sc-DR2 molecules were obtained from SF9 insect cells by using a baculovirus expression system (InVitrogen). Soluble sc-IA$^d$ constructs with no peptide (sc-IA$^d$/blank), the OVA 323–339 peptide (sc-IA$^d$/OVA), or the gD 246–261 peptide (sc-IA$^d$/gD) were individually subcloned downstream of the baculovirus polyhedrin promoter of pBluebac III in accordance with the manufacturer's instructions (Invitrogen). The sc-DR2 constructs, pMB959 and pMB808, were prepared as described above. The fusion genes were then individually recombined into baculovirus following liposome-mediated cotransfection of SF9 insect cells with linearized wt AcMN-PV (wild-type). After cloning by limiting dilution, purified recombinant virus stocks were prepared.

More specifically, production of the soluble sc-IA$^d$ fusion gene products was accomplished by infecting SF9 cells ($1\times10^6$ cells/ml) in Hink's TMN-FH insect media supplemented with 10% fetal bovine serum. The multiplicity of infection (MOI) was about 10. After 5 days, the culture supernatant was collected, and then adjusted to pH 8.0 with 1 M Tris prior to affinity purification. Expressed sc-IA$^d$ molecules were detected by a sensitive IA$^d$-specific sandwich ELISA using M5/114 (Bhattacharya, A., M. E. Dorf, T. A. Springer. 1981. *J. Immunol.* 127:2488) as the capture mAb (0.1 µg/well) and biotin-conjugated AMS-32.1 (Wall, K. A., M. I. Lorbver, M. R. Loken, S. McClatchey, and F. W. Fitch. (1983) *J. Immunol.* 131:1056) (0.1 µg/ml) (PharMingen) as the probe mAb. Antibody binding was detected by incubating with avidin peroxidase (0.25 µg/well) followed by ABTS substrate (Kirkegaard and Perry).

In another example, production of the soluble sc-DR fusion gene products carrying modifications in the β2 domain was tested. Infection of SF9 cells was accomplished as described above. Expressed sc-DR2 molecules were detected by a conformation-specific DR-specific sandwich ELISA using MAS-96p (Harlan Sera-lab) as the capture mAb (0.1 µg/well) and HRP-conjugated L243 (0.1 µl/ml) (ATCC HB-55) as the probe mAb. Antibody binding was detected by incubating with avidin peroxidase (0.25 µg/well) followed by ABTS substrate (Kirkegaard and Perry). Purified native DR2 served as a positive standard. The results of such an assay are shown in Table 3.

TABLE 3

Production of sc-DR2 from insect cells

| Construct | Detected |
|---|---|
| pMB959 (sc-DR2-Δβ2/MBP) | 1.0 µg/ml |
| PMB808 (sc-DR2-mod β2/MBP) | 0.1 µg/ml |

As discussed previously, these results are unexpected since the β2 domain of class II molecules is thought to play an important role in the folding of the complex (see Brown, J. H. et al. 1993. *Nature* 364: 33). The sc-DR2 molecules either lacking this domain or with modification in this domain are recognized by antibodies that are specific to the proper folding of the native HLA-DR conformation. Furthermore, removal or modification of this domain appears to improve the soluble expression of the sc-class II molecules in insect cells. This was not expected since sc-DR2 constructs carrying the full β2 domain are poorly expressed in this system.

1. Large-scale Production of MHC Complexes in Insect Cells

Large scale production of soluble sc-class II molecules can be achieved. For example, three spinner flask containing 20L of growth media can be each inoculated with about $2 \times 10^{10}$ of SF9 insect cells. The cells could be maintained and continuously sparged with 50% oxygen:50% nitrogen in accordance with standard cell culture technique. Each of the spinner flasks could then be inoculated with one of the recombinant baculovirus stocks and the SF9 culture media is collected at the suitable time by filtration using a Millipore Pellicon tangential flow microporous filtration unit.

EXAMPLE 6
Expression of Soluble sc-IA$^d$ Molecules in Mammalian Cells

Transfection and selection of mammalian cell lines was carried out as follows: $1 \times 10^7$ NSO cells were washed twice in ice cold PBS, resuspended in 760 µl of cold PBS, and mixed with 40 µg (1 µg/µl) of SalI linearized plasmid SCE1 DNA (i.e. for the soluble form of the sc-IA$^d$/OVA molecules). After 5 min incubation on ice, the cells were electroporated using a Gene Pulser (Biorad) to deliver one pulse of 250 volts, 960 µFd. The pulsed cells were placed on ice for 2–5 min and added to 30 ml of non-selective medium (IMDM, 10% FBS, 2 mM glutamine, 5000 units/ml penicillin, 5000 µg/ml streptomycin). Cells were plated in 96-well flat bottom tissue culture plates and 24 h later, 150 µl of selective medium (IMDM, 10% dialyzed FBS, 5000 units/ml penicillin, 5000 µg/ml streptomycin, 1×nucleosides, 1×glutamate+asparagine) was added to each well. The plates were fed with selective medium on a weekly basis by removing 100 µl/well used medium and adding 100 µl/well of fresh selective medium, allowing the cells to gradually deplete the medium of all residual glutamine. The glutamine synthetase gene carried on the SCE1 plasmids allows selective growth of the transfected cells in glutamine-free media. Colonies of the cells transfected with the plasmid became evident after 14–21 days.

The transfectants carrying the SCE1 vector (i.e. soluble form of the sc-IA$^d$/OVA molecules) were expanded and screened for expression and secretion of the MHC molecules by the IA$^d$ specific ELISA assays described above. Construction of the SCEI vector has been described in the published PCT application WO96/04314. The results of such an assay of the culture supernatant from two SCE1 transfected cell lines are shown in Table 4. These results indicate that the transfected cells produce and secrete the sc-IA$^d$/OVA molecule.

TABLE 4

IA$^d$ ELISA assay on SCE1 transfectant cell culture supernatants

| Culture Supernatant (undiluted) | Absorbance |
|---|---|
| NSO (parental cell line) | 0.444 |
| E10 (SCE1 transfectant) | 0.781 |
| E11 (SCE1 transfectant) | 0.960 |
| sc-IA$^d$/OVA from insect cell culture (positive control) | 2.44 |

1. Fusion of an IgG Cκ Fragment Facilitates Soluble Expression

To test whether the level of expression of the sc-class II molecule could be improved, a gene fusion between the sc-IA$^d$/OVA molecule and the IgG Cκ fragment was made (see Example 3). This construct was transfected into mammalian cell lines as follows: $1 \times 10^7$ NSO cells were washed twice in ice cold PBS, resuspended in 790 µl of cold PBS, and mixed with 10 µg (µ1 µg/µl) PvuI linearized plasmid pIADK DNA. After 10 minutes incubation on ice, the cells were electroporated using a Gene Pulser (Biorad) to deliver one pulse of 250 volts, 960 µFd. The pulse cells were placed on ice for 10 minutes and added to 10 ml of IMDM medium (IMDM, 10% FBS, 2 mM glutamine, 5000 units/ml penicillin, 5000 (µg/ml streptomycin). Cells were incubated at 37° C., 5% CO$_2$ in a T25 tissue culture flask and 24 hr later, 20 mls of neomycin selective medium (IMDM medium, 1.5 mg/ml G418) was added. The cells were then transferred at 200 µl/well to 96 wells flat bottom tissue culture plates, incubated at 37° C., 5% CO$_2$ and fed neomycin selective media every 3–7 days. The pIADK vector carries a neomycin resistance gene that allows for selective growth of the stably-tranfected cells. Colonies of the cells transfected with the vector became evident after 14–21 days. The transfectants carrying the pIADK vector were expanded and were screened for expression of the soluble sc-class II-Cκ molecules by the IA$^d$-specific ELISA described previously. Purified sc-IA$^d$/OVA produced by insect cells served as the reference standard. The results of such an assay of the culture supernatants from four pIADK transfected cell lines are shown in the Table 5.

TABLE 5

Production of sc-IA$^d$/OVA-Cκ in Mammalian Cells

| Cell line | Soluble IA$^d$ Produced |
| --- | --- |
| NSOB7 | 81 ng/1 × 10$^6$ cells/day |
| NSOE2 | 156 ng/1 × 10$^6$ cells/day |
| NSOG4 | 116 ng/1 × 10$^6$ cells/day |
| NSOD4 | 109 ng/1 × 10$^6$ cells/day |

The results indicate that the soluble sc-IA$^d$-Cκ fusion molecules are produced in a form recognized by two conformation-specific antibodies. Based on these results, the NSOE2 transfectant was expanded and grown in a spinner flask in 2 liters of neomycin selective media.

The sc-IA$^d$-Cκ fusion molecules were purified as described in Example 7 which follows.

In addition, soluble production of a human sc-class II-Cκ fusion was tested in mammalian cells. CHO cells were transfected with the pDRHK expression vector and selected for growth in neomycin selective medium (see above). Stable transfectants were screened for production of soluble sc-DR2/MBP-Cκ molecules using two different ELISA formats. In the first format, anti-human kappa antibody was used as the capture Ab and HRP-conjugated L243 (ATCC HB-55) as the probe mAb. The L243 mAb is specific to conformational epitopes on HLA-DR molecules. Thus, this assay format detects properly folded DR2-Cκ fusions. In the second format, anti-HLA-DR L227 mAB (ATCC HB-96) was used as the capture Ab and HRP-conjugated L243 (ATCC HB-55) as the probe mAb. The L227 and L243 mAbs are specific to linear and conformational epitopes on HLA-DR molecules, respectively. This assay format detects the properly folded DR2 portion of the molecule. Antibody binding was detected by incubating with avidin peroxidase followed by ABTS substrate (Kirkegaard and Perry). The results of these assays are shown in Table 6.

TABLE 6

Production of scDR2/MBP-Cκ in Mammalian Cells

| Cell Line | ELISA Readings (Absorbance) Anti-kappa Ab: L243-HRP | L227 mAB: L243-HRP |
| --- | --- | --- |
| CHOE 12 | 1.056 | 0.245 |
| CHOA5 | 1.445 | 0.434 |
| CHO untransfected (negative control) | 0.078 | 0.071 |

The results indicate that the soluble sc-DR2/MBP-Cκ fusion molecules are produced by the transfected cells and released into the culture medium. The soluble-DR2/MBP-Cκ molecules are folded into a conformationally correct form.

2. Large-scale Expression of MHC Complexes in Mammalian Cells

The NSO and CHO cell expression systems described herein can be used to generate large amounts of the sc-MHC class II molecules (empty or covalently linked with peptides). For example, transfected CHO cell lines expressing the sc-DR2/MBP-Cκ molecules can be selected and grown to confluence in three separate hollow-fiber bioreactors. In accordance with standard bioreactor techniques, about 1×10$^9$ CHO cells can be inoculated into the extracapillary space (EC) of a hollow fiber bioreactor cartridge (Unisyn). Fresh oxygenated media is continuously circulated through the hollow fibers during growth of the transfected CHO cells. The soluble sc-MHC class II molecules are then harvested from the EC chamber (daily) for 30–120 days. It is expected that each bioreactor will yield about 0.1–1 gram amounts of each soluble MHC class II molecule.

EXAMPLE 7

Purification of Soluble sc-MHC Class I and Class II Molecules

Insect cell culture supernatants, from Example 5 above, were passed over a protein A Sepharose column. Unbound material was then applied to an MK-D6 mAb (see Kappler, J. W., B. Skidmore, J. White, P. Marrack. 1981. *J. Exp. Med.* 153:1198) protein A Sepharose column. The column was washed with 20 mM Tris-HCl, pH 8.0 and 1 M NaCl, 20 mM Tris-HCl, pH 8.0. The sc-IA$^d$ fusion protein was eluted with 50 mM glycine-HCl, pH 11.0 and immediately neutralized to pH 8.0. The fusion protein was concentrated and buffer-exchanged into 20 mM Tris-HCl, pH 8.0 using Centricon 30. These methods can be readily applied to the large-scale purification of soluble sc-class II molecules from culture supernatants produced by mammalian cells carrying the sc-class II genes. Typically, the purification procedure yielded 200–1000 μg of sc-IA$^d$/peptide molecules per liter of insect cell medium.

The purity of the preparation was evaluated by SDS-polyacrylamide gel electrophoresis (SDS-PAGE) of the eluate from the affinity column. The gel show showed major bands of approximately 50 kDa (FIG. 5A, lanes 1, 2 and 3). As expected, these molecules were glycosylated and showed slight differences in mass due to the linked peptide. Western blot analysis confirmed the presence of the OVA 323–339 peptide in the sc-IA$^d$/OVA protein samples (FIG. 5A, lane 5). In other protein detection assays, the purified immobilized sc-IA$^d$/OVA and sc-IA$^d$/blank proteins were independently bound by monoclonal antibodies which specifically bind the IA$^d$ (e.g., MK-D6, M5/114, AMS-32.1, 39-10-8, or 34-5-3). Other monoclonal antibodies capable of specifically binding MHC molecules are publicly available from several sources such as, e.g., the ATCC and Linscott's Directory at the addresses provided above.

In another example, affinity chromatographic methods using the MK-D6 mAb were employed to purify the sc-IA$^d$/OVA-Cκ fusion molecules from the mammalian tissue culture medium (see Example 6).

Methods for the immunoaffinity purification of MHC class II molecules have been described previously (Gorga, J. C., V. Horejsi, D. R. Johnson, R. Raghupathy, and J. L. Strominger. (1987) *J. Biol. Chem.* 262:16087). These methods can be generally employed to purify soluble sc-MHC class I or II proteins of the invention. For example, for sc-MHC class II fusion proteins carrying HLA-DR or HLA-DQ domains, the monoclonal antibodies L243 and G2a.5 (immunospecific for DR and DQ, respectively, and available from ATCC) can be used to immunopurify sc-MHC class II molecules which include these domains. In one example, these methods were employed to purify the sc-DR2Δβ2/MBP molecules produced in insect cells (see Example 5). The results of such a purification are shown in FIG. 5B.

As mentioned previously, soluble sc-class II molecules can be designed to include a tag. Such "tagged" molecules can be conveniently purified by standard techniques. For example, a molecule containing the 6xHis tag can be affinity purified on a Ni-IDA Sepharose Fast Flow column in general accordance with methods previously described. Briefly, the column is equilibrated with PBS, 0.5 M NaCl, 0.2% (v/v) Tween 20, pH 8.0. Following extensive washing, sc-MHC class II protein could be eluted with stepwise pH decreases effected by mixing different portions of Buffer A (20 mM Na$_2$HPO$_4$, pH 7.0, 0.2 M NaCl) and Buffer B (20 mM NaH$_2$PO$_4$, pH 3.0, 0.2 M NaCl). As another example, a soluble sc-MHC class II molecules containing the EE tag could be purified by conventional immunoaffinity chromatography using an anti-EE tag mAb-protein A Sepharose column. The sc-class II/IgG fusion molecules could be purified by conventional affinity chromatography using a protein A Sepharose column. See Ausubel et al. supra; and Sambrook et al. supra.

It will be apparent to those skilled in the art that the foregoing sc-MHC class II purification schemes can be readily adapted to the large-scale preparation and purification of other MHC molecules of the invention.

EXAMPLE 8
Formation of sc-MHC Class II/Peptide Complexes

To test whether the sc-IA$^d$/blank fusion molecules produced in Example 7 could productively bind peptide, the sc-IA$^d$/blank molecules were immobilized and then incubated for 20 hours at 37° C. with a 50 fold molar excess of OVA 323–339 in citrate buffer, pH 5.0. These complexes were washed twice with PBS and tested for their ability to stimulate T-cell responses by assays disclosed herein. Methods for loading peptides onto MHC class II molecules have been reported (see e.g., Stern, L. J. et al. supra). These methods could be readily applied to the loading virtually any presenting peptide to the MHC class II complex. In general, these methods involve incubation of the purified class II molecules with a 20–50 fold molar excess of peptide for 20–60 hours at 37° C. The optimal pH of these reactions vary depending upon the particular MHC class II molecule and peptide used, however, generally, the pH optimum for loading presenting peptides well be between about pH 4.5 to pH 7 (Sette, A., S. et al. (1992) *J. Immunol.* 148:844). The MHC class II/peptide complexes can be separated from free peptide by HPLC gel filtration, membrane filtration, immunoabsorption or spin ultrafiltration.

We found that the immobilized sc-IA$^d$/blank molecules produced in Example 7 were capable of productively binding peptide. See FIG. 6C.

EXAMPLE 9
Functionality of Soluble sc-MHC Class II/Peptide Complexes

The soluble sc-IA$^d$ class II molecules produced in Examples 4, 5 and 6, above were tested for their ability to stimulate IL-2 release from T-cell hybridoma cell lines in accordance with methods described herein. The soluble sc-IA$^d$/OVA and sc-IA$^d$/gD molecules (PBS, pH 7.0) were used to coated wells in 96-well Immulon II plates (Dynatech) overnight. The T-cell hybridoma DO11.10 cell line was then added to wells coated with sc-IA$^d$/OVA molecules, and the GD12 hybridoma cell line was added to sc-IA$^d$/gD coated wells (1×10$^5$ cells/well). When the TcRs of the DO11.10 cells interact with IA$^d$/OVA complexes, the cells secrete interleukin-2 (IL-2) and IL-4. As shown in FIG. 6A, immobilized sc-IA$^d$/OVA induced a dose-dependent release of IL-2 by DO11.10 cells. These results verify recognition of the sc-IA$^d$/peptide fusion molecule produced in Example 5 by the TcR of DO11.10 cells. As expected, DO11.10 cells failed to respond to the sc-IA$^d$/blank. Similar results were seen for the production of IL-4.

Further evidence of antigen specificity was obtained using the GD12 T-cell hybridoma. As shown in FIG. 6B, the GD12 cells responded well to immobilized sc-IA$^d$/gD but were not stimulated by the sc-IA$^d$/OVA molecules, whereas the DO11.10 cells showed the opposite response specificities.

Previous studies have shown that class II heterodimeric molecules produced in insect cells could bind exogenous added peptides (Stem, L. J., and D. C. Wiley (1992) *Cell* 68:465, Scheirle, A., B. et al. (1992) *J. Immunol.* 149:1994, Kozono, H., supra). However, it was also found that IA$^d$ α and β chain dissociate and are not capable of presenting peptide (Kozono, H., supra). To tested whether the sc-IA$^d$ MHC class II molecule produced in Example 5 were stable and capable of loading a suitable presenting peptide, purified sc-IA$^d$/blank molecules were incubated with OVA 323–339 peptide in accordance with methods described herein (e.g., see Example 8). Following washing to remove unbound peptides, immobilized complexes were found to activate DO11.10 cells (FIG. 6C). Together these results indicate that the single-chain format stabilizes the IA$^d$ molecules to allow for purification and loading with exogenously added or covalently attached peptides.

In another example, the DO11.10 cytokine release assay was used to test the functionality of the sc-IA$^d$-Cκ fusion molecules produced in Example 6. Briefly, purified sc-IA$^d$-Cκ fusion protein (1.1 μg/well) was coated on a 96 well plate. Insect cell derived sc-IA$^d$ molecules (1.1 μg/well) served as controls. Alternatively, polyclonal anti-mouse kappa antibody (200 ng/well) was initially coated on the plate and fusion protein (1.1 μg/well) was added and captured by the anti-kappa antibody. The plates were washed twice with PBS and 1×10$^5$ DO11.10 T-cells (200 μl) were added. After 24 hours at 37° C., the culture supernatant was collected and the amount of IL-2 released into the culture medium by the DO11.10 T-cells was determined by ELISA (PharMingen). Release of IL-2 is a measure of the level of T-cell activation following the functional interaction between the DO11.10 T-cell receptor and the IA$^d$/OVA complex. The results of the IL-2 ELISA are shown in Table 7.

TABLE 7

Functionality of the sc-IA$^d$-Cκ fusion molecules

| Immobilized protein | DO11.10 IL-2 Released (pg/well) |
| --- | --- |
| NSOE2 sc-IA$^d$/OVA-Cκ | 500 |
| Insect cell sc-IA$^d$/OVA (positive control) | 528 |
| Insect cell sc-IA$^d$/gD (negative control) | 0 |
| anti-kappa captured NSOE2 sc-IA$^d$/OVA-Cκ | 72 |

The results indicate that the sc-IA$^d$/OVA-Cκ are functionally active either when immobilized or when captured by the anti-kappa antibody. These results were unexpected since we found that the analogous fusion between the sc-IA$^d$ and the IgG CH2–CH3 domains resulted in molecules that were not recognized by IA$^d$-specific ELISA assay or the T-cell stimulation assay.

EXAMPLE 10
Soluble sc-IA$^d$/Peptide Fusion Complexes Induce Apoptosis

DO11.10 cells were used to test the ability of soluble sc-IA$^d$ fusion molecules to induce T-cell apoptosis. After an overnight incubation with the soluble sc-IA$^d$/OVA molecule described above, DO11.10 cells showed marked changes in cell morphology, including nuclear condensation, the appearance of apoptotic bodies and degradation of the DNA into oligonucleosomal bands (FIG. 7, lane 4). These changes are characteristic of apoptosis [P. Walker et al., *BioTechniques*, 15:1032 (1993)]. Similar effects were observed in cells incubated with anti-TcR and anti-CD3 mAbs, whereas no changes in cell morphology or DNA degradation were observed in the cell incubated with immobilized sc-IA$^d$/blank (compare lanes 3 and 5 of FIG. 7).

FIG. 7 is explained as follows: DO11.10 cells were incubated in untreated wells or in wells coated with 100 ng/well anti-TcR mAb (H57–597, PharMingen), or 250 ng/well sc-IA$^d$ molecules. After 24 hours, the cells (1.2× 10$^6$/sample) were harvested and Triton X-100 soluble/DNA was isolated [P. Walker et al., Bio Techniques, 15:1032 (1993)]. Samples were analyzed by 2% agarose gel electrophoresis and stained with ethidium bromide to detect chromosomal DNA laddering. Lane 2 is from untreated DO11.10 cells. Lanes 1 and 6 show DNA molecular weight markers.

EXAMPLE 11
DNA Inoculation with Vectors Comprising Soluble sc-IA$^d$ MHC Fusion Molecules Suppress T-cell Expansion in Vivo.

At least two signals are needed for the activation of T-cells, e.g., as in the proliferation of T-cells. A single signal delivered to the T-cell via the TcR and MHC class II/peptide fusion complex will kill or anergize the T-cells. It was found that soluble sc-IA$^d$/OVA fusion molecules selectively kill antigen specific T-cells in vivo in the absence of added co-stimulatory signals. These results indicate that single chain MHC molecules, particularly single chain MHC class II molecules, are well suited for suppressing immune system function in vivo. The results also indicate that immune system function can be induced when a single chain MHC molecule is co-expressed in cells with a co-stimulatory signal or, alternatively, when a single chain MHC molecule is expressed in cells where a suitable co-stimulatory signal already exists in the cells.

To suppress the clonal expansion of T-cells in vivo, we used the mammalian expression vector pEE13 which can be modified to carry the sc-$IA^d$/OVA fusion gene by standard methods. Transcription of the sc-$IA^d$/OVA gene was driven by the CMV promoter of the expression vector. BALB/c mice were injected with 100 $\mu$g of plasmid DNA (1 mg/ml in PBS) intramuscularly (IM) in the hind legs. Injections were repeated two more times 14 and 28 days later. A control group was injected IM with saline on week 0 and 100 $\mu$g of a plasmid encoding sc-$IA^d$/blank on weeks 2 and 4.

Both groups were then injected subcutaneously at the base of the tail with OVA 323–339 peptide (100 $\mu$g/mouse in complete Freunds H37Ra adjuvant) at 23 and 30 days after the final DNA inoculation. One week later, the mice were killed and the inguinal and paraaortic lymph nodes collected. A lymph node cell suspension was prepared and depleted of antigen presenting cells by incubation on nylon wool and Sephadex G-10 columns, and the resulting purified T-cell populations were incubated with APCs pulsed with the OVA 323–339 peptide. Splenic B cells from a BALB/c mouse served as APCs. These cells were fixed with mitomycin C (50 to 100 $\mu$g/ml in s suspension of $4\times10^6$ spleenocytes/ml) to inhibit proliferation of the B cells, washed extensively and added to purified T-cells ($2\times10^5$ cells/well) with the OVA 323–339 peptide (0 to 50 $\mu$g/well). The cells were allowed to proliferate in 96 well round bottom microtiter plates at 37° C., 5% $CO_2$ for 4 days. At this time, wells were pulsed with MTS (40 $\mu$l/well) (Promega) for 4 to 6 hours prior to termination of cultures. Incorporation of MTS was determined by measuring absorbance at 490 and is a measure of T-cell proliferation.

FIG. 8A and FIG. 8B show the results of T-cell proliferation assays using cells from injected and control mice. In FIG. 8A, the T-cells were isolated from mice receiving IM injections of the sc-$IA^d$/blank plasmid (and saline). In FIG. 8B, mice received IM injections of the sc-$IA^d$/OVA plasmid. Mice were challenged twice with the OVA peptide and T-cells were isolated from the lymph nodes one week later. OVA-specific T-cell proliferation assays were carried out as described above. T-cells isolated from mice injected with the sc-$IA^d$/OVA plasmid showed a significant reduction in the amount of OVA-specific proliferation compared those isolated from the control group injected with the sc-$IA^d$/blank plasmid. These results show that expression of soluble sc-$IA^d$/OVA molecules suppresses the clonal expansion of antigen-specific T-cells in vivo.

Administration of soluble single chain MHC molecules (e.g., soluble sc-MHC class II peptide fusion complexes or soluble loaded sc-MHC class II complexes) or DNA expression vectors coding for these molecules will alleviate immune disorders in mammals, particularly humans, which involve the undesirable presence or expansion of antigen specific T-cells. For example, soluble single chain MHC molecules (e.g., soluble sc-MHC class II peptide fusion complexes) or DNA expression vectors coding for these molecules can be admixed with a pharmaceutically acceptable carrier substance, e.g., physiological saline, and administered to a mammal, e.g., a human, suffering from or likely to suffer from an immune disorder which involves the undesirable presence or expansion of antigen specific T-cells. Examples of other pharmaceutically acceptable carriers are well known (see e.g., *Remington's Pharmaceutical Sciences*, Mack Pub. Co., Easton, Pa., 1980). One particular mode of administration is intramuscular, although other modes may be used (e.g., oral, nasal, intravenous, parentaeral, or transdermal), which mode will depend upon the condition being treated and the general status of the animal and will be apparent to those skilled in the art. The dosage of the soluble single chain MHC fusion molecule will also vary, depending on such factors as the type and severity of the immune disease, but will generally be at a dosage sufficient to suppress the in vivo expansion of immune cells such as antigen specific T-cells. A typical dosage range would be 1 ng to 10 mg of the soluble MHC class II molecule per kg body weight. Treatment may be repeated as deemed necessary, e.g., each day. Similar suitable doses can be used for the administration of the polyspecific MHC complexes disclosed herein (loaded or with recombinantly fused presenting peptide).

It will also be understood that cells bearing all or most MHC molecules of the invention can be administered to a mammal at a dosage sufficient to suppress or induce T-cells. T-cell activity can be detected by assays described herein.

It will be apparent that other soluble loaded single chain MHC molecules can be used to treat the undesirable presence or expansion of antigen specific T-cells in vivo. For example, a presenting peptide of about 6 to 30 amino acids (inclusive) can be mixed in at least an equimolar ratio with a suitable soluble empty single chain MHC molecule to form the corresponding loaded molecule. The loaded molecule can then be admixed with a pharmaceutically acceptable carrier and administered to a mammal, e.g., a human, to treat an immune system disorder as described above.

EXAMPLE 12

Immunosuppressive Approach by DNA Inoculation with Vectors Expressing Peptide-linked Single-chain MHC Molecules An example of a model system for testing the effects of the DNA inoculation approach (particularly intramuscular or intradermal) is as follows. Three groups of BALB/c mice are injected intramuscular (IM) in both hind legs with 100 $\mu$g of: (1) SCE1, (b) SCT1, or (c) saline. Injections will be given at 0, 2, and 4 weeks. At 4 and 5 weeks after the initial DNA injection, OVA peptide 323–339 (100 μg/mouse in complete Freunds H37Ra adjuvant) is injected subcutaneously at the base of the tail. Two weeks later (week 8), blood is collected from each mouse by tail bleeding and serum obtained following centrifugation at approximately 14,000 G for 3–5 minutes. Titers of OVA-specific IgG and IgM antibodies is determined as described above. The degree of OVA-specific IgG antibody is indicative of the $T_H$ cell directed immunoglobin class switching that took place in the mice following immunization with the peptide. Therefore, DNA inoculation with the peptide-linked single-chain MHC expression vectors may cause a reduction in the level of peptide-specific IgG antibodies without effecting IgM antibody levels.

An alternative assay is to measure OVA-specific $T_H$ cell clonal expansion or proliferation. Briefly, a cell suspension will be prepared from the inguinal and paraaortic lymph notes 7 days after the second OVA immunization. The suspension is depleted of antigen presenting cells by incubation on nylon wool and Sephadex G-10 columns, and the resulting purified T-cell populations incubated with APCs pulsed with the OVA 323–339 peptide. Spleenic B cells serve as antigen presenting cells. These cells are fixed with mitomycin C (50 to 100 μg/ml in a suspension of $4\times10^6$ spleenocytes/ml) to inhibit proliferation of the B cells, washed extensively and added to purified T-cells with various concentrations of the OVA 323–339 peptide. The OVA-specific T-cell proliferation assay is carried out as described above. The degree of peptide-reactive T-cell proliferation is indicative of the TH cell responses (i.e. of clonal expansion) that took place in the mice following immunization with the peptide. Therefore, DNA inoculation with the peptide-linked single-chain MHC expression vectors may cause a reduction in the level of peptide-specific TH cell proliferation.

EXAMPLE 13

Immunosuppression Using Soluble Peptide-linked Single-chain MHC Class II Molecules The soluble peptide-linked sc-class II molecules produced in accordance with Examples 4,5, and 6 above are suited for inducing a state of anergy in $T_H$ cells. To test this, the effects of the molecules on $T_H$ cell-dependent immunoglobin class switching (i.e. IgM to IgG) and on clonal expansion of peptide-specific T-cell lines can be examined by the following method.

a) IgG Class Switching

In order to examine IgM to IgG class switching, two test groups are set up as follows:

i) 10 BALB/c mice are injected with 100 pg of OVA 323–339 in Complete Freund's adjuvant H37Ra at the base of the tail and boosted again 7 days later to induce an immune response to the OVA 323–339 peptide. On the day before and the day of each immunization with OVA, 5 of the mice are injected IV with 10–100 micrograms of the soluble sc-IA$^d$/OVA in PBS. This soluble fusion protein can bind to the T-cell receptor TcR displayed on the OVA 323–339 specific $T_H$ cells. Due to the absence of a co-stimulatory signal, these $T_H$ cells are induced to a state of anergy. Since the immunoglobulin class switching is a $T_H$ cell dependent process, it is expected that the induction of anti-OVA 121–339 IgG antibody is dramatically reduced in the sc-IA$^d$/OVA treated mice. The remaining 5 mice serve as control and are to receive PBS. These mice are expected to accumulate anti-OVA 323–339 IgG antibody due to the unhampered $T_H$ cells.

Ten days after the second immunization, blood is collected from each mouse by tail bleeding. The blood is centrifuged at approximately 14,000 G for 3–5 minutes and the serum collected. Assays are to be performed in 96-well microtiter plates (Maxisorp F8; Nunc, Inc.) coated at 1–50 microgram/ml with ovalbumin using a Tris-HCL coating buffer, pH 8.5. The plates are then covered with pressure sensitive film (Falcon, Becton Dickinson, Oxnard, Calif.) and incubated overnight at 4° C. Plates are then be washed with Wash solution (Imidazole/NaCl,0.4% Tween-20) and blocked by adding 100 microliters/well of a 3% BSA solution. Following incubation on a plate rotator at room temperature for 30 minutes, the plates are washed five times with Wash solution. Mouse sera are then diluted 1:500 in sample/conjugate diluent (2% gelatin+0.1% Tween-20 in TBS) and then, in duplicate, serially diluted on the plate. Two identical plates are set up for each coating protein, one for determination of IgM titer and the other for IgG. Following incubation at room temperature for 30 minutes, the plates are washed five times with Wash solution. Goat anti mouse IGM-HRP and goat anti-mouse IgG-HRP conjugates (Boehringer Mannheim, Indianapolis, Ind., 1:100 dilution in sample/conjugate diluent) are added to the appropriate plates. Following incubation at room temperature for 30 minutes, the plates are washed five times with Wash solution and then incubated with 100 microliters/well of ABTS developing substrate (Kirkgaard & Perry Laboratories, Inc., Gaithersburg, Md.) for 10 minutes at room temperature. The reactions are stopped with a 100 microliter/well of Quench buffer (Kirkgaard & Perry Laboratories, Inc., Gaithersburg, Md.) and the absorbance values read at 405 mn using an automated microliter plate ELISA reader (Ceres UV900HI, Bioteck, Winooski, Vt.). The titer is determined by plotting the absorbance reading versus the log of the dilutions of the samples. The titers for IgM versus IgG are then compared.

The soluble peptide-linked single-chain MHC class II molecules produced in Examples 4, 5 and 6 are expected to inhibit IgG class switching in a peptide specific manner due to the anergy induced in the corresponding peptide-reactive $T_H$ cells.

b) Clonal Expansion of Peptide-specific T-cell Lines In-vivo

The effects of the soluble peptide-linked single-chain class II molecules produced in Examples 10–11 on the clonal expansion of peptide-specific T-cell lines can be examined in vivo as follows. The treatment groups (4 mice per group) are to be identical to those described above. The immunization protocol is as follows: mice are injected IV with 10–100 microgram of the soluble sc-IA$^d$/OVA fusion protein in PBS and 24 hours later injected subcutaneously at the base of the tail with 50 micrograms of OVA 323–339 in complete Freunds Adjuvant H37Ra. These two injections are repeated 6 and 7 days later. Seven days after completion of the second set of injections, the mice are sacrificed. The inguinal and paraaortic lymph nodes are removed and rendered into a single cell suspension.

The suspension is depleted of antigen presenting cells by incubation on nylon wool and Sephadex G-10 columns, and the resulting purified T-cell populations are incubated with APCs pulsed with the OVA 323–339 peptide. Spleenic B cells are to serve as antigen presenting cells. These cells are fixed with mitomycin C (50 to 100 microgram/ml in a suspension of $4\times10^6$ spleenocytes/ml) to inhibit proliferation of the B cells, washed extensively and then added to purified T-cells with various concentrations of the OVA 323–339 peptide. The proliferation assay is carried out in 96 well round bottom microtiter plates at 37° C., 5% CO2 for 3–5 days. Wells are pulsed with 1 microCurie of 3H-thymdine 18 hrs prior to termination of cultures and harvested using a Skatron cell harvester. Incorporation of 3H-thymidine into DNA as a measure of T-cell proliferation will be determined using an LKB liquid scintillation spectrometer. The degree of peptide-reactive T-cell proliferation is indicative of the $T_H$ cell responses (i.e. of clonal expansion) that took place in the mice following immunization.

It is expected that co-injection of the soluble single-chain MHC class II molecules produced in Examples 4, 5, and 6 (combined with OVA immunization) will limit the amount of clonal expansion and subsequent in vitro proliferation of OVA-reactive T-cell lines.

EXAMPLE 14
Preparation of Polyspecific MHC Class II Complexes

As discussed above, fully soluble and functional MHC complexes of the invention include polyspecific complexes. There follows exemplary methods of making polyspecific MHC molecules comprising a sc-MHC class II molecule and a ligand binding molecule.

1. Bispecific Complex

A. Immunoglobin Joining Molecules

FIGS. 9A and 9B show examples of bispecific complexes comprising two sc-MHC class II peptide fusion molecules or a sc-MHC class II peptide fusion molecule and a single-chain antibody, respectively.

The bispecific complex comprising two sc-MHC class II peptide complexes (FIG. 9A) can be made according to the methods described herein. For example, in one approach, a first fusion molecule comprising covalently linked in sequence a sc-MHC molecule (e.g., a class II sc-MHC molecule), a joining molecule (e.g., an Ig-$C_L$ chain), and an optional effector molecule is constructed. The fusion molecule can be combined with a second fusion molecule comprising covalently linked in sequence a sc-MHC class II peptide fusion molecule a joining molecule (e.g., a Ig-$C_L$ chain) and an optional effector molecule. As noted earlier, the sc-MHC class II molecule can include a β2 class II chain modification such as a deletion of essentially the entire β2 chain to improve soluble expression if desired. The first and second fusion molecules can be encoded by a DNA sequence, preferably a vector encoding both molecules. Alternatively, the first and second fusion molecules can be encoded by separate DNA sequences, preferably included on two DNA vectors, in which case each DNA sequence encodes one of the fusion molecules. In either case, the first and second fusion molecules are expressed as discreet chains and can be combined in vitro or in suitable mammalian cells to form the bispecific complex. The bispecific complex can be purified if desired to form substantially pure complex in accordance with the isolation and purification methods described above.

The bispecific complex depicted in FIG. 9B comprising a sc-MHC class II peptide fusion molecule and a single-chain antibody can be made generally along the lines described above, except that the second fusion molecule will comprise covalently linked in sequence a sc-Fv antibody, a joining molecule (e.g., an IgG$C_H^1$ molecule) and an optional effector molecule.

B. Other Joining Molecules

As mentioned above, a variety of polypeptides have been shown to form specific binding pairs. For example, coiled coils (such as a leucine zipper), helix-turn-helix polypeptide motifs and related structures have been shown to facilitate dimerization and oligomerization of single-chain antibody Fv fragments, the α and β chain of T-cell receptor molecules, and the α and the β chains of MHC class II molecules. See e.g., Pack et al., *Biotechnology*, 11:1271 (1993); Pack et al., *J. Mol. Biol.*, 246:28 (1995); Chaing et al., *Proc. Natl. Acad. Sci. USA* 91:11408 (1994); Scott et al., *J. Exp. Med.*, 183:2087 (1996).

In accordance with known methods of making and using coiled coil and helix-turn-helix structures, it is an object of the present invention to construct a bispecific complex comprising such coiled coil or helix-turn-helix joining molecules. The bispecific complex can be made by several molecules including the following steps. First, a pair of oligonucleotide DNA primers can be made by standard synthetic methods in which each primer encodes the following coiled-coil sequences:

1. NH2-SSADLVPRGSTTAPSAQLEKELQALEKENA QLEWELQALEKELAQ-COOH (SEQ ID NO: 33)
    2. NH2-SSADLVPRGSTTAPRAQLKKKLQALKKKNA QLKWKLQALKKLAQ-COOH (SEQ ID NO: 34)

See Scott et al., *J. Exp. Med.*, 183:2087 (1996).

Alternatively, each of the DNA oligonucleotide primers can encode a suitable portion of the coiled-coil sequence of SEQ ID NO: 33 and SEQ ID NO: 34 provided that the pair of encoded sequences are capable of forming a specific binding pair as determined, e.g., by tests reported by Pack et al. supra, Chaing et al., supra and Scott et al. supra.

Next, to construct a bispecific MHC complex comprising the coiled-coil joining molecules or a suitable fragment thereof, one of the DNA oligonucleotide primers is covalently linked to the 3' end of a DNA segment encoding one or more sc-MHC molecules of interest, e.g., a sc-MHC class II molecule. The DNA construct thus made is then optionally linked at the 3' end of the primer to the 5' end of a DNA sequence encoding a desired optional effector molecule. The second DNA oligonucleotide primer is covalently linked to the 3' end of a DNA segment encoding a desired ligand binding molecule such as a DNA segment encoding e.g., a single-chain antibody of interest. The DNA construct thus made can be further fused to the 5' end of a DNA segment encoding a desired optional effector molecule. As specific examples, the DNA segments can include covalently linked in sequence: a sc-MHC class II molecule/coiled-coil sequence; sc-MHC class II molecule/coiled-coil sequence/effector molecule; single-chain antibody/coiled-coil sequence; single-chain antibody/coiled-coil sequence/effector molecule.

A selected pair of the DNA segments will typically be those which are capable of encoding protein capable of dimerization. In general, the selected pair of DNA segments will be introduced into a pair of suitable vectors for expression in a desired cell type. Alternatively, the DNA segments can be inserted on a single DNA vector as desired. A bispecific complex according to the invention can be produced by alternative strategies. In one approach, each of the vectors encoding one of the complex chains is introduced in cells, wherein the cells are cultured under conditions which produce the encoded protein. Protein is isolated separately from each cell culture and then combined in vitro under controlled conditions of temperature, salt, protein and ion concentration, etc. to maximize formation of the bispecific MHC complex. Alternatively, both vectors can be introduced into the same suitable cells, wherein the cells are cultured under conditions which favor expression and assembly of the desired bispecific MHC complex. The bispecific MHC complex can be isolated from the cell in substantially pure form if desired in accordance with methods described herein. Examples of suitable cells and vectors have been discussed above.

The invention has been described with reference to preferred embodiments thereof. However, it will be appreciated that those skilled in the art, upon consideration of this disclosure, may make modifications and improvements within the spirit and scope of the invention.

What is claimed is:

1. A sc-MHC class II fusion protein comprising a recombinantly fused polypeptide comprising: i) a presenting peptide and ii) a class II β2 chain comprising at least one amino acid substitution or deletion; wherein the β2 chain increases expression of the fusion protein relative to sc-MHC class II fusion protein comprising the class II β2 chain without the amino acid substitution or deletion.

2. The sc-MHC class II fusion protein of claim 1 further comprising an immunoglobin light chain constant region or fragment thereof.

3. The sc-MHC class II fusion molecule of claim 1, wherein the class II β2 chain amino acid deletions are contiguous or non-contiguous.

4. The sc-MHC class II fusion molecule of claim 1, wherein the class II β2 chain amino acid substitutions minimize or eliminate cross linking between Cys residues of the class II β2 chain.

5. The sc-MHC class II fusion molecule of claim 4, wherein the class II β2 chain amino acid substitutions are contiguous or non-contiguous.

6. A sc-MHC class II fusion protein comprising a recombinantly fused polypeptide comprising i) a presenting peptide and ii) a immunoglobin light chain constant region or fragment thereof; wherein the immunoglobin light chain constant region or the fragment increases expression of the fusion protein relative to the sc-MHC class II fusion protein without the immunoglobin light chain constant region or fragment.

7. The sc-MHC class II fusion molecule of claim 1 or 6, wherein the fusion molecule comprises a class II IA, IE, DR, DQ or DP MHC molecule.

8. The sc-MHC class II fusion molecule of claim 1 or 6, wherein specific binding of the fusion protein with peptide antigen is not reduced by more than 30%.

9. The sc-MHC class II fusion molecule of claim 1 or 6, wherein the increase in expression is detected by ELISA.

10. A sc-MHC class II fusion molecule comprising a peptide-binding groove, the sc-MHC class II fusion molecule comprising covalently linked in sequence:
 a) a presenting peptide,
 b) an MHC class II β1 chain or a presenting-peptide binding portion thereof,
 c) a modified MHC class II β2 chain comprising at least one amino acid substitution or deletion; wherein the β2 chain increases expression of the fusion protein,
 d) a peptide linker sequence; and
 e) an MHC class II α1α2 chain or a presenting-peptide binding portion thereof,
wherein the increase in expression is relative to sc-MHC class II fusion protein comprising: i) the presenting peptide, ii) the MHC class II β1 chain or presenting-peptide binding portion thereof, iii) the peptide linker sequence, iv) the MHC class II α1α2 chain or a presenting-peptide binding portion thereof, and v) the class II β2 chain without the amino acid substitution or deletion.

11. The sc-MHC class II fusion molecule of claim 10, wherein the class II β2 chain deletion comprises deletion of at least 2, 5, 10, 25, 50, 60, 70, 80, 90 or greater amino acids of the class II β2 chain.

12. The sc-MHC class II fusion molecule of claim 11, wherein the class II β2 chain amino acid deletion is all of the class II β2 chain.

13. The sc-MHC class II fusion molecule of claim 10, wherein the class II β2 chain comprises a substitution of 2, 5, 10, 25, 50, 60, 70, 80, 90 or greater amino acids of the class II β2 chain.

14. The sc-MHC class II fusion molecule of claim 13, wherein the class II β2 chain substitution comprises a $Cys^{117}$ to $Ser^{117}$ substitution.

15. The sc-MHC class II fusion molecule of claim 10 further comprising an immunoglobin light chain constant region fragment covalently linked to the MHC class II α1α2 chain or the presenting-peptide binding portion thereof.

16. A sc-MHC class II fusion molecule comprising a peptide-binding groove, wherein the fusion molecule comprises covalently linked in sequence:
   a) a presenting peptide,
   b) an MHC class II β1 β2 chain or a presenting-peptide binding portion thereof,
   c) a peptide linker sequence,
   d) an MHC class II α1α2 chain or a presenting-peptide binding portion thereof, and
   e) an immunoglobin light chain constant region (Ig-$C_L$) or fragment thereof; wherein the immunoglobin light chain constant region or fragment increases expression of the fusion protein,
wherein the increase in expression is relative to sc-MHC class II fusion protein comprising: i) the presenting peptide, ii) the MHC class II β1 chain or presenting-peptide binding portion thereof, iii) the peptide linker sequence, and iv) the MHC class II α1α2 chain or a presenting-peptide binding portion thereof, with the proviso that the sc-MHC class II fusion protein not comprise the immunoglobin light chain constant region or fragment.

17. The sc-MHC class II fusion molecule of claim 16, wherein the immunoglobin light chain constant region fragment is a murine or human Cκ chain.

18. The empty sc-MHC class II molecule of claim 16, wherein the immunoglobin light chain constant region fragment is a murine or human Cλ chain.

19. The sc-MHC class II fusion molecule of claim 17 or 18 wherein the immunoglobin light chain constant region (Ig-$C_L$) fragment is between about 80 to 130, 90 to 120, or 100 to 110 amino acids in length.

20. A sc-MHC class II fusion protein comprising covalently linked in sequence:
   1) a melittin signal peptide consisting of the following sequence: M-K-F-L-V-N-V-A-L-V-F-M-V-V-Y-I-S-Y-I-Y-A as shown in SEO ID NO. 36,
   2) a modified MBP sequence as shown in SEQ ID NO. 28,
   3) an L1 linker sequence as shown in SEQ ID NO. 29,
   4) a DRB1*1501 β1-Δβ2 fragment consisting of amino acids 1 to 94 as shown in SEQ ID NO. 37,
   5) an L2 linker sequence as shown in SEQ ID NO. 29,
   6) a DRA1α1-α2 sequence consisting of amino acids 1 to 192 as shown in SEQ ID NO. 38; and
   7) an antibody tag as shown in SEQ ID NO. 30.

* * * * *

SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
         (A) LENGTH: 8 base pairs
         (B) TYPE: nucleic acid
         (C) STRANDEDNESS: single
         (D) TOPOLOGY: linear (xi) SEQUENCE DESCRIPTION: SEQ ID NO: 1:

CCACCATG                                                                        8

(2) INFORMATION FOR SEQ ID NO: 2:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (xi) SEQUENCE DESCRIPTION: SEQ ID NO: 2:

CCCCCCAAGC TTCCGGGCCA CCATGGCTCT GCAGATCCCC AGC                                 43

(2) INFORMATION FOR SEQ ID NO: 3:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO: 3:

CCCCCCACTT AAGGTCCTTG GGCTGCTCAG CACC                                           34

(2) INFORMATION FOR SEQ ID NO: 4:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (xi) SEQUENCE DESCRIPTION: SEQ ID NO: 4:

GGGGGGGCCA TGGCCGGAAA CTCCGAAAGG CATTTCG                                        37

(2) INFORMATION FOR SEQ ID NO: 5:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (xi) SEQUENCE DESCRIPTION: SEQ ID NO: 5:

GCGGCGACTA GTCCACTCCA CAGTGATGGG GC                                             32

(2) INFORMATION FOR SEQ ID NO: 6:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (xi) SEQUENCE DESCRIPTION: SEQ ID NO: 6:

GGGGGGGCCA TGGCCGAAGA CGACATTGAG GCCGAC                          36

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 7:

GCGCGACTAG TCCAGTGTTT CAGAACCGGC TC                              32

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 8:

GGGGGGGATA TCTCTCAGGC TGTTCACGCT G                               31

(2) INFORMATION FOR SEQ ID NO: 9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO: 9:

GGGGGGTTCG AAAAGTGTAC TTACGGGGGG CTGGAATCTC AGGTTC               46

(2) INFORMATION FOR SEQ ID NO: 10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 10:

GGGGGGCTCG AGTATCAAAG AAGAACATGT GATCATC                         37

(2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 11:

GCGGCGGGAT CCGTTCTCTG TAGTCTCTGG GAGAGG                          36

(2) INFORMATION FOR SEQ ID NO: 12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 12:

GATAAGAGGA AGAAGAGTAC ATGCCGATGG AACCCGGGTG AG                                42

(2) INFORMATION FOR SEQ ID NO: 13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 13:

AATTCTTCAC CCGGGTTCCA TCGGCATGTA CTCTTCTTCC TCG                               43

(2) INFORMATION FOR SEQ ID NO: 14:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO: 14:

CCCCCCGCTA GCGGAGGGGG CGGAAGCGGC GGAGGGGGGG ACACCCGACC ACGTTTCCTG             60

TGGCAGCCTA AGAGG                                                             75

(2) INFORMATION FOR SEQ ID NO: 15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 15:

CCCCCCGAAT TCCCCACTAG TCCATTCCAC TGTGAGAGGG CTTGTCAC                          48

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 16:

GGGGGGGCCA TGGCCTACGA CAGAACCCCG TGGTG                                        35

(2) INFORMATION FOR SEQ ID NO: 17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 17:

GGGGGGACTA GTTCGCCGCT GCACTGTGAA GC                                           32

(2) INFORMATION FOR SEQ ID NO: 18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 18:

GGGGGGTATG CATACGACGA GAACCCCGTG GTG                                    33

(2) INFORMATION FOR SEQ ID NO: 19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 19:

GGGGGGACTA GTCCACTTCG AGGAACTGTT TCC                                    33

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 20:

CCTCCTGGTC TCCTCTGTGA GTGG                                              24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 21:

CCACTCACAG AGGAGACCAG GAGG                                              24

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 22:

CCCCCCACCG GTTACGACAA GCCCGTGGTG                                        30

(2) INFORMATION FOR SEQ ID NO: 23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 23:

CCCCCCATCG ATAAGTGTAC TTACGTGGGA GAGGGCTTGG AGCAT                       45

(2) INFORMATION FOR SEQ ID NO: 24:

(i) SEQUENCE CHARACTERISTICS:
        (A) LENGTH: 1508 base pairs
        (B) TYPE: nucleic acid
        (C) STRANDEDNESS: single
        (D) TOPOLOGY: linear (ix) FEATURE:
    (A) NAME/KEY: Coding Sequence
    (B) LOCATION: 6...1505
    (D) OTHER INFORMATION:

(xi) SEQUENCE DESCRIPTION: SEQ ID NO: 24:

```
CCACC ATG GCT CTG CAG ATC CCC AGC CTC CTC CTC TCA GCT GCT GTG GTG         50
      Met Ala Leu Gln Ile Pro Ser Leu Leu Leu Ser Ala Ala Val Val
      1               5                  10                  15

GTG CTG ATG GTG CTG AGC AGC CCA AGG ACC TTA AGT ATC TCT CAG GCT           98
Val Leu Met Val Leu Ser Ser Pro Arg Thr Leu Ser Ile Ser Gln Ala
            20                  25                  30

GTT CAC GCT GCT CAC GCT GAA ATC AAC GAA GCT GGT CGT GCT AGC GGA          146
Val His Ala Ala His Ala Glu Ile Asn Glu Ala Gly Arg Ala Ser Gly
                35                  40                  45

GGG GGC GGA AGC GGC GGA GGG GGA AAC TCC GAA AGG CAT TTC GTG GTC          194
Gly Gly Gly Ser Gly Gly Gly Gly Asn Ser Glu Arg His Phe Val Val
            50                  55                  60

CAG TTC AAG GGC GAG TGC TAC TAC ACC AAC GGG ACG CAG CGC ATA CGG          242
Gln Phe Lys Gly Glu Cys Tyr Tyr Thr Asn Gly Thr Gln Arg Ile Arg
65                  70                  75

CTC GTG ACC AGA TAC ATC TAC AAC CGG GAG GAG TAC GTG CGC TAC GAC          290
Leu Val Thr Arg Tyr Ile Tyr Asn Arg Glu Glu Tyr Val Arg Tyr Asp
80                  85                  90                  95

AGC GAC GTG GGC GAG TAC CGC GCG GTG ACC GAG CTG GGG CGG CCA GAC          338
Ser Asp Val Gly Glu Tyr Arg Ala Val Thr Glu Leu Gly Arg Pro Asp
                100                 105                 110

GCC GAG TAC TGG AAC AGC CAG CCG GAG ATC CTG GAG CGA ACG CGG GCC          386
Ala Glu Tyr Trp Asn Ser Gln Pro Glu Ile Leu Glu Arg Thr Arg Ala
            115                 120                 125

GAG GTG GAC ACG GCG TGC AGA CAC AAC TAC GAG GGG CCG GAG ACC AGC          434
Glu Val Asp Thr Ala Cys Arg His Asn Tyr Glu Gly Pro Glu Thr Ser
            130                 135                 140

ACC TCC CTG CGG CGG CTT GAA CAG CCC AAT GTC GCC ATC TCC CTG TCC          482
Thr Ser Leu Arg Arg Leu Glu Gln Pro Asn Val Ala Ile Ser Leu Ser
145                 150                 155

AGG ACA GAG GCC CTC AAC CAC CAC AAC ACT CTG GTC TGT TCG GTG ACA          530
Arg Thr Glu Ala Leu Asn His His Asn Thr Leu Val Cys Ser Val Thr
160                 165                 170                 175

GAT TTC TAC CCA GCC AAG ATC AAA GTG CGC TGG TTC AGG AAT GGC CAG          578
Asp Phe Tyr Pro Ala Lys Ile Lys Val Arg Trp Phe Arg Asn Gly Gln
                180                 185                 190

GAG GAG ACA GTG GGG GTC TCA TCC ACA CAG CTT ATT AGG AAT GGG GAC          626
Glu Glu Thr Val Gly Val Ser Ser Thr Gln Leu Ile Arg Asn Gly Asp
            195                 200                 205

TGG ACC TTC CAG GTC CTG GTC ATG CTG GAG ATG ACC CCT CAT CAG GGA          674
Trp Thr Phe Gln Val Leu Val Met Leu Glu Met Thr Pro His Gln Gly
            210                 215                 220

GAG GTC TAC ACC TGC CAT GTG GAG CAT CCC AGC CTG AAG AGC CCC ATC          722
Glu Val Tyr Thr Cys His Val Glu His Pro Ser Leu Lys Ser Pro Ile
225                 230                 235

ACT GTG GAG TGG ACT AGT GGT GGC GGT GGC AGC GGC GGT GGT GGT TCC          770
Thr Val Glu Trp Thr Ser Gly Gly Gly Gly Ser Gly Gly Gly Gly Ser
240                 245                 250                 255

GGT GGC GGC GGT TCT GGC GGT GGC GGT TCC TCG AGT GAA GAC GAC ATT          818
Gly Gly Gly Gly Ser Gly Gly Gly Gly Ser Ser Ser Glu Asp Asp Ile
                260                 265                 270

GAG GCC GAC CAC GTA GGC TTC TAT GGT ACA ACT GTT TAT CAG TCT CCT          866
Glu Ala Asp His Val Gly Phe Tyr Gly Thr Thr Val Tyr Gln Ser Pro
            275                 280                 285
```

```
GGA GAC ATT GGC CAG TAC ACA CAT GAA TTT GAT GGT GAT GAG TTG TTC      914
Gly Asp Ile Gly Gln Tyr Thr His Glu Phe Asp Gly Asp Glu Leu Phe
        290                 295                 300

TAT GTG GAC TTG GAT AAG AAG AAA ACT GTC TGG AGG CTT CCT GAG TTT      962
Tyr Val Asp Leu Asp Lys Lys Lys Thr Val Trp Arg Leu Pro Glu Phe
305                 310                 315

GGC CAA TTG ATA CTC TTT GAG CCC CAA GGT GGA CTG CAA AAC ATA GCT     1010
Gly Gln Leu Ile Leu Phe Glu Pro Gln Gly Gly Leu Gln Asn Ile Ala
320                 325                 330                 335

GCA GAA AAA CAC AAC TTG GGA ATC TTG ACT AAG AGG TCA AAT TTC ACC     1058
Ala Glu Lys His Asn Leu Gly Ile Leu Thr Lys Arg Ser Asn Phe Thr
                340                 345                 350

CCA GCT ACC AAT GAG GCT CCT CAA GCG ACT GTG TTC CCC AAG TCC CCT     1106
Pro Ala Thr Asn Glu Ala Pro Gln Ala Thr Val Phe Pro Lys Ser Pro
            355                 360                 365

GTG CTG CTG GGT CAG CCC AAC ACC CTT ATC TGC TTT GTG GAC AAC ATC     1154
Val Leu Leu Gly Gln Pro Asn Thr Leu Ile Cys Phe Val Asp Asn Ile
        370                 375                 380

TTC CCA CCT GTG ATC AAC ATC ACA TGG CTC AGA AAT AGC AAG TCA GTC     1202
Phe Pro Pro Val Ile Asn Ile Thr Trp Leu Arg Asn Ser Lys Ser Val
385                 390                 395

ACA GAC GGC GTT TAT GAG ACC AGC TTC CTC GTC AAC CGT GAC CAT TCC     1250
Thr Asp Gly Val Tyr Glu Thr Ser Phe Leu Val Asn Arg Asp His Ser
400                 405                 410                 415

TTC CAC AAG CTG TCT TAT CTC ACC TTC ATC CCT TCT GAT GAT GAC ATT     1298
Phe His Lys Leu Ser Tyr Leu Thr Phe Ile Pro Ser Asp Asp Asp Ile
                420                 425                 430

TAT GAC TGC AAG GTG GAG CAC TGG GGC CTG GAG GAG CCG GTT CTG AAA     1346
Tyr Asp Cys Lys Val Glu His Trp Gly Leu Glu Glu Pro Val Leu Lys
            435                 440                 445

CAC TGG GAA CCT GAG ATT CCA GCC CCC ATG TCA GAG CTG ACA GAA ACT     1394
His Trp Glu Pro Glu Ile Pro Ala Pro Met Ser Glu Leu Thr Glu Thr
        450                 455                 460

GTG GTG TGT GCC CTG GGG TTG TCT GTG GGC CTT GTG GGC ATC GTG GTG     1442
Val Val Cys Ala Leu Gly Leu Ser Val Gly Leu Val Gly Ile Val Val
465                 470                 475

GGC ACC ATC TTC ATC ATT CAA GGC CTG CGA TCA GGT GGC ACC TCC AGA     1490
Gly Thr Ile Phe Ile Ile Gln Gly Leu Arg Ser Gly Gly Thr Ser Arg
480                 485                 490                 495

CAC CCA GGG CCT TTA TGA                                             1508
His Pro Gly Pro Leu
                500
```

(2) INFORMATION FOR SEQ ID NO: 25:

(i) SEQUENCE CHARACTERISTICS:
        (A) LENGTH: 500 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 25:

```
Met Ala Leu Gln Ile Pro Ser Leu Leu Leu Ser Ala Val Val Val
1               5                   10                  15

Leu Met Val Leu Ser Ser Pro Arg Thr Leu Ser Ile Ser Gln Ala Val
                20                  25                  30

His Ala Ala His Ala Glu Ile Asn Glu Ala Gly Arg Ala Ser Gly Gly
            35                  40                  45
```

-continued

```
Gly Gly Ser Gly Gly Gly Asn Ser Glu Arg His Phe Val Val Gln
    50              55                  60
Phe Lys Gly Glu Cys Tyr Tyr Thr Asn Gly Thr Gln Arg Ile Arg Leu
65                  70                  75                  80
Val Thr Arg Tyr Ile Tyr Asn Arg Glu Glu Tyr Val Arg Tyr Asp Ser
                85                  90                  95
Asp Val Gly Glu Tyr Arg Ala Val Thr Glu Leu Gly Arg Pro Asp Ala
            100                 105                 110
Glu Tyr Trp Asn Ser Gln Pro Glu Ile Leu Glu Arg Thr Arg Ala Glu
            115                 120                 125
Val Asp Thr Ala Cys Arg His Asn Tyr Glu Gly Pro Glu Thr Ser Thr
    130                 135                 140
Ser Leu Arg Arg Leu Glu Gln Pro Asn Val Ala Ile Ser Leu Ser Arg
145                 150                 155                 160
Thr Glu Ala Leu Asn His His Asn Thr Leu Val Cys Ser Val Thr Asp
                165                 170                 175
Phe Tyr Pro Ala Lys Ile Lys Val Arg Trp Phe Arg Asn Gly Gln Glu
            180                 185                 190
Glu Thr Val Gly Val Ser Ser Thr Gln Leu Ile Arg Asn Gly Asp Trp
            195                 200                 205
Thr Phe Gln Val Leu Val Met Leu Glu Met Thr Pro His Gln Gly Glu
    210                 215                 220
Val Tyr Thr Cys His Val Glu His Pro Ser Leu Lys Ser Pro Ile Thr
225                 230                 235                 240
Val Glu Trp Thr Ser Gly Gly Gly Ser Gly Gly Gly Ser Gly
                245                 250                 255
Gly Gly Ser Gly Gly Gly Ser Ser Glu Asp Asp Ile Glu
            260                 265                 270
Ala Asp His Val Gly Phe Tyr Gly Thr Thr Val Tyr Gln Ser Pro Gly
    275                 280                 285
Asp Ile Gly Gln Tyr Thr His Glu Phe Asp Gly Asp Glu Leu Phe Tyr
    290                 295                 300
Val Asp Leu Asp Lys Lys Lys Thr Val Trp Arg Leu Pro Glu Phe Gly
305                 310                 315                 320
Gln Leu Ile Leu Phe Glu Pro Gln Gly Gly Leu Gln Asn Ile Ala Ala
                325                 330                 335
Glu Lys His Asn Leu Gly Ile Leu Thr Lys Arg Ser Asn Phe Thr Pro
            340                 345                 350
Ala Thr Asn Glu Ala Pro Gln Ala Thr Val Phe Pro Lys Ser Pro Val
    355                 360                 365
Leu Leu Gly Gln Pro Asn Thr Leu Ile Cys Phe Val Asp Asn Ile Phe
370                 375                 380
Pro Pro Val Ile Asn Ile Thr Trp Leu Arg Asn Ser Lys Ser Val Thr
385                 390                 395                 400
Asp Gly Val Tyr Glu Thr Ser Phe Leu Val Asn Arg Asp His Ser Phe
                405                 410                 415
His Lys Leu Ser Tyr Leu Thr Phe Ile Pro Ser Asp Asp Ile Tyr
            420                 425                 430
Asp Cys Lys Val Glu His Trp Gly Leu Glu Glu Pro Val Leu Lys His
    435                 440                 445
Trp Glu Pro Glu Ile Pro Ala Pro Met Ser Glu Leu Thr Glu Thr Val
    450                 455                 460
```

```
Val Cys Ala Leu Gly Leu Ser Val Gly Leu Val Gly Ile Val Val Gly
465                 470                 475                 480

Thr Ile Phe Ile Ile Gln Gly Leu Arg Ser Gly Gly Thr Ser Arg His
                485                 490                 495

Pro Gly Pro Leu
            500

(2) INFORMATION FOR SEQ ID NO: 26:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Ile Ser Gln Ala Val His Ala Ala His Ala Glu Ile Asn Glu Ala Gly
1               5                   10                  15

(2) INFORMATION FOR SEQ ID NO: 27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Ala Pro Tyr Ser Thr Leu Leu Pro Pro Glu Leu Ser Glu Thr Pro
1               5                   10                  15

(2) INFORMATION FOR SEQ ID NO: 28:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 28:

Tyr Asp Glu Asn Pro Val Val His Phe Phe Lys Asn Ile Val Thr Pro
1               5                   10                  15

Arg Thr Pro Pro
            20

(2) INFORMATION FOR SEQ ID NO: 29:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 29:

Thr Ser Gly Gly Gly Gly Ser Gly Gly Gly Ser Ser Ser
1               5                   10

(2) INFORMATION FOR SEQ ID NO: 30:
```

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:

Glu Glu Glu Glu Tyr Met Pro Met Glu Pro Gly
 1               5                  10

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 31:

TSGGGGSGGG GSGGGGSGGG GSSS                                              24

(2) INFORMATION FOR SEQ ID NO: 32:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

Asp Glu Asn Pro Val Val His Phe Phe Lys Asn Ile Val Thr Pro Arg
 1               5                  10                  15

Thr Pro Pro (2) INFORMATION FOR SEQ ID NO: 33:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 33:

Ser Ser Ala Asp Leu Val Pro Arg Gly Ser Thr Thr Ala Pro Ser Ala
 1               5                  10                  15

Gln Leu Glu Lys Glu Leu Gln Ala Leu Glu Lys Glu Asn Ala Gln Leu
                20                  25                  30

Glu Trp Glu Leu Gln Ala Leu Glu Lys Glu Leu Ala Gln
            35                  40                  45

(2) INFORMATION FOR SEQ ID NO: 34:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

```
Ser Ser Ala Asp Leu Val Pro Arg Gly Ser Thr Thr Ala Pro Arg Ala
1               5                   10                  15

Gln Leu Lys Lys Lys Leu Gln Ala Leu Lys Lys Lys Asn Ala Gln Leu
                20                  25                  30

Lys Trp Lys Leu Gln Ala Leu Lys Lys Leu Ala Gln
        35                  40
```

(2) INFORMATION FOR SEQ ID NO: 35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 35:

ASSGGGSGGG          10

(2) INFORMATION FOR SEQ ID NO: 36:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 36:

```
Met Lys Phe Leu Val Asn Val Ala Leu Val Phe Met Val Val Tyr Ile
1               5                   10                  15

Ser Tyr Ile Tyr Ala
                20
```

(2) INFORMATION FOR SEQ ID NO: 37:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

```
Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Ser Val Arg Phe Asp Ser Asp Val Gly Glu Phe Arg
                35                  40                  45

Ala Val Thr Glu Leu Gly Arg Pro Asp Ala Glu Tyr Trp Asn Ser Gln
        50                  55                  60

Lys Asp Ile Leu Glu Gln Ala Arg Ala Ala Val Asp Thr Tyr Cys Arg
65                  70                  75                  80

His Asn Tyr Gly Val Val Glu Ser Phe Thr Val Gln Arg Arg
                85                  90
```

(2) INFORMATION FOR SEQ ID NO: 38:

(i) SEQUENCE CHARACTERISTICS:
        (A) LENGTH: 192 amino acids
        (B) TYPE: amino acid
        (C) STRANDEDNESS: single -continued (D) TOPOLOGY: linear (ii) MOLECULE TYPE: protein (xi) SEQUENCE DESCRIPTION: SEQ ID NO: 38:

```
Ile Lys Glu Glu His Val Ile Ile Gln Ala Glu Phe Tyr Leu Asn Pro
 1               5                  10                  15

Asp Gln Ser Gly Glu Phe Met Phe Asp Phe Asp Gly Asp Glu Ile Phe
             20                  25                  30

His Val Asp Met Ala Lys Lys Glu Thr Val Trp Arg Leu Glu Glu Phe
             35                  40                  45

Gly Arg Phe Ala Ser Phe Glu Ala Gln Gly Ala Leu Ala Asn Ile Ala
 50                  55                  60

Val Asp Lys Ala Asn Leu Glu Ile Met Thr Lys Arg Ser Asn Tyr Thr
 65                  70                  75                  80

Pro Ile Thr Asn Val Pro Pro Glu Val Thr Val Leu Thr Asn Ser Pro
             85                  90                  95

Val Glu Leu Arg Glu Pro Asn Val Leu Ile Cys Phe Ile Asp Lys Phe
            100                 105                 110

Thr Pro Pro Val Val Asn Val Thr Trp Leu Arg Asn Gly Lys Pro Val
        115                 120                 125

Thr Thr Gly Val Ser Glu Thr Val Phe Leu Pro Arg Glu Asp His Leu
        130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
                165                 170                 175

His Trp Glu Phe Asp Ala Pro Ser Pro Leu Pro Glu Thr Thr Glu Asn
            180                 185                 190
```